United States Patent
Tamura et al.

(10) Patent No.: US 9,890,119 B2
(45) Date of Patent: Feb. 13, 2018

(54) INDOLE AND AZAINDOLE DERIVATIVE HAVING AMPK-ACTIVATING ACTIVITY

(71) Applicant: SHIONOGI & CO., LTD., Osaka-shi (JP)

(72) Inventors: Yuusuke Tamura, Toyonaka (JP); Eiichi Kojima, Toyonaka (JP); Hidaka Ikemoto, Toyonaka (JP); Yu Hinata, Toyonaka (JP)

(73) Assignee: SHIONOGI & CO., LTD., Osaka-shi (JP)

( * ) Notice: Subject to any disclaimer, the term of this patent is extended or adjusted under 35 U.S.C. 154(b) by 3 days.

(21) Appl. No.: 14/413,337

(22) PCT Filed: Feb. 26, 2014

(86) PCT No.: PCT/JP2014/054699
§ 371 (c)(1),
(2) Date: Jan. 7, 2015

(87) PCT Pub. No.: WO2014/133008
PCT Pub. Date: Sep. 4, 2014

(65) Prior Publication Data
US 2015/0203450 A1 Jul. 23, 2015

(30) Foreign Application Priority Data

Feb. 27, 2013 (JP) .................... 2013-036578
Jul. 22, 2013 (JP) .................... 2013-151281

(51) Int. Cl.
| | |
|---|---|
| *A61K 31/5377* | (2006.01) |
| *A61K 31/4045* | (2006.01) |
| *C07D 403/12* | (2006.01) |
| *C07D 405/12* | (2006.01) |
| *C07D 413/12* | (2006.01) |
| *C07D 471/04* | (2006.01) |
| *C07D 493/04* | (2006.01) |
| *C07D 209/34* | (2006.01) |
| *C07D 209/42* | (2006.01) |
| *C07D 519/00* | (2006.01) |
| *C07H 17/02* | (2006.01) |

(52) U.S. Cl.
CPC ........ *C07D 209/34* (2013.01); *A61K 31/4045* (2013.01); *A61K 31/5377* (2013.01); *C07D 209/42* (2013.01); *C07D 403/12* (2013.01); *C07D 405/12* (2013.01); *C07D 413/12* (2013.01); *C07D 471/04* (2013.01); *C07D 493/04* (2013.01); *C07D 519/00* (2013.01); *C07H 17/02* (2013.01)

(58) Field of Classification Search
CPC ............ A61K 31/4045; A61K 31/5377; C07D 403/12; C07D 209/42; C07D 405/12; C07D 413/12; C07D 471/04; C07D 493/04
See application file for complete search history.

(56) References Cited

U.S. PATENT DOCUMENTS

| | | |
|---|---|---|
| 3,491,114 A | 1/1970 | Suh |
| 5,425,950 A | 6/1995 | Dandiker et al. |
| 2008/0214495 A1 | 9/2008 | Alstermark et al. |
| 2010/0016312 A1 | 1/2010 | Lee et al. |
| 2011/0195964 A1 | 8/2011 | Dang et al. |
| 2013/0184240 A1 | 7/2013 | Tonogaki et al. |
| 2014/0194420 A1 | 7/2014 | Kojima et al. |

FOREIGN PATENT DOCUMENTS

| | | | |
|---|---|---|---|
| DE | 10 2008 027 331 A1 | 12/2009 | |
| JP | 6-179646 A | 6/1994 | |
| JP | 2005-260212 A | 9/2005 | |
| JP | 2012-507530 A | 3/2012 | |
| WO | WO 93/22299 | * 11/1993 | |

(Continued)

OTHER PUBLICATIONS

Pastor et al., J. Med. Chem. 1997, 40, 1455-1464.*
Bartoli et al., Tetrahedron vol. 46, No. 4, pp. 1379-1384, 1990.*
Linton et al., J. Am. Chem. Soc., 2008, 130 (48), pp. 16162-16163.*
Bei B. Zhang, et al., "AMPK: An Emerging Drug Target for Diabetes and the Metabolic Syndrome" Cell Metabolism, vol. 9, No. 5, 2009, pp. 407-416.
Stefan Laufer, et al., "Investigations of SCIO-469-like compounds for the inhibition of p38 MAP kinase" Bioorganic & Medicinal Chemistry Letters, vol. 19, No. 5, 2009, pp. 1461-1464.
Zhengqiang Wang, et al., "Design and synthesis of dual inhibitors of HIV reverse transcriptase and integrase: Introducing a diketoacid functionality into delavirdine" Bioorganic & Medicinal Chemistry, vol. 16, No. 7, 2008, pp. 3587-3595.

(Continued)

*Primary Examiner* — Rebecca L Anderson
(74) *Attorney, Agent, or Firm* — Oblon, McClelland, Maier & Neustadt, L.L.P.

(57) ABSTRACT

A compound is represented by formula:

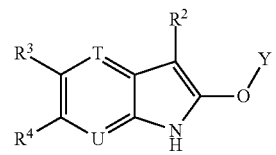

or its pharmaceutically acceptable salt, wherein Y is substituted or unsubstituted alkyl, alkenyl, alkynyl, aryl, heteroaryl, cycloalkyl, cycloalkenyl, or heterocyclyl; T is —$CR^7$= or —N=; U is —$CR^8$= or —N=; $R^2$ is hydrogen, halogen, cyano, nitro, carboxy, substituted or unsubstituted alkyl, alkenyl, acyl, carbamoyl, alkylthio, alkylsulfinyl, alkylsulfonyl, or alkyloxycarbonyl; $R^3$ is halogen, substituted or unsubstituted alkyl, alkenyl, alkynyl, aryl, heteroaryl, cycloalkyl, cycloalkenyl, heterocyclyl; and $R^4$, $R^7$ and $R^8$ are each independently hydrogen, halogen, hydroxy, cyano, nitro, carboxy, substituted or unsubstituted alkyl, alkenyl, alkynyl, aryl, heteroaryl, cycloalkyl, cycloalkenyl, or heterocyclyl.

20 Claims, No Drawings

(56) References Cited

FOREIGN PATENT DOCUMENTS

| | | |
|---|---|---|
| WO | WO 93/22299 A1 | 11/1993 |
| WO | WO 99/06396 A1 | 2/1999 |
| WO | WO 00/24753 A1 | 5/2000 |
| WO | WO 03/002533 A1 | 1/2003 |
| WO | WO 03/097065 A1 | 11/2003 |
| WO | WO 2004/108671 A1 | 12/2004 |
| WO | WO 2007/020050 A2 | 2/2007 |
| WO | WO 2008/154271 A1 | 12/2008 |
| WO | WO 2009/023179 A2 | 2/2009 |
| WO | WO 2010/036613 A1 | 4/2010 |
| WO | WO 2010/047982 A1 | 4/2010 |
| WO | WO 2010/051176 A1 | 5/2010 |
| WO | WO 2010/051206 A1 | 5/2010 |
| WO | WO 2010/101127 A1 | 9/2010 |
| WO | WO 2011/106273 A1 | 9/2011 |
| WO | WO 2012/033149 A1 | 3/2012 |
| WO | WO 2012/116145 A1 | 8/2012 |
| WO | WO 2013/011932 A1 | 1/2013 |
| WO | WO 2013/153479 A2 | 10/2013 |
| WO | WO 2014/031441 A1 | 2/2014 |
| WO | WO 2014/031445 A1 | 2/2014 |
| WO | WO 2014/031465 A1 | 2/2014 |
| WO | WO 2014/031468 A1 | 2/2014 |
| WO | WO 2014/031515 A1 | 2/2014 |
| WO | WO 2014/031517 A1 | 2/2014 |
| WO | WO 2014/128549 A1 | 8/2014 |
| WO | WO 2014/139388 A1 | 9/2014 |

OTHER PUBLICATIONS

Trung Cao, et al., "Copper(II)- and Palladium(II)-Catalyzed Enantioselective Claisen Rearrangement of Allyloxy- and Propargyloxy-Indoles to Quaternary Oxindoles and Spirocyclic Lactones" Journal of Organic Chemistry, vol. 77, No. 24, 2012, pp. 11034-11055.

International Search Report issued Apr. 22, 2014 in PCT/JP2014/054699.

File Registry on STN, RN 70029-52-6, Entered STN: Nov. 16, 1984.

Terence G. Hamill, et al., "Non-Peptide Fibrinogen Receptor Antagonists. 4[1]. The Synthesis of [$^3$H]L-756,568." Journal of Labelled Compounds & Radiopharmaceuticals, vol. 42, No. 6, 1999, pp. 605-609.

L.M. Zorin, et al., "Reactions of 2-acetylindolyl-3-carboxylic acids" Khimiya Geterotsiklicheskikh Soedinenii, vol. 9, 1984, 2 pages (English Abstract only).

V.I. Gorgos, et al., "Synthesis of 2-acylindoles from α-(N-isatinyl) ketones" Khimiya Geterotsiklicheskikh Soedinenii, vol. 11, 1983, 2 pages (English Abstract only).

G. I. Zhungietu, et al., "Synthesis of 5H-pyridazo[4,5-b]indoles by the condensation of 2-acylindolyl-3-carboxylic acids with hydrazine" Khimiya Geterotsiklicheskikh Soedinenii, vol. 8, 1982, 2 pages (English Abstract only).

G. I. Zhungietu, et al., "Recyclization of N-acetonylisatins to 2-acetylindole-3-carboxylic acids" Izvestiya Akademii Nauk Moldavskoi SSR, Biologicheskie i Khimicheskie Nauki, vol. 2, 1981, 3 pages (English Abstract only).

G. I. Zhungietu, et al., "General method for producing 2-acylindole-3-carboxylic acids by recyclization of α-(N-isatinyl) ketones" Izvestiya Akademii Nauk Moldavskoi SSR, Biologicheskie i Khimicheskie Nauki, vol. 3, 1980, 3 pages (English Abstract only).

David St. C. Black, et al., "A Simple Synthesis of 2-Acyl Indoles from Isatins" Journal of the Chemical Society, Chemical Communications, vol. 4, 1980, p. 200.

Klára Esses-Reiter, et al., "Attempted Synthesis of a Tenidap Isomer and Formation of an Unexpected Stable Water Adduct" Heterocyclic Chemistry vol. 37, No. 4, 2000, pp. 927-933.

Gary M. Karp, "Regioselective alkylation of phenoxy-substituted 3-(methylthio)indolin-2(3H)-ones. Preparation of 3-, 1,3-, and 1,3,3-substituted indolin-2(3H)-ones" Journal of Organic Chemistry, vol. 57, No. 17, 1992, 4 pages (English Abstract only).

Extended Search Report dated Aug. 12, 2016 in European Patent Application No. 14756889.3.

Trung Cao, et al., "Asymmetric synthesis of allenyl oxindoles and spirooxindoles by a catalytic enantioselective Saucy-Marbet Claisen Rearrangement", Angrew. Chem. Int. Ed., vol. 51, No. 27, XP002760362, Jan. 2012, pp. 2448-2451.

* cited by examiner

INDOLE AND AZAINDOLE DERIVATIVE HAVING AMPK-ACTIVATING ACTIVITY

FIELD OF THE INVENTION

The present invention relates to a compound which has an activating effect on adenosine monophosphate-activated protein kinase (hereinafter referred to as AMPK) and is useful as a medicine.

BACKGROUND ART

AMPK is a serine-threonine kinase, which is activated by AMP, and has three subunits, α, β and γ. In each subunit, there exist multiple isoforms (α1, α2, β1, β2, γ1, γ2 and γ3).
AMPK is involved in various physiological functions, such as suppression of gluconeogenesis and inhibition of fatty acid synthesis in liver and incorporation of sugars and an increase in fatty acid oxidation in skeletal muscles, as an energy sensor in living organisms, and has attracted attention as a target molecule of a therapeutic agent for diabetes. Therefore, an AMPK activator is expected to be effective in the treatment of diabetes as an insulin resistance improving drug, which has an insulin independent hypoglycemic effect and a lipid improving effect (Non-Patent Document 1).
Patent Documents 1 to 8 disclose a variety of compounds having an AMPK activating effect. However, an indole derivative like the compound of the present invention is not disclosed in any of the documents.
Patent Document 9 describes the derivatives substituted with —C(=O)— group at the 2-position of indole as compounds useful for a remedy for benign prostatic hyperplasia.
Patent Document 10 describes the following compounds as compounds useful for the treatment of hepatitis C.

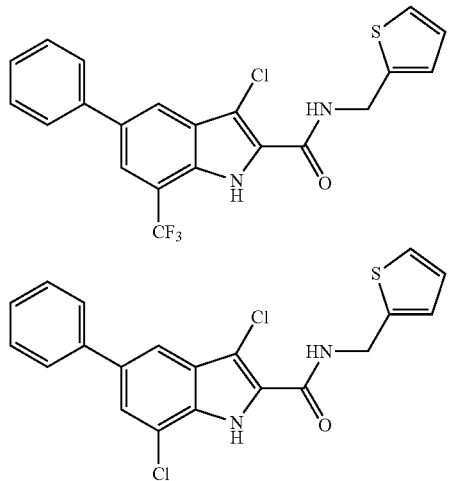

Patent Document 11 describes the derivatives substituted with —C(=O)NH— group at the 2-position of indole as compounds useful for the treatment of HIV.
Patent Document 12 describes the derivatives substituted with —C(=O)— group at the 2-position of indole as compounds useful for the treatment of psychosis.
Patent Document 13 describes the derivatives substituted with —C(=O)NH— group at the 2-position of indole as compounds useful for the treatment of obesity or atherosclerosis.

Patent Document 14 describes the following compound as a compound useful for ultraviolet absorbers.

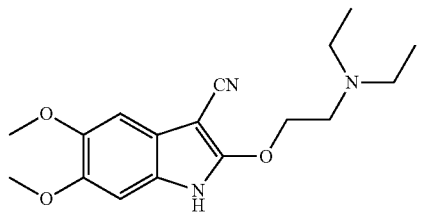 [SMILES: CCN(CC)CCOc1[nH]c2cc(OC)c(OC)cc2c1C#N]

Patent Document 15 describes the following compound as a compound useful for the treatment of hypertension.

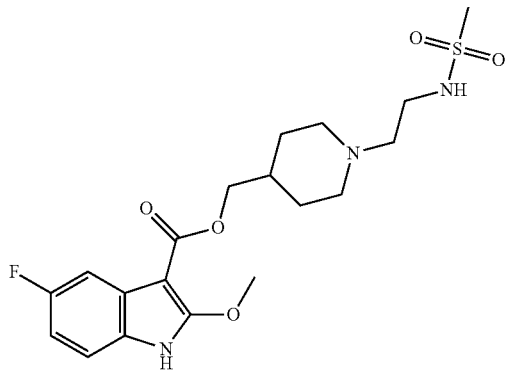 [SMILES: COc1[nH]c2ccc(F)cc2c1C(=O)OCC1CCN(CCNS(C)(=O)=O)CC1]

Patent Document 16 describes the following compounds as compounds useful for the chromogenic substrates of sialidases.

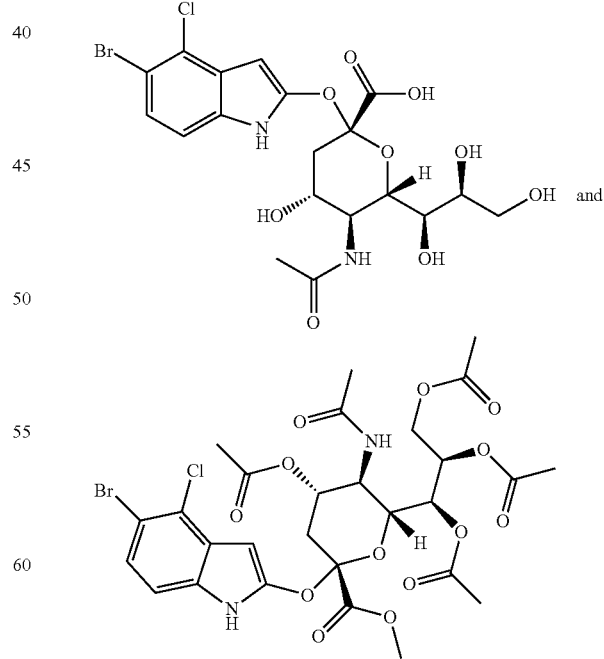

Patent Document 17 describes the following compound as compounds useful for agrochemicals.

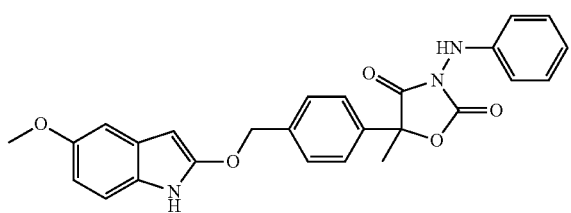 [SMILES: COc1ccc2[nH]c(OCc3ccc(C4(C)OC(=O)N(Nc5ccccc5)C4=O)cc3)cc2c1]

Patent Document 18 describes the following compound as a compound useful for insecticides.

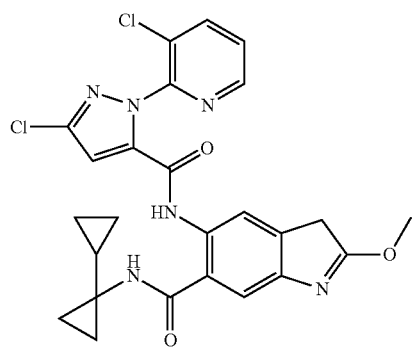 [SMILES: COC1=Nc2cc(C(=O)NC3(C4CC4)CC3)c(NC(=O)c3cc(Cl)nn3-c3ncccc3Cl)cc2C1]

Patent Document 19 describes the following compound as a compound useful for organic semiconductor materials.

Patent Document 20 describes the following compounds as compounds useful for the treatment of cancer.

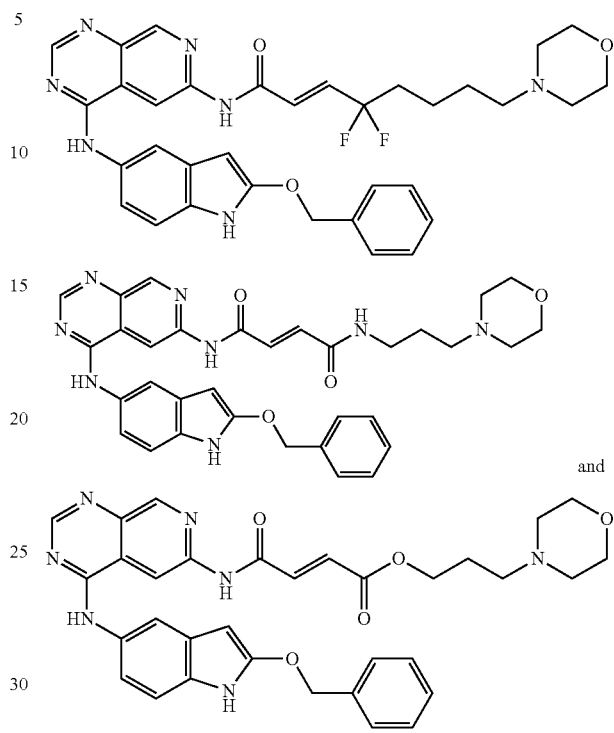

Patent Document 21 describes the following compound as compounds useful for herbicides.

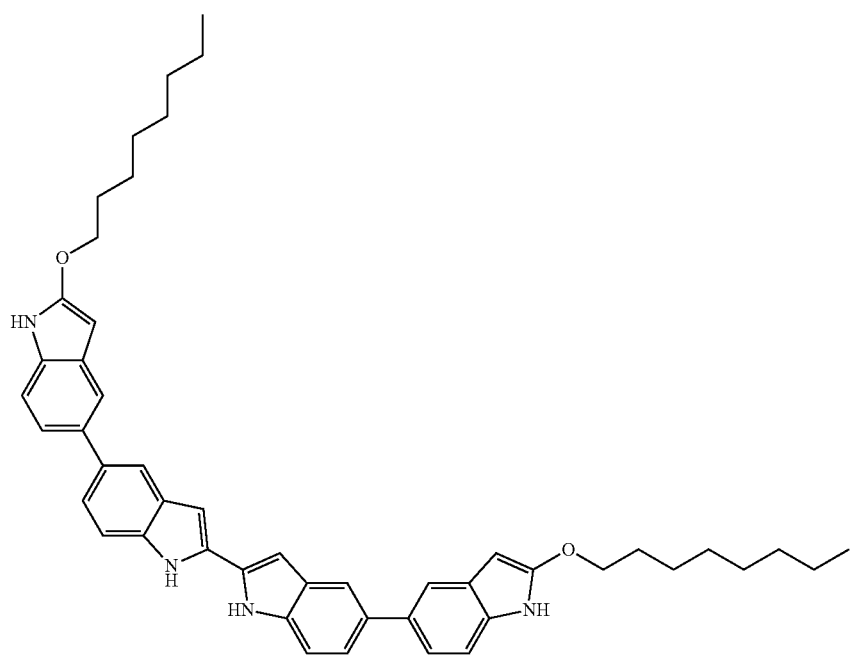 [SMILES: CCCCCCCCOc1cc2cc(-c3ccc4[nH]c(-c5cc6cc(-c7ccc8[nH]c(OCCCCCCCC)cc8c7)ccc6[nH]5)cc4c3)ccc2[nH]1]

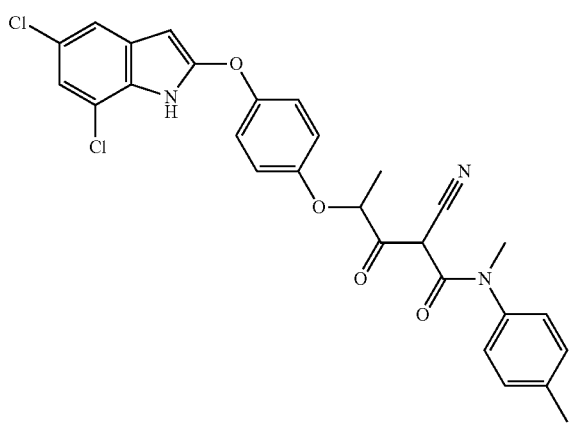 [SMILES: Cc1ccc(N(C)C(=O)C(C#N)C(=O)C(C)Oc2ccc(Oc3cc4cc(Cl)cc(Cl)c4[nH]3)cc2)cc1]

Patent Document 22 describes the following compound as compounds useful for ultraviolet absorbers.

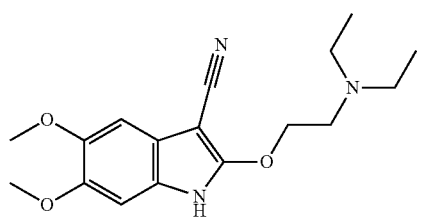 [SMILES: CCN(CC)CCOc1[nH]c2cc(OC)c(OC)cc2c1C#N]

However, any of Patent Documents 9 to 22 does not disclose the AMPK activating effect.

Non-patent Document 2 describes the derivatives substituted with —C(=O)— group at the 2-position of indole as compounds useful for the treatment of rheumatoid arthritis.

Non-patent Document 3 describes the derivatives substituted with —C(=O)— group at the 2-position of indole as compounds useful for the treatment of HIV.

Non-patent Document 4 describes the derivatives substituted with —C(=O)NH— group at the 2-position of indole as compounds useful for the treatment of cardiovascular disease.

Non-patent Documents 5 to 9 disclose the derivatives substituted with —C(=O)— group at the 2-position of indole.

Non-patent Document 10 describes the derivatives substituted with —C(=O)— group at the 2-position of indole as compounds useful for the treatment of insomnia.

Non-patent Document 11 describes the derivatives substituted with ethoxy group at the 2-position of indole and chloro group at the 5-position of indole.

Non-patent Document 12 describes the derivatives substituted with isopropyl group at the 2-position of indole and —S—CH₃ group at the 3-position of indole.

Non-patent Document 13 describes the following compounds.

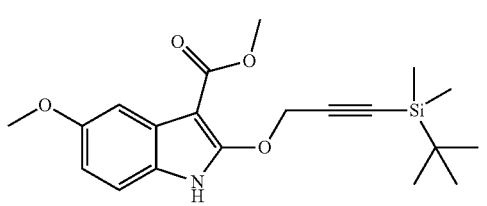

and

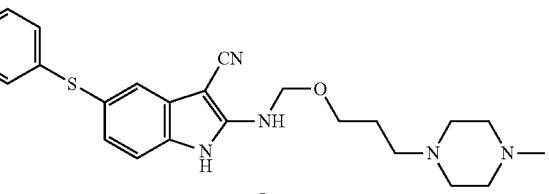

However, any of Non-patent Documents 2 to 13 does not disclose the AMPK activating effect.

The following compounds are hit by searching structures on SciFinder (online database), but there is no literature information and the AMPK activating effect of the compounds is not described.

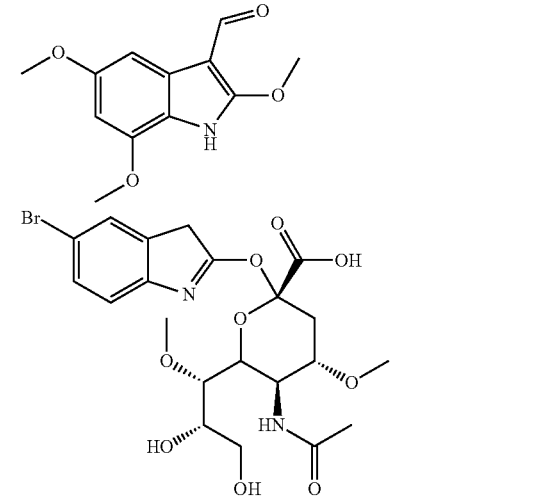

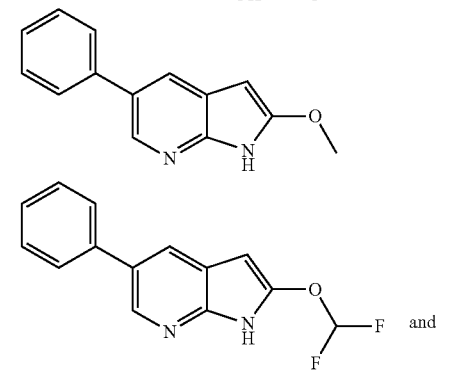

PRIOR ART DOCUMENT

Patent Document

Patent Document 1: WO 2010/036613
Patent Document 2: WO 2010/047982
Patent Document 3: WO 2010/051176
Patent Document 4: WO 2010/051206
Patent Document 5: WO 2011/106273
Patent Document 6: WO 2012/116145
Patent Document 7: WO 2012/033149
Patent Document 8: WO 2013/011932
Patent Document 9: WO 2010/101127
Patent Document 10: WO 2009/023179
Patent Document 11: WO 2008/154271
Patent Document 12: WO 2004/108671
Patent Document 13: WO 2003/002533
Patent Document 14: U.S. Pat. No. 3,491,114B
Patent Document 15: WO 2003/09706
Patent Document 16: WO 2000/024753
Patent Document 17: WO 1993/22299
Patent Document 18: WO 2007/020050
Patent Document 19: JP 2005-260212A
Patent Document 20: WO 1999/06396
Patent Document 21: JP 1994-179646A
Patent Document 22: U.S. Pat. No. 3,491,114B Non-Patent Document Non-Patent Document 1: Cell Metabolism Vol. 9, Issue 5, 407-416, 2009
Non-Patent Document 2: Bioorganic & Medicinal Chemistry Letters, Volume: 19, Issue: 5, Pages: 1461-1464
Non-Patent Document 3: Bioorganic & Medicinal Chemistry, Volume: 16, Issue: 7, Pages: 3587-3595
Non-Patent Document 4: Journal of Labelled Compounds & Radiopharmaceuticals, Volume: 42, Issue: 6, Pages: 605-609
Non-Patent Document 5: Khimiya Geterotsiklicheskikh Soedinenii, Issue: 9, Pages: 1211-13
Non-Patent Document 6: Khimiya Geterotsiklicheskikh Soedinenii, Issue: 11, Pages: 1490-2
Non-Patent Document 7: Khimiya Geterotsiklicheskikh Soedinenii, Issue: 8, Pages: 1064-8, Journal, 1982
Non-Patent Document 8: Izvestiya Akademii Nauk Moldayskoi SSR, Biologicheskie i Khimicheskie Nauki, Issue: 2, Pages: 57-65
Non-Patent Document 9: Izvestiya Akademii Nauk Moldayskoi SSR, Biologicheskie i Khimicheskie Nauki, Issue: 3, Pages: 61-7
Non-Patent Document 10: Journal of the Chemical Society, Chemical Communications, Issue: 4, Pages: 200
Non-Patent Document 11: Heterocyclic Chemistry (2000), 37(4), Pages: 927-933
Non-Patent Document 12: Organic Chemistry (1992), 57(17), Pages: 4765-72
Non-Patent Document 13: Journal of Organic Chemistry (2012), 77(24), Pages: 11034-11055

DISCLOSURE OF INVENTION

Problems to be Solved by the Invention

An object of the present invention is to provide an excellent AMPK activator.

Means for Solving the Problem

As a result of intensive research, the present inventors succeeded in synthesizing an excellent compound having an AMPK activating effect.

The present invention relates to the following.

[1]

A compound represented by formula (I):

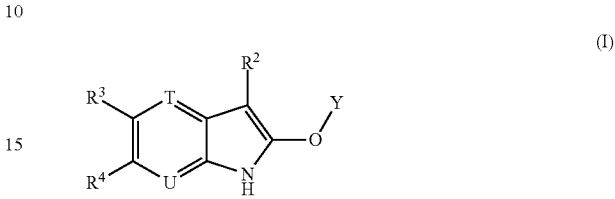

or its pharmaceutically acceptable salt,
wherein
Y is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;
T is $-CR^7=$ or $-N=$;
U is $-CR^8=$ or $-N=$;
$R^2$ is hydrogen, halogen, cyano, nitro, carboxy, substituted or unsubstituted alkyl, substituted or unsubstituted alkenyl, substituted or unsubstituted acyl, substituted or unsubstituted carbamoyl, substituted or unsubstituted alkylthio, substituted or unsubstituted alkylsulfinyl, substituted or unsubstituted alkylsulfonyl, or substituted or unsubstituted alkyloxycarbonyl;
$R^3$ is halogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;
$R^4$, $R^7$ and $R^8$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino; with the proviso that a compound wherein Y is substituted or unsubstituted alkyl, T is —CR$^7$=, U is —CR$^8$=, and R$^3$ is halogen;

a compound wherein Y is substituted or unsubstituted alkyl, T is —CR$^7$=, U is —CR$^8$=, and R$^2$ is substituted or unsubstituted acyl, or substituted or unsubstituted alkylthio; a compound wherein Y is substituted or unsubstituted alkyl, substituted or unsubstituted alkenyl, or substituted or unsubstituted alkynyl, T is —CR$^7$=, U is —CR$^8$=, and R$^2$ is substituted or unsubstituted alkyloxycarbonyl; and compounds shown below are excluded:

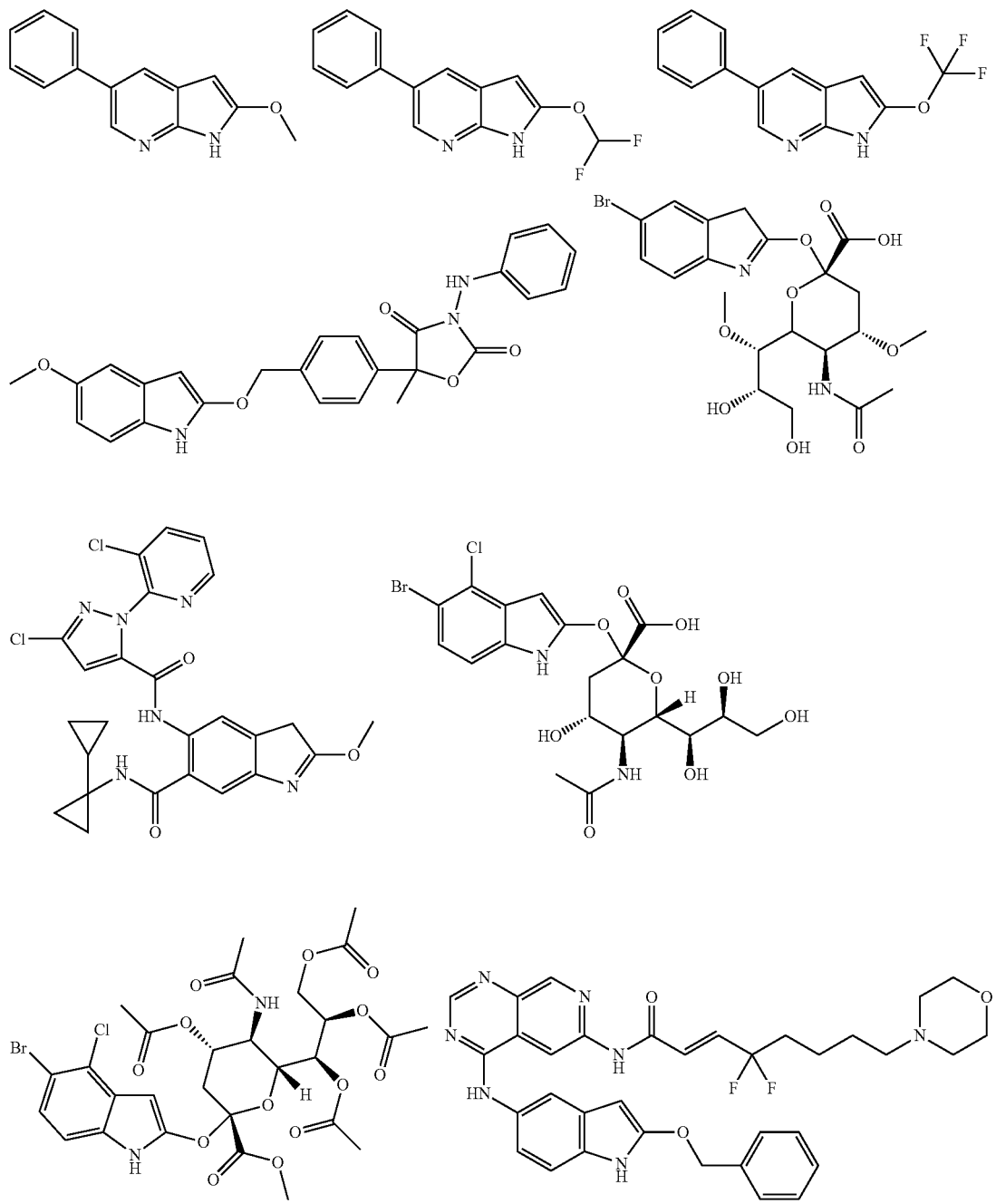

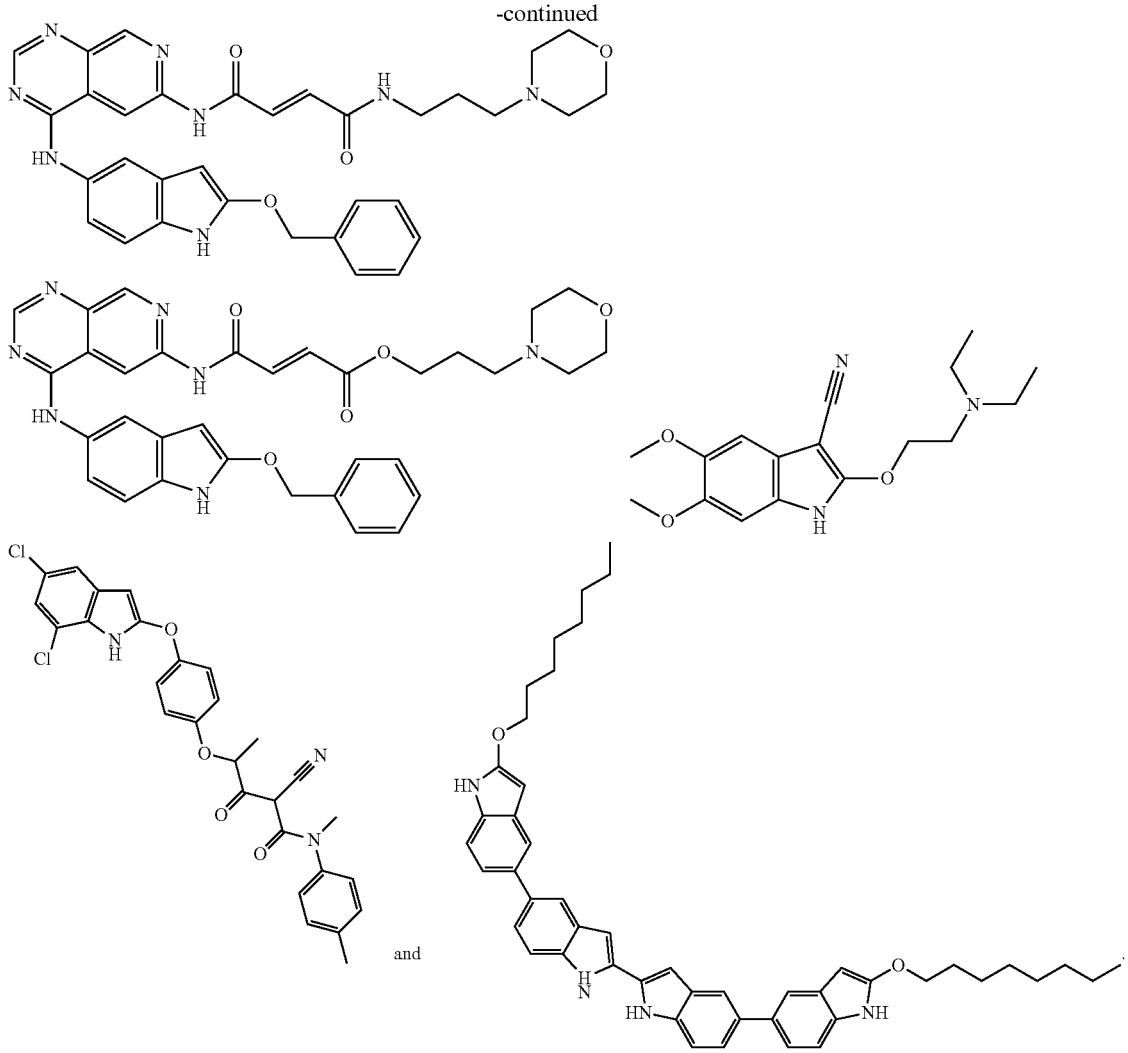

and

[2]

The compound according to the above [1] or its pharmaceutically acceptable salt, wherein Y is substituted or unsubstituted aryl, substituted or unsubstituted heteroaryl, substituted or unsubstituted cycloalkyl, substituted or unsubstituted cycloalkenyl, or substituted or unsubstituted heterocyclyl.

[3]

The compound according to the above [1] or [2], or its pharmaceutically acceptable salt, wherein Y is substituted or unsubstituted aryl, substituted or unsubstituted cycloalkyl, or substituted or unsubstituted heterocyclyl.

[4]

The compound according to any one of the above [1] to [3] or its pharmaceutically acceptable salt, wherein Y is substituted or unsubstituted heterocyclyl.

[5]

The compound according to the above [4] or its pharmaceutically acceptable salt, wherein Y is substituted or unsubstituted heterocyclyl and the substituted or unsubstituted heterocyclyl is

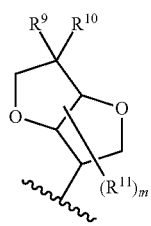

wherein $R^9$ and $R^{10}$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino;

$R^{11}$ is each independently halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino;

m is an integer from 0 to 7.

[6]

The compound according to any one of the above [1] to [5] or its pharmaceutically acceptable salt, wherein $R^3$ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino.

[7]

The compound according to any one of the above [1] to [6] or its pharmaceutically acceptable salt, wherein $R^3$ is substituted or unsubstituted aryl, substituted or unsubstituted heteroaryl, or substituted or unsubstituted alkyloxy.

[8]

The compound according to any one of the above [1] to [7] or its pharmaceutically acceptable salt, wherein $R^3$ is substituted or unsubstituted aryl.

[9]

The compound according to any one of the above [1] to [8] or its pharmaceutically acceptable salt, wherein $R^2$ is hydrogen, halogen, cyano, carboxy, or substituted or unsubstituted carbamoyl.

[10]

The compound according to the above [9] or its pharmaceutically acceptable salt, wherein $R^2$ is hydrogen, halogen, or cyano.

[11]

The compound according to any one of the above [1] to [10] or its pharmaceutically acceptable salt, wherein $R^4$ is hydrogen or halogen.

[12]

The compound according to any one of the above [1] to [11] or its pharmaceutically acceptable salt, wherein T is —$CR^7$=.

[13]

The compound according to any one of the above [1] to [11] or its pharmaceutically acceptable salt, wherein T is —N=.

[14]

The compound according to any one of the above [1] to [13] or its pharmaceutically acceptable salt, wherein U is —$CR^8$=.

[15]

A pharmaceutical composition having an activating effect on adenosine monophosphate-activated protein kinase, which comprises a compound represented by formula (II):

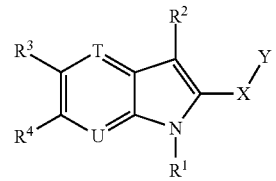

(II)

or its pharmaceutically acceptable salt,
wherein
X is —O—, —S—, —$NR^5$—, —C(=O)—, —C(=O)$NR^6$—, or —$SO_2$—;
$R^5$ is hydrogen, or substituted or unsubstituted alkyl;
$R^6$ is hydrogen, or substituted or unsubstituted alkyl;
Y is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;
T is —$CR^7$= or —N=;
U is —$CR^8$= or —N=;
$R^1$ is hydrogen, substituted or unsubstituted alkyl, or substituted or unsubstituted amino;
$R^2$ is hydrogen, halogen, cyano, nitro, carboxy, substituted or unsubstituted alkyl, substituted or unsubstituted alkenyl, substituted or unsubstituted acyl, substituted or unsubstituted carbamoyl, substituted or unsubstituted alkylthio, substituted or unsubstituted alkylsulfinyl, substituted or unsubstituted alkylsulfonyl, or substituted or unsubstituted alkyloxycarbonyl;
$R^3$ is halogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;
$R^4$, $R^7$ and $R^8$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino; with the proviso that a compound wherein Y is substituted or unsubstituted alkyl, T is —$CR^7$=, U is —$CR^8$=, and $R^3$ is halogen; and a compound wherein X is —C(=O)$NR^6$—, T is —$CR^7$=, U is —$CR^8$=, and $R^3$ is substituted or unsubstituted amino are excluded.

[16]
A pharmaceutical composition comprising the compound according to any one of the above [1] to [14], or its pharmaceutically acceptable salt.

[17]
The pharmaceutical composition according to the above [16], which has an activating effect on adenosine monophosphate-activated protein kinase.

[18]
The pharmaceutical composition according to any one of the above [15] to [17], for the treatment and/or prevention of diabetes.

[19]
A method for preventing or treating diabetes, comprising administering the compound according to any one of the above [1] to [14], or its pharmaceutically acceptable salt.

[20]
The compound according to any one of the above [1] to [14], or its pharmaceutically acceptable salt, for the treatment and/or prevention of diabetes.

[21]
A pharmaceutical composition for oral administration, comprising a compound represented by formula (I):

or its pharmaceutically acceptable salt,
wherein
Y is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;
T is —$CR^7$= or —N=;
U is —$CR^8$= or —N=;
$R^2$ is hydrogen, halogen, cyano, nitro, carboxy, substituted or unsubstituted alkyl, substituted or unsubstituted alkenyl, substituted or unsubstituted acyl, substituted or unsubstituted carbamoyl, substituted or unsubstituted alkylthio, substituted or unsubstituted alkylsulfinyl, substituted or unsubstituted alkylsulfonyl, or substituted or unsubstituted alkyloxycarbonyl;

$R^3$ is halogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;

$R^4$, $R^7$ and $R^8$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino; with the proviso that a compound wherein Y is substituted or unsubstituted alkyl, T is —$CR^7$=, U is —$CR^8$=, and $R^3$ is halogen;

a compound wherein Y is substituted or unsubstituted alkyl, T is —$CR^7$=, U is —$CR^8$=, and $R^2$ is substituted or unsubstituted acyl, or substituted or unsubstituted alkylthio; a compound wherein Y is substituted or unsubstituted alkyl, substituted or unsubstituted alkenyl, or substituted or unsubstituted alkynyl, T is —$CR^7$=, U is —$CR^8$=, and $R^2$ is substituted or unsubstituted alkyloxycarbonyl; and compounds shown below are excluded:
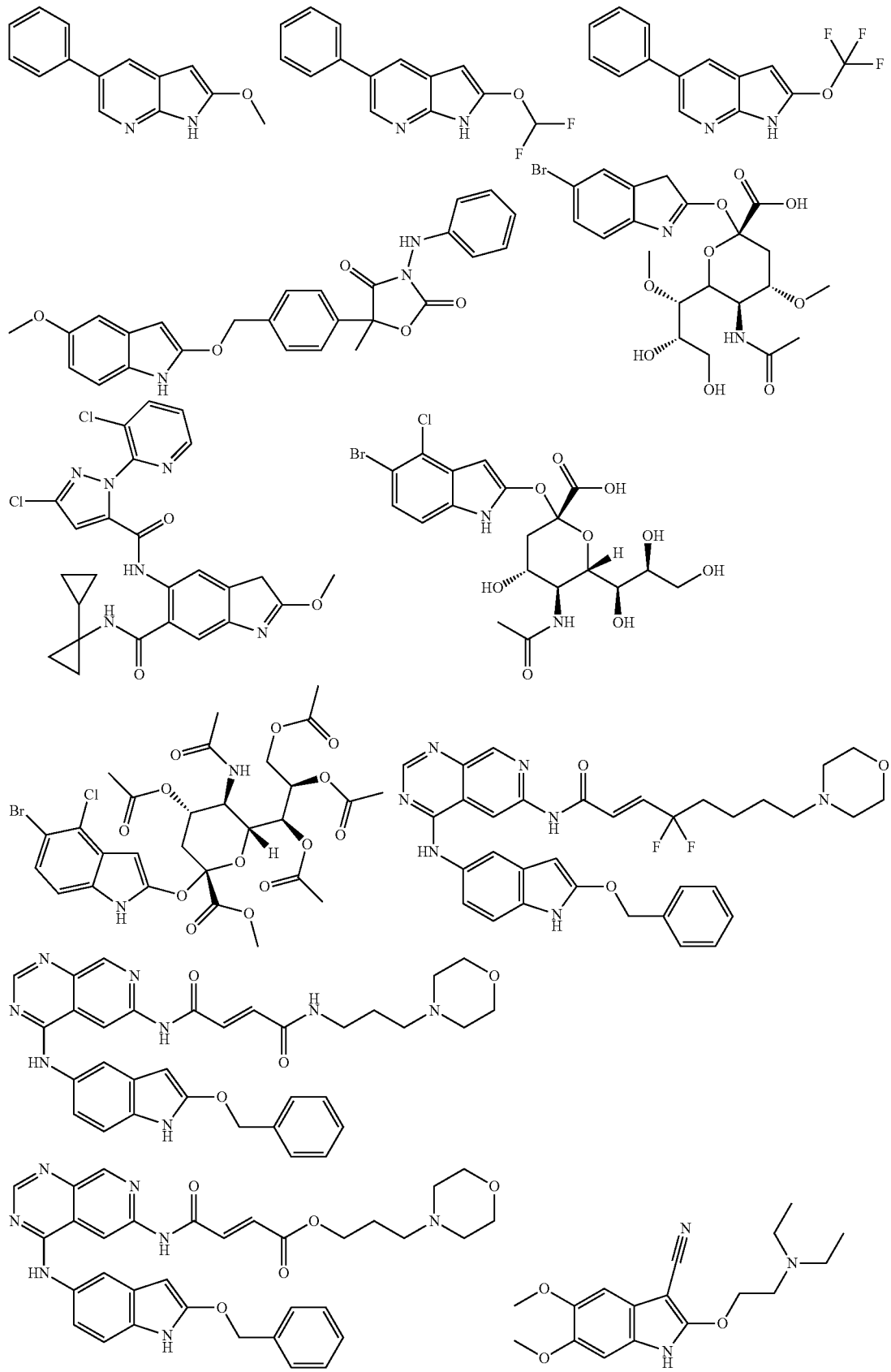

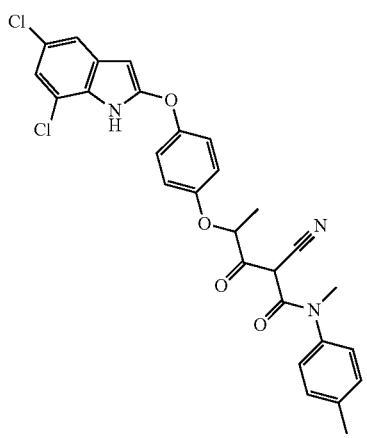

and

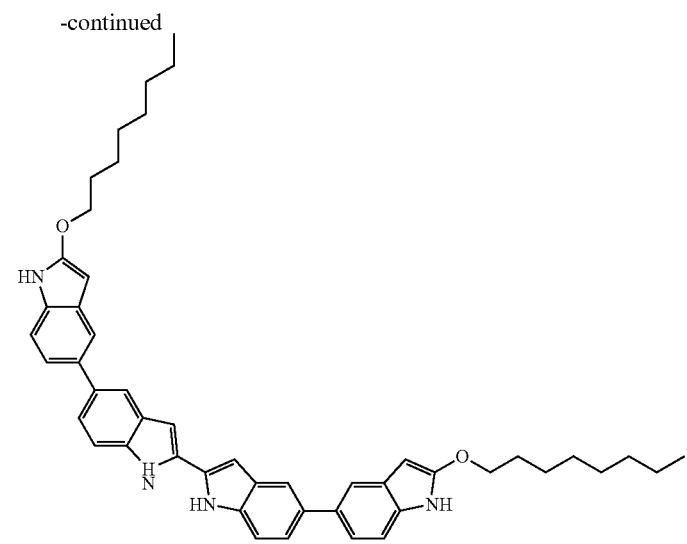

[22]

The pharmaceutical composition according to the above [21], which is a tablet, powder, granule, capsule, pill, film, suspension, emulsion, elixir, syrup, lemonade, spirit, aromatic water, extract, decoction or tincture.

[23]

The pharmaceutical composition according to the above [22], which is a sugar-coated tablet, film-coated tablet, enteric-coated tablet, sustained-release tablet, troche tablet, sublingual tablet, buccal tablet, chewable tablet, orally dispersing tablet, dry syrup, soft capsule, micro capsule or sustained-release capsule.

[24]

A pharmaceutical composition for parenteral administration, comprising a compound represented by formula (I):

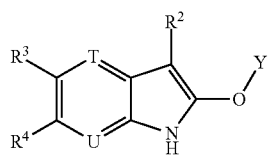

or its pharmaceutically acceptable salt,
wherein
Y is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;
T is $-CR^7=$ or $-N=$;
U is $-CR^8=$ or $-N=$;
$R^2$ is hydrogen, halogen, cyano, nitro, carboxy, substituted or unsubstituted alkyl, substituted or unsubstituted alkenyl, substituted or unsubstituted acyl, substituted or unsubstituted carbamoyl, substituted or unsubstituted alkylthio, substituted or unsubstituted alkylsulfinyl, substituted or unsubstituted alkylsulfonyl, or substituted or unsubstituted alkyloxycarbonyl;
$R^3$ is halogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;
$R^4$, $R^7$ and $R^8$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino; with the proviso that a compound wherein Y is substituted or unsubstituted alkyl, T is —CR$^7$=, U is —CR$^8$=, and R$^3$ is halogen;

a compound wherein Y is substituted or unsubstituted alkyl, T is —CR$^7$=, U is —CR$^8$=, and R$^2$ is substituted or unsubstituted acyl, or substituted or unsubstituted alkyl-thio; a compound wherein Y is substituted or unsubstituted alkyl, substituted or unsubstituted alkenyl, or substituted or unsubstituted alkynyl, T is —CR$^7$=, U is —CR$^8$=, and R$^2$ is substituted or unsubstituted alkyloxycarbonyl; and compounds shown below are excluded:

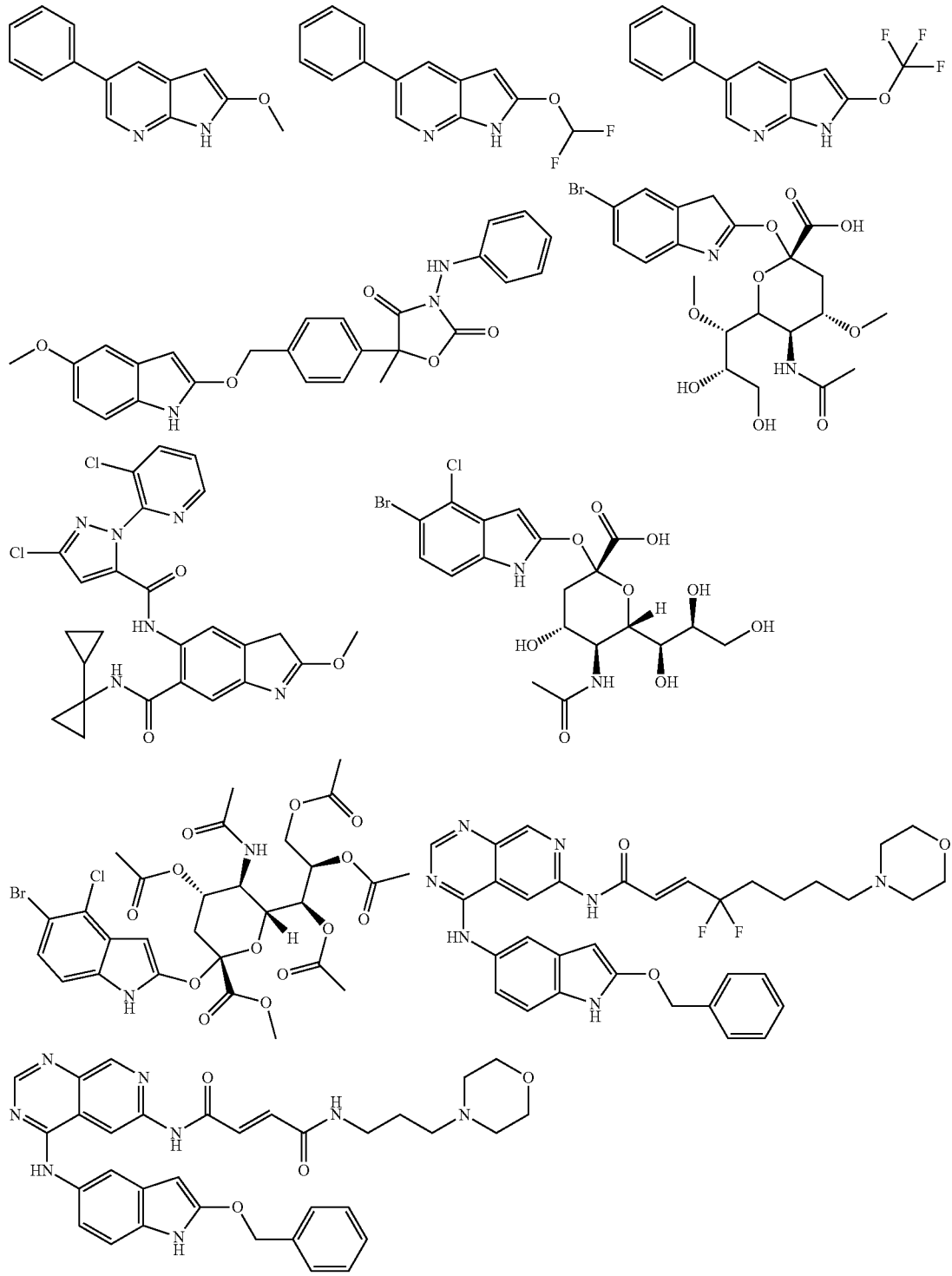

-continued

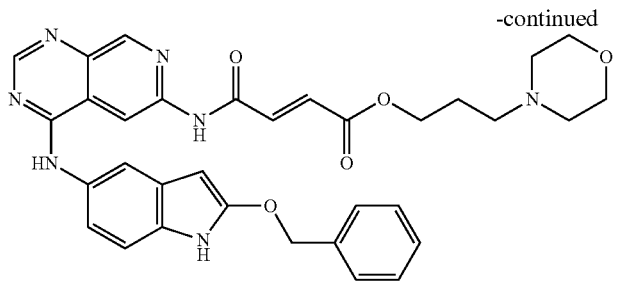

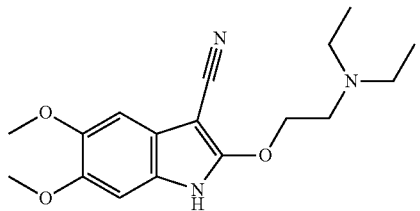

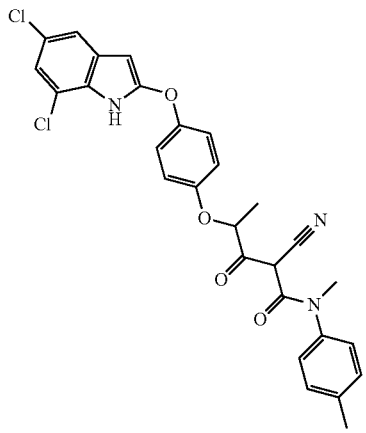

and

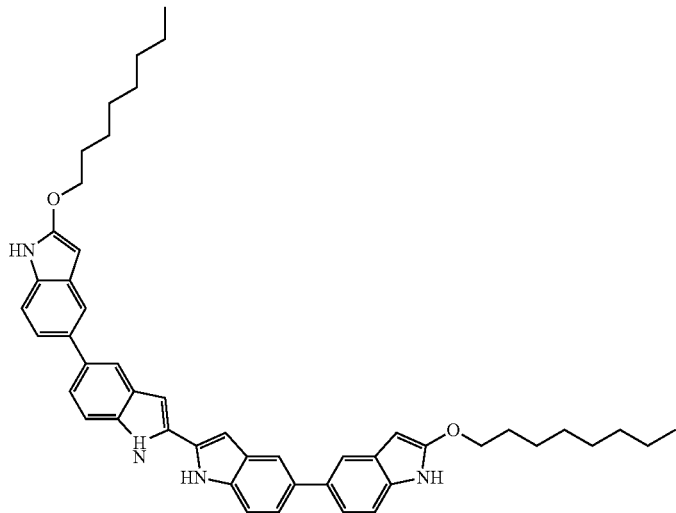

[25]
The pharmaceutical composition according to the above [24], for dermal, subcutaneous, intravenous, intraarterial, intramuscular, intraperitoneal, transmucosal, inhalation, transnasal, ophthalmic, inner ear or vaginal administration.

[26]
The pharmaceutical composition according to the above [24] or [25], which is injection, infusion, eye drop, nose drop, ear drop, aerosol, inhalation, lotion, impregnation, liniment, mouthwash, enema, ointment, plaster, jelly, cream, patch, cataplasm, external powder or suppository.

[27]
A pharmaceutical composition for a pediatric or geriatric patient, comprising a compound represented by formula (I):

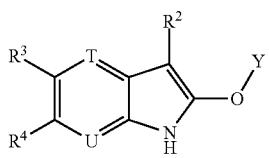 (I)

or its pharmaceutically acceptable salt,
wherein
Y is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;
T is —CR$^7$= or —N=;
U is —CR$^8$= or —N=;

R$^2$ is hydrogen, halogen, cyano, nitro, carboxy, substituted or unsubstituted alkyl, substituted or unsubstituted alkenyl, substituted or unsubstituted acyl, substituted or unsubstituted carbamoyl, substituted or unsubstituted alkylthio, substituted or unsubstituted alkylsulfinyl, substituted or unsubstituted alkylsulfonyl, or substituted or unsubstituted alkyloxycarbonyl;

R$^3$ is halogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;

R$^4$, R$^7$ and R$^8$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino; with the proviso that a compound wherein Y is substituted or unsubstituted alkyl, T is —$CR^7$=, U is —$CR^8$=, and $R^3$ is halogen;

a compound wherein Y is substituted or unsubstituted alkyl, T is —$CR^7$=, U is —$CR^8$=, and $R^2$ is substituted or unsubstituted acyl, or substituted or unsubstituted alkylthio; a compound wherein Y is substituted or unsubstituted alkyl, substituted or unsubstituted alkenyl, or substituted or unsubstituted alkynyl, T is —$CR^7$=, U is —$CR^8$=, and $R^2$ is substituted or unsubstituted alkyloxycarbonyl; and compounds shown below are excluded:

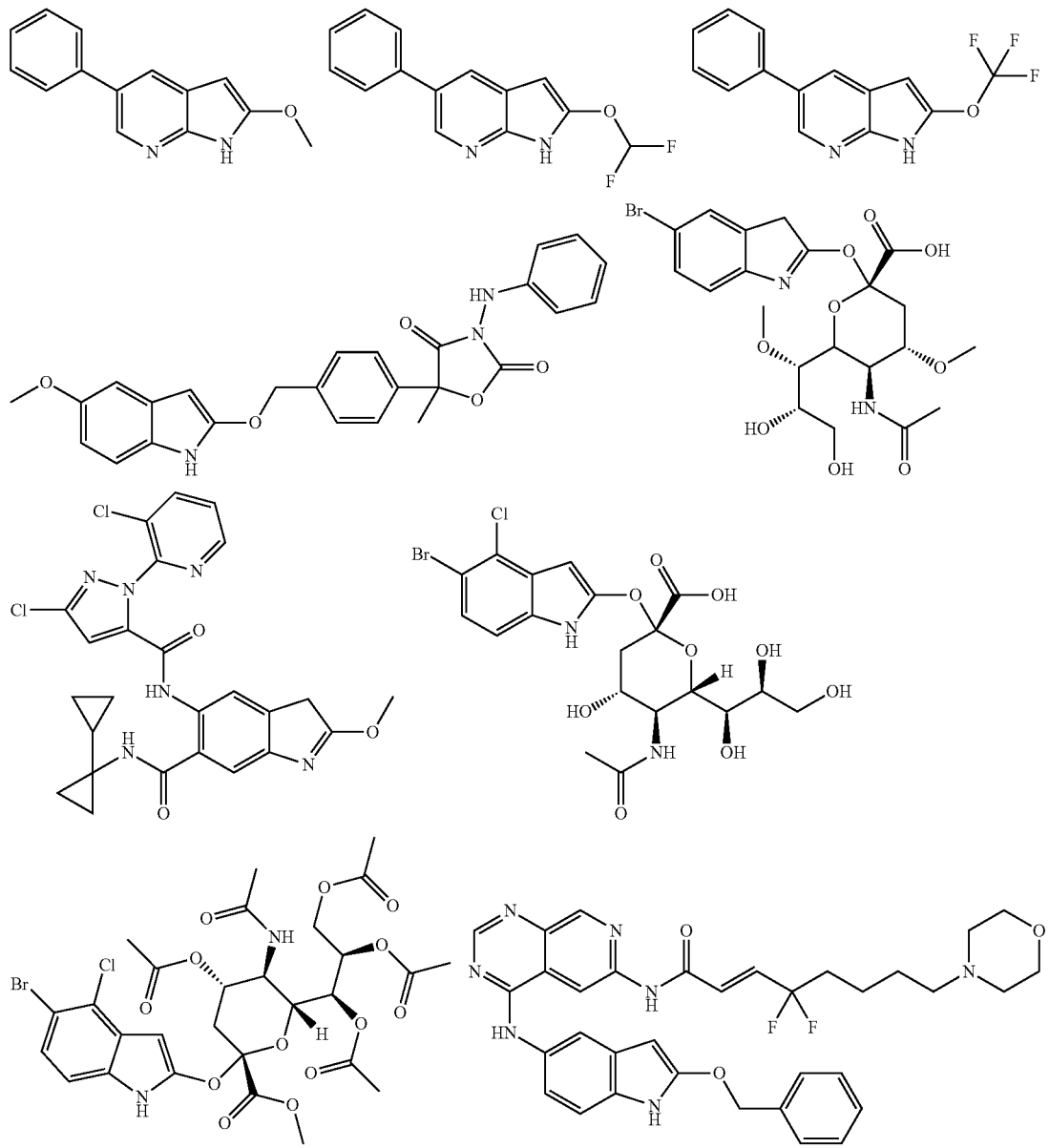

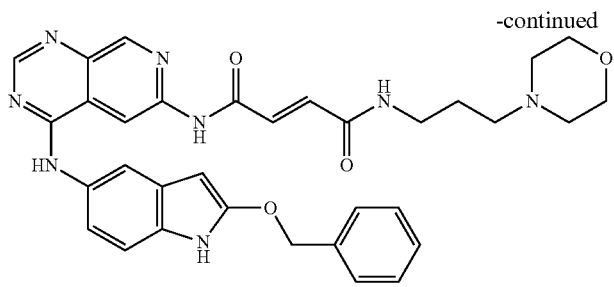

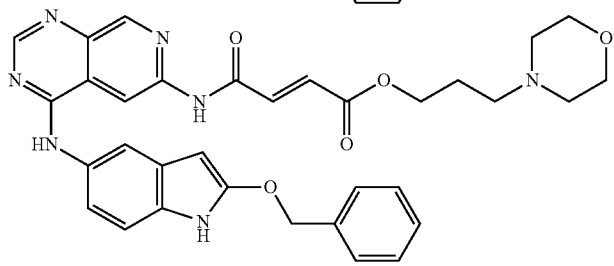

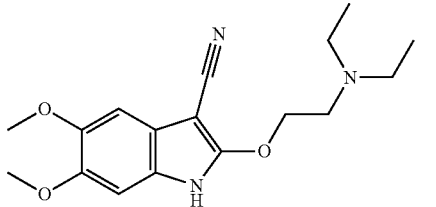

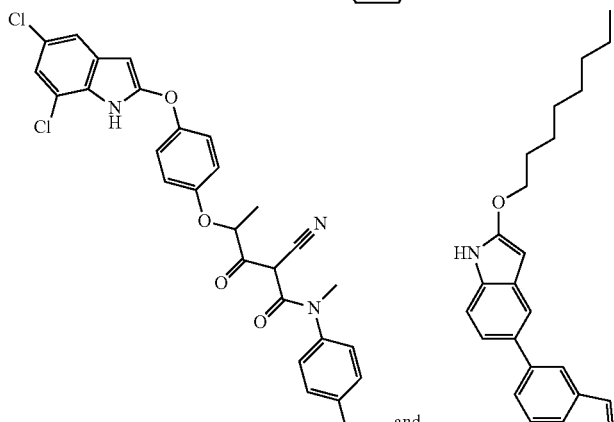

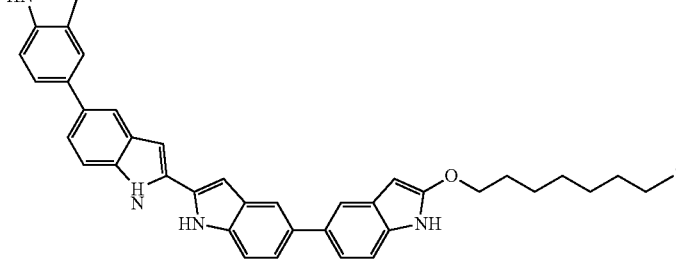

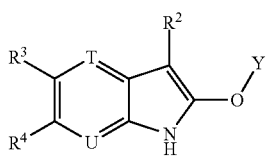

and

[28]
A pharmaceutical composition consisting of a combination of a compound represented by formula (I):

(I)

or its pharmaceutically acceptable salt, and
an insulin secretagogue, a fast-acting insulin secretagogue, a glucose uptake inhibitor, an insulin resistance improving drug, a thiazolidine derivative, an insulin formulation, a peptidyl peptidase IV inhibitor, a GLP-1 receptor agonist, a sodium-dependent glucose transporter 1 inhibitor, or a sodium-dependent glucose transporter 2 inhibitor,
wherein
Y is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;

T is —$CR^7$= or —N=;
U is —$CR^8$= or —N=;
$R^2$ is hydrogen, halogen, cyano, nitro, carboxy, substituted or unsubstituted alkyl, substituted or unsubstituted alkenyl, substituted or unsubstituted acyl, substituted or unsubstituted carbamoyl, substituted or unsubstituted alkylthio, substituted or unsubstituted alkylsulfinyl, substituted or unsubstituted alkylsulfonyl, or substituted or unsubstituted alkyloxycarbonyl;
$R^3$ is halogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;

$R^4$, $R^7$ and $R^8$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino; with the proviso that a compound wherein Y is substituted or unsubstituted alkyl, T is —$CR^7$=, U is —$CR^8$=, and $R^3$ is halogen;

a compound wherein Y is substituted or unsubstituted alkyl, T is —$CR^7$=, U is —$CR^8$=, and $R^2$ is substituted or unsubstituted acyl, or substituted or unsubstituted alkylthio; a compound wherein Y is substituted or unsubstituted alkyl, substituted or unsubstituted alkenyl, or substituted or unsubstituted alkynyl, T is —$CR^7$=, U is —$CR^8$=, and $R^2$ is substituted or unsubstituted alkyloxycarbonyl; and compounds shown below are excluded:

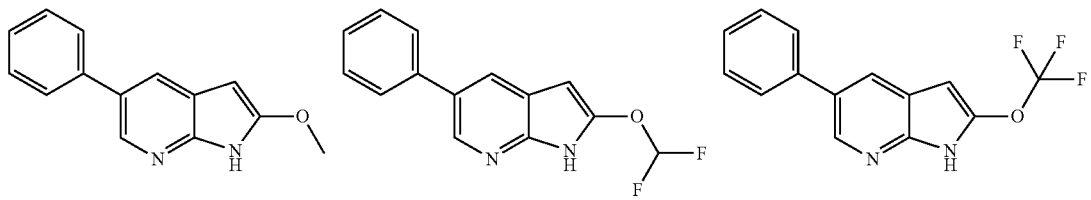

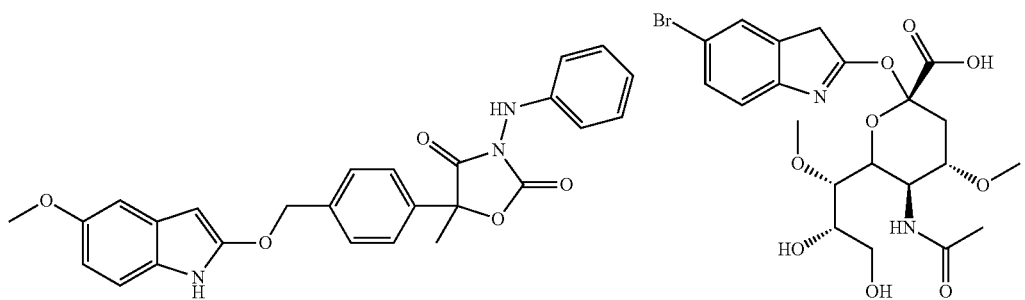

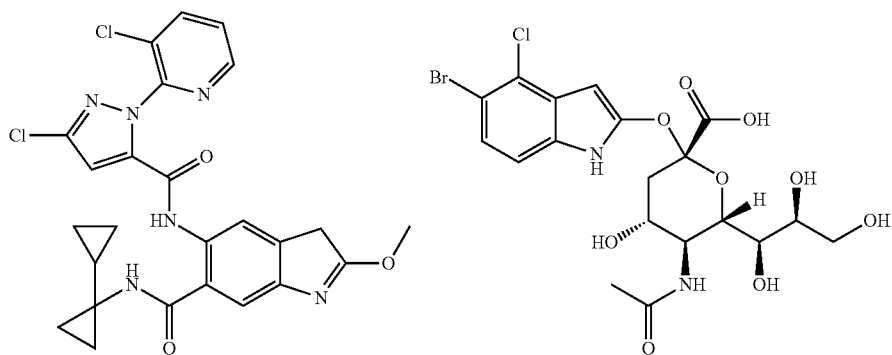

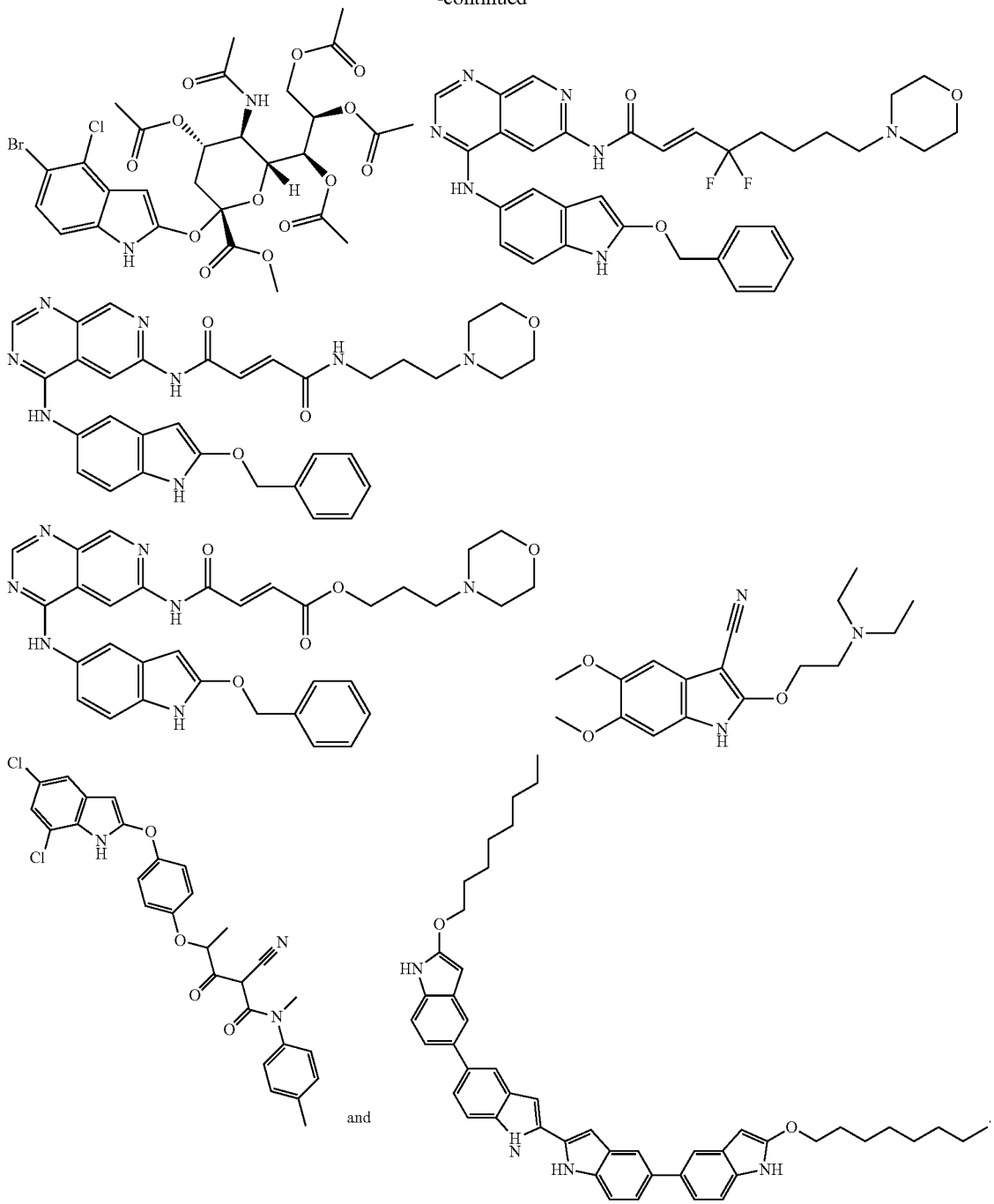

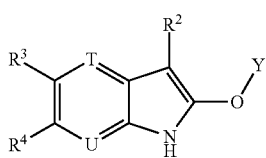

and

[29]

A pharmaceutical composition comprising a compound represented by formula (I):

(I)

or its pharmaceutically acceptable salt, for a combination therapy with an insulin secretagogue, a fast-acting insulin secretagogue, a glucose uptake inhibitor, an insulin resistance improving drug, a thiazolidine derivative, an insulin formulation, a peptidyl peptidase IV inhibitor, a GLP-1 receptor agonist, a sodium-dependent glucose transporter 1 inhibitor, or a sodium-dependent glucose transporter 2 inhibitor, wherein Y is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;

T is —CR$^7$= or —N=;

U is —CR$^8$= or —N=;

R$^2$ is hydrogen, halogen, cyano, nitro, carboxy, substituted or unsubstituted alkyl, substituted or unsubstituted alkenyl, substituted or unsubstituted acyl, substituted or unsubstituted carbamoyl, substituted or unsubstituted alkylthio, substituted or unsubstituted alkylsulfinyl, substituted or unsubstituted alkylsulfonyl, or substituted or unsubstituted alkyloxycarbonyl;

R$^3$ is halogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;

R$^4$, R$^7$ and R$^8$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino; with the proviso that a compound wherein Y is substituted or unsubstituted alkyl, T is —CR$^7$=, U is —CR$^8$=, and R$^3$ is halogen;

a compound wherein Y is substituted or unsubstituted alkyl, T is —CR$^7$=, U is —CR$^8$=, and R$^2$ is substituted or unsubstituted acyl, or substituted or unsubstituted alkylthio; a compound wherein Y is substituted or unsubstituted alkyl, substituted or unsubstituted alkenyl, or substituted or unsubstituted alkynyl, T is —CR$^7$=, U is —CR$^8$=, and R$^2$ is substituted or unsubstituted alkyloxycarbonyl; and compounds shown below are excluded:

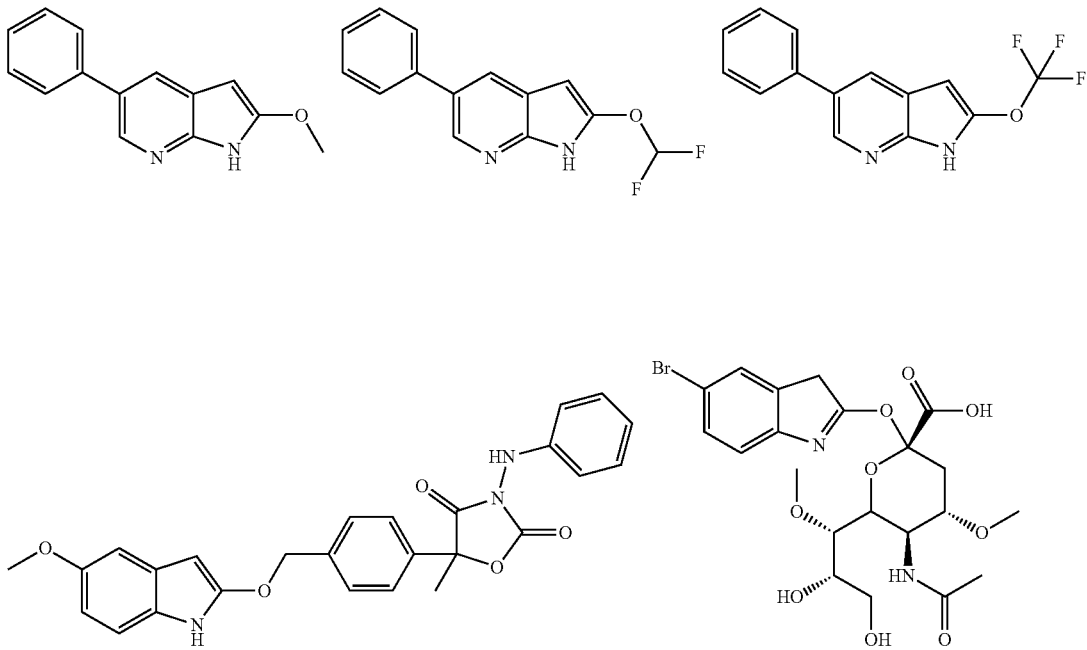

-continued
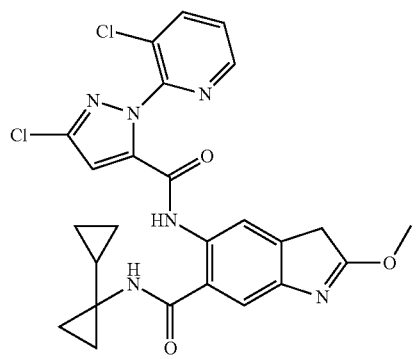
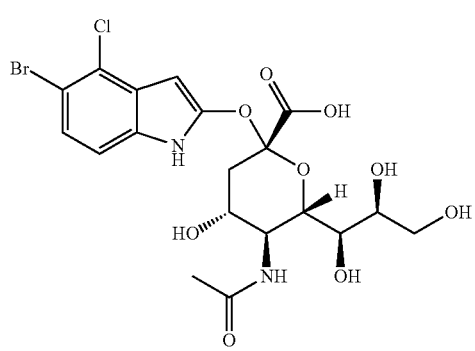
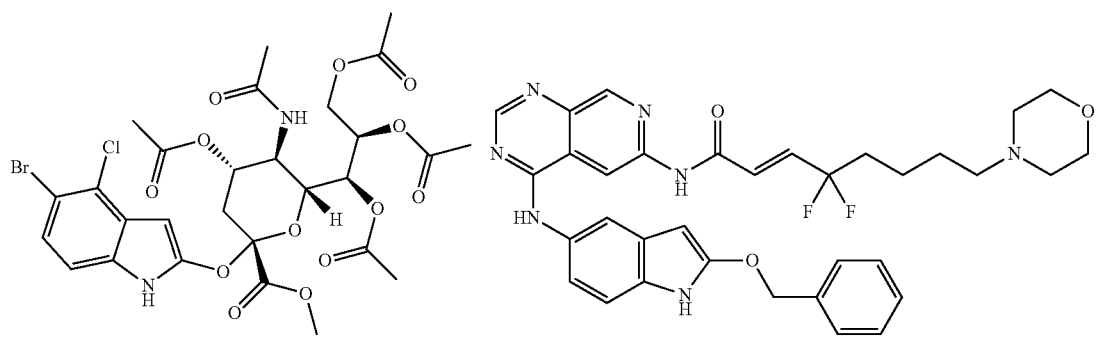
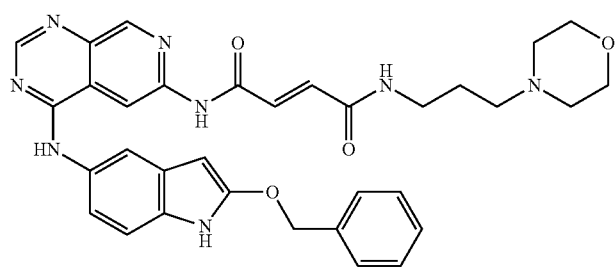
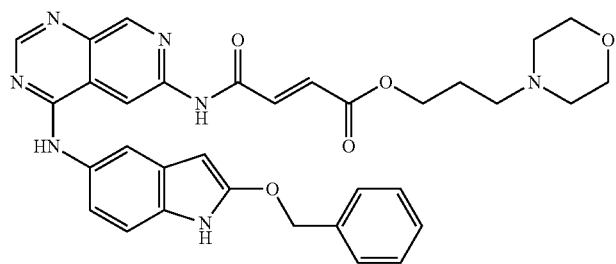

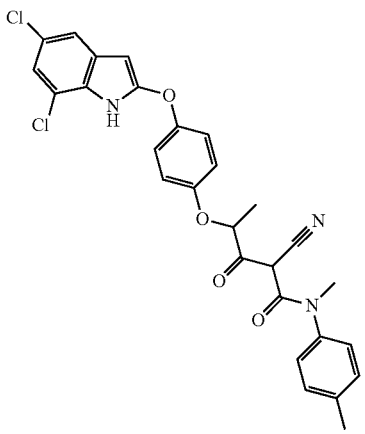

and

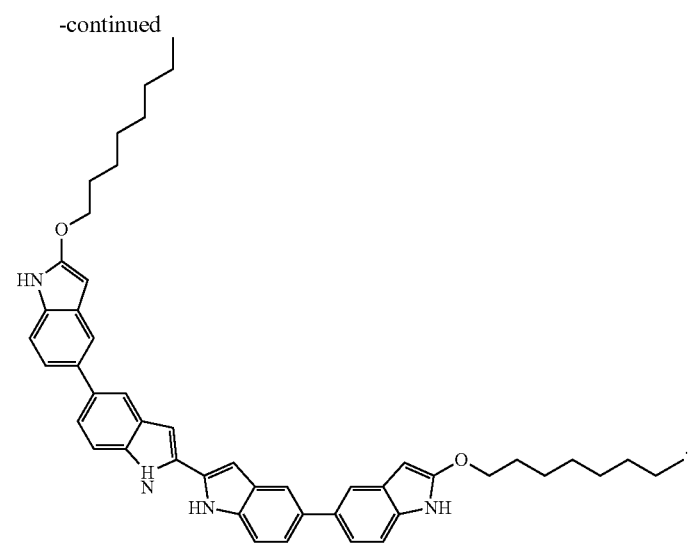

Further, the present invention relates to the following.

[1A]
A compound represented by formula (III):

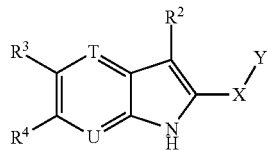

or its pharmaceutically acceptable salt,
wherein
X is —O—, —S—, —NR$^5$—, —C(=O)—, —C(=O)NR$^6$— or —SO$_2$—;
R$^5$ is hydrogen, or substituted or unsubstituted alkyl;
R$^6$ is hydrogen, or substituted or unsubstituted alkyl;
Y is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;
T is —CR$^7$= or —N=;
U is —CR$^8$= or —N=;
R$^2$ is hydrogen, halogen, cyano, nitro, carboxy, substituted or unsubstituted alkyl, substituted or unsubstituted carbamoyl, substituted or unsubstituted alkylthio, substituted or unsubstituted alkylsulfinyl, substituted or unsubstituted alkylsulfonyl, or substituted or unsubstituted alkyloxycarbonyl;
R$^3$ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;
R$^4$, R$^7$ and R$^8$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino; with the proviso that a compound wherein X is —C(=O)—, T is —CR$^7$=, U is —CR$^8$=, and R$^3$ is substituted or unsubstituted alkyl, substituted or unsubstituted alkyloxy, or substituted or unsubstituted acyl;
a compound wherein X is —C(=O)NR$^6$—, T is —CR$^7$=, U is —CR$^8$=, and R$^3$ is substituted or unsubstituted alkyl, substituted or unsubstituted alkyloxy, or substituted or unsubstituted amino; and compounds shown below are excluded:

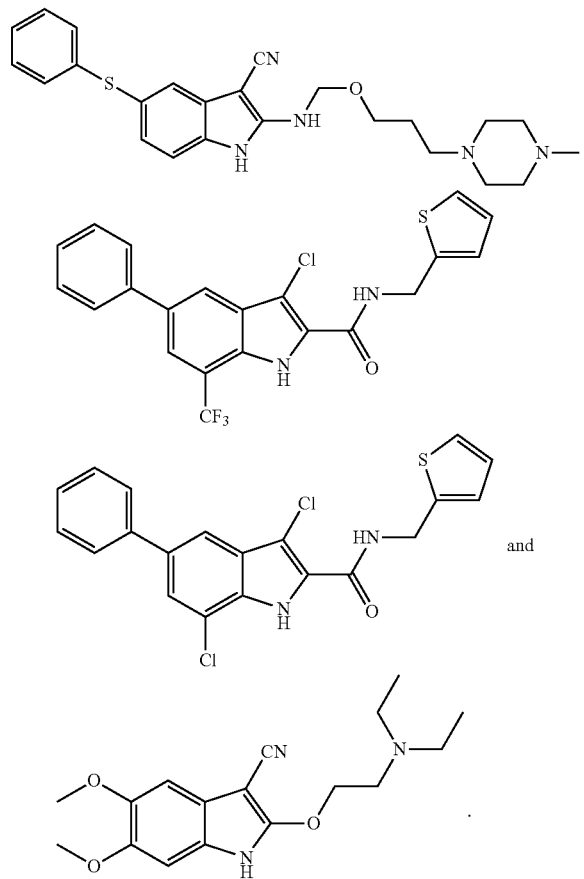

[2A]
The compound according to the above [1A] or its pharmaceutically acceptable salt, wherein $R^2$ is halogen, cyano, carboxy, or substituted or unsubstituted carbamoyl.

[3A]
The compound according to the above [1A] or [2A], or its pharmaceutically acceptable salt, wherein $R^2$ is cyano.

[4A]
The compound according to any one of the above [1A] to [3A] or its pharmaceutically acceptable salt, wherein X is —O—, —S—, or —$NR^5$—.

[5A]
The compound according to any one of the above [1A] to [4A] or its pharmaceutically acceptable salt, wherein X is —O—.

[6A]
The compound according to any one of the above [1A] to [5A] or its pharmaceutically acceptable salt, wherein Y is substituted or unsubstituted aryl, substituted or unsubstituted heteroaryl, substituted or unsubstituted cycloalkyl, substituted or unsubstituted cycloalkenyl, or substituted or unsubstituted heterocyclyl.

[7A]
The compound according to the above [6A] or its pharmaceutically acceptable salt, wherein Y is substituted or unsubstituted aryl, substituted or unsubstituted cycloalkyl, or substituted or unsubstituted heterocyclyl.

[8A]
The compound according to the above [7A] or its pharmaceutically acceptable salt, wherein Y is substituted or unsubstituted heterocyclyl.

[9A]
The compound according to the above [8A] or its pharmaceutically acceptable salt, wherein Y is substituted or unsubstituted heterocyclyl and the substituted or unsubstituted heterocyclyl is

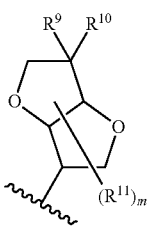

wherein $R^9$ and $R^{10}$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino;

$R^{11}$ is each independently halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino;

m is an integer from 0 to 4.

[10A]
The compound according to any one of the above [1A] to [9A] or its pharmaceutically acceptable salt, wherein $R^3$ is substituted or unsubstituted aryl.

[11A]
The compound according to any one of the above [1A] to [10A] or its pharmaceutically acceptable salt, wherein $R^4$ is halogen.

[12A]
The compound according to any one of the above [1A] to [11A] or its pharmaceutically acceptable salt, wherein T is —$CR^7$=.

[13A]
The compound according to any one of the above [1A] to [11A] or its pharmaceutically acceptable salt, wherein T is —N=.

[14A]
The compound according to any one of the above [1A] to [13A] or its pharmaceutically acceptable salt, wherein U is —$CR^8$=.

[15A]
A pharmaceutical composition having an activating effect on adenosine monophosphate-activated protein kinase, which comprises a compound represented by formula (II):

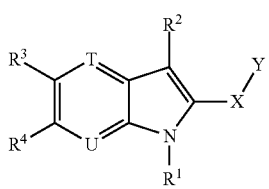

(II)

or its pharmaceutically acceptable salt,
wherein
X is —O—, —S—, —NR$^5$—, —C(=O)—, —C(=O)NR$^6$—, or —SO$_2$—;
R$^5$ is hydrogen, or substituted or unsubstituted alkyl;
R$^6$ is hydrogen, or substituted or unsubstituted alkyl;
Y is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;
T is —CR$^7$= or —N=;
U is —CR$^5$= or —N=;
R$^1$— is hydrogen, substituted or unsubstituted alkyl, or substituted or unsubstituted amino;
R$^2$ is hydrogen, halogen, cyano, nitro, carboxy, substituted or unsubstituted alkyl, substituted or unsubstituted carbamoyl, substituted or unsubstituted alkylthio, substituted or unsubstituted alkylsulfinyl, substituted or unsubstituted alkylsulfonyl, or substituted or unsubstituted alkyloxycarbonyl;
R$^3$ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;
R$^4$, R$^7$ and R$^5$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino.

[16A]
A pharmaceutical composition comprising the compound according to any one of the above [1A] to [14A], or its pharmaceutically acceptable salt.
[17A]
The pharmaceutical composition according to the above [16A], which has an activating effect on adenosine monophosphate-activated protein kinase.
Further, the present invention includes the followings.
[18A]
The pharmaceutical composition according to any one of the above [15A] to [17A], for the treatment and/or prevention of diabetes.
[19A]
A method for preventing or treating diabetes, comprising administering the compound according to any one of the above [RA] to [15A], or its pharmaceutically acceptable salt.
[20A]
The compound according to any one of the above [1A] to [15A], or its pharmaceutically acceptable salt, for the treatment and/or prevention of diabetes.

Effect of the Invention

The compound of the present invention has an AMPK activating effect, and thus a pharmaceutical composition comprising a compound of the present invention is very useful as a medicinal product, particularly, a medicine for treating and/or preventing type II diabetes, hyperglycemia, metabolic syndrome, obesity, hypercholesterolemia and/or hypertension. Further, the compound of the present invention is a compound which has usefulness as a medicine. The usefulness as a medicine herein comprises good metabolic stability, slight induction of a drug-metabolizing enzyme, slight inhibition of drug-metabolizing enzymes which metabolize other drugs, high oral absorption, low clearance, a sufficiently long half-life period to express the efficacy of a medicine, a high enzyme activity, a high maximal activation rate, a low protein binding rate, high penetration into target tissue, high solubility, high safety, an insulin resistance improving effect based on an energy consumption increase, the effect of decreasing hemoglobin A$_{1C}$ (HbA1c), the effect of improving fatty liver or the like.

MODE FOR CARRYING OUT THE INVENTION

Each term used in this description will be described below. In this description, even when each term is used individually or used with other terms, the term has the same meaning.
"Halogen" includes fluorine, chlorine, bromine and iodine.
"Alkyl" means a C1 to C10 straight or branched alkyl group, and example includes methyl, ethyl, n-propyl, isopropyl, n-butyl, isobutyl, sec-butyl, tert-butyl, n-pentyl, isopentyl, neopentyl, n-hexyl, isohexyl, n-heptyl, n-octyl, n-nonyl, n-decyl or the like. Preferable is C1 to C6 or C1 to C4 alkyl, and example includes methyl, ethyl, n-propyl, isopropyl, n-butyl, isobutyl, sec-butyl, tert-butyl, n-pentyl, isopentyl, neopentyl, n-hexyl or isohexyl.

"Alkenyl" means C2 to C8 straight or branched alkenyl having one or more double bond(s) in the above "alkyl", and example includes vinyl, 1-propenyl, 2-propenyl, 1-butenyl, 2-butenyl, 3-butenyl, 1,3-butadienyl, 3-methyl-2-butenyl or the like.

"Alkynyl" means C2 to C8 straight or branched alkynyl having one or more triple bond(s) in the above "alkyl", and example includes ethynyl, propinyl, butynyl or the like. Furthermore, "Alkynyl" may have a double bond.

"Cycloalkyl" means a C3 to C15 cyclic saturated hydrocarbon group, and example includes cyclopropyl, cyclobutyl, cyclopentyl, cyclohexyl, cycloheptyl, cyclooctyl, bridged cyclic hydrocarbon group, Spiro hydrocarbon group or the like. Preferable is cyclopropyl, cyclobutyl, cyclopentyl, cyclohexyl or bridged cyclic hydrocarbon group.

"Bridged cyclic hydrocarbon group" includes a group which is derived by excluding one hydrogen from a C5 to C8 aliphatic cycle which consists of two or more rings that share two or more atoms. Example includes bicyclo[2.1.0]pentyl, bicyclo[2.2.1]heptyl, bicyclo[2.2.2]octyl, bicyclo[3.2.1]octyl, tricyclo[2.2.1.0]heptyl or the like.

"Spiro hydrocarbon group" includes a group which is derived by excluding one hydrogen from a cycle which consists of two hydrocarbon rings that share one carbon atom. Example includes spiro[3.4]octyl or the like.

"Cycloalkenyl" means C3 to C10 cyclic unsaturated aliphatic hydrocarbon group, and example includes cyclopropenyl (e.g.: 1-cyclopropenyl), cyclobutenyl (e.g.: 1-cyclobutenyl), cyclopentenyl (e.g.: 1-cyclopenten-1-yl, 2-cyclopenten-1-yl or 3-cyclopenten-1-yl), cyclohexenyl (e.g.: 1-cyclohexen-1-yl, 2-cyclohexen-1-yl or 3-cyclohexen-1-yl), cycloheptenyl (e.g.: 1-cycloheptenyl), cyclooctenyl (e.g.: 1-cyclooctenyl) or the like. Preferable is cyclopropenyl, cyclobutenyl, cyclopentenyl or cyclohexenyl. Cycloalkenyl also includes bridged cyclic hydrocarbon group and Spiro hydrocarbon group which have an unsaturated bond in the ring.

"Aryl" means a monocyclic aromatic hydrocarbon group (e.g.: phenyl) and a polycyclic aromatic hydrocarbon group (e.g.: 1-naphthyl, 2-naphthyl, 1-anthryl, 2-anthryl, 9-anthryl, 1-phenanthryl, 2-phenanthryl, 3-phenanthryl, 4-phenanthryl or 9-phenanthryl). Preferable is phenyl or naphthyl (1-naphthyl or 2-naphthyl).

"Heteroaryl" means a monocyclic aromatic heterocyclic group and a fused aromatic heterocyclic group.

The "monocyclic aromatic heterocyclic group" means a group which is induced from a 5 to 8-membered aromatic ring which has one or more, the same or different, hetero atoms optionally selected from oxygen, sulfur and nitrogen atoms in the ring, which group may have a bond at any substitutable position.

The "fused aromatic heterocyclic group" means a group in which a 5 to 8-membered aromatic ring which has one or more, the same or different, hetero atoms optionally selected from oxygen, sulfur and nitrogen atoms in the ring is fused with one to four 5 to 8-membered aromatic carbocyclic rings or another 5 to 8-membered aromatic hetero ring, which group may have a bond at any substitutable position.

Example of the "heteroaryl" includes furyl (e.g.: 2-furyl or 3-furyl), thienyl (e.g.: 2-thienyl or 3-thienyl), pyrrolyl (e.g.: 1-pyrrolyl, 2-pyrrolyl or 3-pyrrolyl), imidazolyl (e.g.: 1-imidazolyl, 2-imidazolyl or 4-imidazolyl), pyrazolyl (e.g.: 1-pyrazolyl, 3-pyrazolyl or 4-pyrazolyl), triazolyl (e.g.: 1,2,4-triazole-1-yl, 1,2,4-triazole-3-yl or 1,2,4-triazole-4-yl), tetrazolyl (e.g.: 1-tetrazolyl, 2-tetrazolyl or 5-tetrazolyl), oxazolyl (e.g.: 2-oxazolyl, 4-oxazolyl or 5-oxazolyl), isoxazolyl (e.g.: 3-isoxazolyl, 4-isoxazolyl or 5-isoxazolyl), thiazolyl (e.g.: 2-thiazolyl, 4-thiazolyl or 5-thiazolyl), thiadiazolyl, isothiazolyl (e.g.: 3-isothiazolyl, 4-isothiazolyl or 5-isothiazolyl), pyridyl (e.g.: 2-pyridyl, 3-pyridyl or 4-pyridyl), pyridazinyl (e.g.: 3-pyridazinyl or 4-pyridazinyl), pyrimidinyl (e.g.: 2-pyrimidinyl, 4-pyrimidinyl or 5-pyrimidinyl), furazanyl (e.g.: 3-furazanyl), pyrazinyl (e.g.: 2-pyrazinyl), oxadiazolyl (e.g.: 1,3,4-oxadiazole-2-yl), benzofuryl (e.g.: 2-benzo[b]furyl, 3-benzo[b]furyl, 4-benzo[b]furyl, 5-benzo[b]furyl, 6-benzo[b]furyl or 7-benzo[b]furyl), benzothienyl (e.g.: 2-benzo[b]thienyl, 3-benzo[b]thienyl, 4-benzo[b]thienyl, 5-benzo[b]thienyl, 6-benzo[b]thienyl or 7-benzo[b]thienyl), benzimidazolyl (e.g.: 1-benzimidazolyl, 2-benzimidazolyl, 4-benzimidazolyl or 5-benzimidazolyl), dibenzofuryl, benzoxazolyl, benzothiazolyl, quinoxalinyl (e.g.: 2-quinoxalinyl, 5-quinoxalinyl or 6-quinoxalinyl), cinnolinyl (e.g.: 3-cinnolinyl, 4-cinnolinyl, 5-cinnolinyl, 6-cinnolinyl, 7-cinnolinyl or 8-cinnolinyl), quinazolinyl (e.g.: 2-quinazolinyl, 4-quinazolinyl, 5-quinazolinyl, 6-quinazolinyl, 7-quinazolinyl or 8-quinazolinyl), quinolyl (e.g.: 2-quinolyl, 3-quinolyl, 4-quinolyl, 5-quinolyl, 6-quinolyl, 7-quinolyl or 8-quinolyl), phthalazinyl (e.g.: 1-phthalazinyl, 5-phthalazinyl or 6-phthalazinyl), isoquinolyl (e.g.: 1-isoquinolyl, 3-isoquinolyl, 4-isoquinolyl, 5-isoquinolyl, 6-isoquinolyl, 7-isoquinolyl or 8-isoquinolyl), puryl, pteridinyl (e.g.: 2-pteridinyl, 4-pteridinyl, 6-pteridinyl or 7-pteridinyl), carbazolyl, phenanthridinyl, acridinyl (e.g.: 1-acridinyl, 2-acridinyl, 3-acridinyl, 4-acridinyl or 9-acridinyl), indolyl (e.g.: 1-indolyl, 2-indolyl, 3-indolyl, 4-indolyl, 5-indolyl, 6-indolyl or 7-indolyl), isoindolyl, phenadinyl (e.g.: 1-phenadinyl or 2-phenadinyl), phenothiadinyl (e.g.: 1-phenothiadinyl, 2-phenothiadinyl, 3-phenothiadinyl or 4-phenothiadinyl) or the like.

"Heterocyclyl" means a non aromatic heterocyclic group, which may have a bond at any substitutable position of a ring which has at least one or more nitrogen, oxygen or sulfur atoms in the ring, or a ring in which such ring is fused with a cycloalkane (preferably 5 to 6-membered), a benzene ring and/or a ring which has at least one or more nitrogen, oxygen or sulfur atoms in the ring. "Nonaromatic heterocyclic group" can be saturated or unsaturated as long as it is non-aromatic. Preferable is a 5- to 8-membered ring. Example includes 1-pyrrolinyl, 2-pyrrolinyl, 3-pyrrolinyl, 1-pyrrolidinyl, 2-pyrrolidinyl, 3-pyrrolidinyl, 1-imidazolinyl, 2-imidazolinyl, 4-imidazolinyl, 1-imidazolidinyl, 2-imidazolidinyl, 4-imidazolidinyl, 1-pyrazolinyl, 3-pyrazolinyl, 4-pyrazolinyl, 1-pyrazolidinyl, 3-pyrazolidinyl, 4-pyrazolidinyl, piperidino, 2-piperidinyl, 3-piperidinyl, 4-piperidinyl, 1-piperadinyl, 2-piperadinyl, 2-morpholinyl, 3-morpholinyl, morpholino, tetrahydropyranyl, tetrahydrofuranyl, 1,2,3,4-tetrahydroisoquinolinyl, 1,2,3,4-tetrahydroquinolinyl, 1,3-dihydro-2H-isoindol-5-yl, the following group or the like

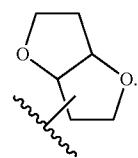

"Heterocyclyl" further contains a bridged group or a Spiro ring forming group shown below.

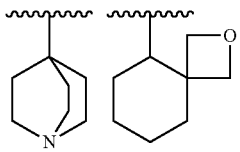

"Acyl" means formyl, substituted or unsubstituted alkylcarbonyl, substituted or unsubstituted alkenylcarbonyl, substituted or unsubstituted cycloalkylcarbonyl, substituted or unsubstituted cycloalkenylcarbonyl, substituted or unsubstituted arylcarbonyl, substituted or unsubstituted heteroarylcarbonyl or substituted or unsubstituted heterocyclylcarbonyl.

The alkyl part of "alkylcarbonyl", the alkenyl part of "alkenylcarbonyl", the cycloalkyl part of "cycloalkylcarbonyl", the cycloalkenyl part of "cycloalkenylcarbonyl", the aryl part of "arylcarbonyl", the heteroaryl part of "heteroarylcarbonyl" and the heterocyclyl part of "heterocyclylcarbonyl" respectively mean the above "alkyl", the above "alkenyl", the above "cycloalkyl", the above "cycloalkenyl", the above "aryl", the above "heteroaryl" and the above "heterocyclyl".

The alkyl part of "alkyloxy", "alkylthio" and "alkylsulfonyl" means the above "alkyl".

The aryl part of "aryloxy", "arylthio" and "arylsulfonyl" means the above "aryl".

The heteroaryl part of "heteroaryloxy", "heteroarylthio" and "heteroarylsulfonyl" means the above "heteroaryl".

The cycloalkyl part of "cycloalkyloxy", "cycloalkylthio" and "cycloalkylsulfonyl" means the above "cycloalkyl".

The cycloalkenyl part of "cycloalkenyloxy", "cycloalkenylthio" and "cycloalkenylsulfonyl" means the above "cycloalkenyl".

The heterocyclyl part of "heterocyclyloxy", "heterocyclylthio" and "heterocyclylsulfonyl" means the above "heterocyclyl".

Examples of substituents of "substituted alkyl", "substituted alkenyl", "substituted alkynyl", "substituted aryl", "substituted heteroaryl", "substituted cycloalkyl", "substituted cycloalkenyl", "substituted heterocyclyl", "substituted alkyloxy", "substituted aryloxy", "substituted heteroaryloxy", "substituted cycloalkyloxy", "substituted cycloalkenyloxy", "substituted heterocyclyloxy", "substituted alkylthio", "substituted arylthio", "substituted heteroarylthio", "substituted cycloalkylthio", "substituted cycloalkenylthio", "substituted heterocyclylthio", "substituted alkylsulfonyl", "substituted arylsulfonyl", "substituted heteroarylsulfonyl", "substituted cycloalkylsulfonyl", "substituted cycloalkenylsulfonyl", "substituted heterocyclylsulfonyl", "substituted acyl", "substituted alkylsulfinyl", or "substituted alkyloxycarbonyl", include groups selected from the group consisting of halogen; hydroxy; carboxy; nitro; cyano;

substituted or unsubstituted alkyl (an example of a substituent of substituted alkyl includes halogen, hydroxy, carboxy, nitro, cyano, alkyl, aryl, cycloalkyl, cycloalkenyl, heteroaryl, heterocyclyl or substituted or unsubstituted amino (an example of a substituent of substituted amino includes alkylcarbonyl). e.g. methyl, ethyl, isopropyl, tert-butyl or $CF_3$);

substituted or unsubstituted alkenyl (an example of a substituent of substituted alkenyl includes halogen, hydroxy, carboxy, nitro, cyano, alkyl, aryl, cycloalkyl, cycloalkenyl, heteroaryl, heterocyclyl or substituted or unsubstituted amino (an example of a substituent of substituted amino includes alkylcarbonyl). e.g. vinyl);

substituted or unsubstituted alkynyl (an example of a substituent of substituted alkynyl includes halogen, hydroxy, carboxy, nitro, cyano, alkyl, aryl, cycloalkyl, cycloalkenyl, heteroaryl or heterocyclyl. e.g. ethynyl);

substituted or unsubstituted aryl (an example of a substituent of substituted aryl includes halogen, hydroxy, carboxy, nitro, cyano, alkyl, aryl, cycloalkyl, cycloalkenyl, substituted or unsubstituted heteroaryl (an example of a substituent of substituted heteroaryl includes $CH_2C(CH_3)_2OH$) or heterocyclyl. e.g. phenyl or naphthyl);

substituted or unsubstituted cycloalkyl (an example of a substituent of substituted cycloalkyl includes halogen, hydroxy, carboxy, nitro, cyano, alkyl, aryl, cycloalkyl, cycloalkenyl, heteroaryl or heterocyclyl. e.g. cyclopropyl or cyclobutyl);

substituted or unsubstituted cycloalkenyl (an example of a substituent of substituted cycloalkenyl includes halogen, hydroxy, carboxy, nitro, cyano, alkyl, aryl, cycloalkyl, cycloalkenyl, heteroaryl, heterocyclyl or substituted or unsubstituted amino (an example of a substituent of substituted amino includes acyl or alkylsulfonyl). e.g. cyclopropenyl);

substituted or unsubstituted heteroaryl (an example of a substituent of substituted heteroaryl includes halogen, hydroxy, carboxy, nitro, cyano, substituted or unsubstituted alkyl (an example of a substituent of substituted alkyl includes hydroxy, carboxy or alkyloxycarbonyl), aryl, cycloalkyl, cycloalkenyl, heteroaryl or heterocyclyl);

substituted or unsubstituted heterocyclyl (an example of a substituent of substituted heterocyclyl includes halogen, hydroxy, carboxy, nitro, cyano, alkyl, aryl, cycloalkyl, cycloalkenyl, heteroaryl, heterocyclyl, substituted or unsubstituted acyl (an example of a substituent of substituted acyl includes hydroxy) or alkylsulfonyl. e.g. morpholinyl, piperidyl or pyrrolidinyl);

substituted or unsubstituted alkyloxy (an example of a substituent of substituted alkyloxy includes halogen, hydroxy, carboxy, nitro, cyano, alkyl, aryl, cycloalkyl, cycloalkenyl, heteroaryl or heterocyclyl. e.g. methoxy or ethoxy);

substituted or unsubstituted alkenyloxy (an example of a substituent of substituted alkenyloxy includes halogen, hydroxy, carboxy, nitro, cyano, alkyl, aryl, cycloalkyl, cycloalkenyl, heteroaryl or heterocyclyl. e.g. vinyloxy or allyloxy);

substituted or unsubstituted aryloxy (an example of a substituent of substituted aryloxy includes halogen, hydroxy, carboxy, nitro, cyano, alkyl, aryl, cycloalkyl, cycloalkenyl, heteroaryl or heterocyclyl. e.g. phenyloxy);

substituted or unsubstituted cycloalkyloxy (an example of a substituent of substituted cycloalkyloxy includes halogen, hydroxy, carboxy, nitro, cyano, alkyl, aryl, cycloalkyl, cycloalkenyl, heteroaryl or heterocyclyl);

substituted or unsubstituted cycloalkenyloxy (an example of a substituent of substituted cycloalkenyloxy includes halogen, hydroxy, carboxy, nitro, cyano, alkyl, aryl, cycloalkyl, cycloalkenyl, heteroaryl or heterocyclyl);

substituted or unsubstituted heteroaryloxy (an example of a substituent of substituted heteroaryloxy includes halogen, hydroxy, carboxy, nitro, cyano, alkyl, aryl, cycloalkenyl, heteroaryl or heterocyclyl);

substituted or unsubstituted heterocyclyloxy (an example of a substituent of substituted heterocyclyloxy includes halogen, hydroxy, carboxy, nitro, cyano, alkyl, aryl, cycloalkyl, cycloalkenyl, heteroaryl or heterocyclyl);

substituted or unsubstituted arylalkyl (an example of a substituent of substituted arylalkyl includes halogen, hydroxy, carboxy, nitro, cyano, alkyl, aryl, cycloalkyl, cycloalkenyl, heteroaryl or heterocyclyl. e.g. benzyl);

substituted or unsubstituted silyloxy;

substituted or unsubstituted amino (e.g. alkylamino (e.g. methylamino, ethylamino or dimethylamino), arylamino, cycloalkylamino, cycloalkenylamino, heteroarylamino, heterocyclylamino, acylamino (e.g. acetylamino, benzoylamino), arylalkylamino (e.g. benzylamino or tritylamino), hydroxyamino, alkyloxycarbonylamino, carbamoylamino, alkylsulfonylamino, arylsulfonylamino, cycloalkylsulfonylamino, cycloalkenylsulfonylamino, heteroarylsulfonylamino or heterocyclylsulfonylamino);

substituted or unsubstituted carbamoyl (an example of a substituent of substituted carbamoyl includes halogen, hydroxy, carboxy, nitro, cyano, alkyl, aryl, cycloalkyl, cycloalkenyl, heteroaryl or heterocyclyl. e.g. alkylcarbamoyl (e.g. methylcarbamoyl, ethylcarbamoyl, dimethylcarbamoyl, phenylethylcarbamoyl, dimethylaminoethylcarbamoyl, isopropylcarbamoyl or hydroxyethylcarbamoyl), alkylsulfonylcarbamoyl, heteroarylalkylcarbamoyl or alkyloxycarbamoyl);

substituted or unsubstituted carbamoyloxy (an example of a substituent of substituted carbamoyloxy includes halogen, alkyl, aryl, cycloalkyl, cycloalkenyl, heteroaryl or heterocyclyl);

substituted or unsubstituted acyl (an example of a substituent of substituted acyl includes halogen, hydroxy, carboxy, nitro, cyano, alkyl, aryl, cycloalkyl, cycloalkenyl, heteroaryl or heterocyclyl. e.g. alkylcarbonyl, arylcarbonyl, cycloalkylcarbonyl, cycloalkenylcarbonyl, heteroarylcarbonyl, heterocyclylcarbonyl, formyl or acetyl);

substituted or unsubstituted alkylsulfonyl (an example of a substituent of substituted alkylsulfonyl includes halogen, hydroxy, carboxy, nitro, cyano, alkyl, aryl, cycloalkyl, cycloalkenyl, heteroaryl or heterocyclyl. e.g. methanesulfonyl or ethanesulfonyl);

substituted or unsubstituted arylsulfonyl (an example of a substituent of substituted arylsulfonyl includes halogen, hydroxy, carboxy, nitro, cyano, alkyl, aryl, cycloalkyl, cycloalkenyl, heteroaryl or heterocyclyl);

substituted or unsubstituted cycloalkylsulfonyl (an example of a substituent of substituted cycloalkylsulfonyl includes halogen, hydroxy, carboxy, nitro, cyano, alkyl, aryl, cycloalkyl, cycloalkenyl, heteroaryl or heterocyclyl);

substituted or unsubstituted cycloalkenylsulfonyl (an example of a substituent of substituted cycloalkenylsulfonyl includes halogen, hydroxy, carboxy, nitro, cyano, alkyl, aryl, cycloalkyl, cycloalkenyl, heteroaryl or heterocyclyl);

substituted or unsubstituted heteroarylsulfonyl (an example of a substituent of substituted heteroarylsulfonyl includes halogen, hydroxy, carboxy, nitro, cyano, alkyl, aryl, cycloalkyl, cycloalkenyl, heteroaryl or heterocyclyl);

substituted or unsubstituted heterocyclylsulfonyl (an example of a substituent of substituted heterocyclylsulfonyl includes halogen, hydroxy, carboxy, nitro, cyano, alkyl, aryl, cycloalkyl, cycloalkenyl, heteroaryl or heterocyclyl);

substituted or unsubstituted alkylthio (an example of a substituent of substituted alkylthio includes halogen, hydroxy, carboxy, nitro, cyano, alkyl, aryl, cycloalkyl, cycloalkenyl, heteroaryl or heterocyclyl);

substituted or unsubstituted arylthio (an example of a substituent of substituted arylthio includes halogen, hydroxy, carboxy, nitro, cyano, alkyl, aryl, cycloalkyl, cycloalkenyl, heteroaryl or heterocyclyl);

substituted or unsubstituted cycloalkylthio (an example of a substituent of substituted cycloalkylthio includes halogen, hydroxy, carboxy, nitro, cyano, alkyl, aryl, cycloalkyl, cycloalkenyl, heteroaryl or heterocyclyl);

substituted or unsubstituted cycloalkenylthio (an example of a substituent of substituted cycloalkenylthio includes halogen, hydroxy, carboxy, nitro, cyano, alkyl, aryl, cycloalkyl, cycloalkenyl, heteroaryl or heterocyclyl);

substituted or unsubstituted heteroarylthio (an example of a substituent of substituted heteroarylthio includes halogen, hydroxy, carboxy, nitro, cyano, alkyl, aryl, cycloalkyl, cycloalkenyl, heteroaryl or heterocyclyl);

substituted or unsubstituted heterocyclylthio (an example of a substituent of substituted heterocyclylthio includes halogen, hydroxy, carboxy, nitro, cyano, alkyl, aryl, cycloalkyl, cycloalkenyl, heteroaryl or heterocyclyl);

substituted or unsubstituted sulfamoyl (an example of a substituent of substituted sulfamoyl includes halogen, alkyl, aryl, cycloalkyl, cycloalkenyl, heteroaryl or heterocyclyl);

substituted or unsubstituted alkyloxycarbonyl (an example of a substituent of substituted alkyloxycarbonyl includes halogen, hydroxy, carboxy, nitro, cyano, alkyl, aryl, cycloalkyl, cycloalkenyl, heteroaryl or heterocyclyl. e.g. methoxycarbonyl, ethoxycarbonyl or tert-butoxycarbonyl);

aryloxycarbonyl; cycloalkyloxycarbonyl; cycloalkenyloxycarbonyl; heteroaryloxycarbonyl; heterocyclyloxycarbonyl; alkylsulfinyl; arylsulfinyl; cycloalkylsulfinyl; cycloalkenylsulfinyl; heteroarylsulfinyl; heterocyclylsulfinyl; nitroso;

substituted or unsubstituted alkylidene (an example of a substituent of substituted alkylidene includes halogen, hydroxy, carboxy, nitro, cyano, alkyl, aryl, cycloalkyl, cycloalkenyl, heteroaryl or heterocyclyl);

azido;

isocyano; isocyanato; thiocyanato; isothiocyanato; mercapto;

formyloxy; haloformyl; oxalo; thioformyl; thiocarboxy; dithiocarboxy; thiocarbamoyl; sulfino; sulfo; sulfoamino; hydrazino; ureido; amidino; guanidino; phthalimido; oxo and the like.

The above substituted groups can be substituted with one to four substituents.

Preferred examples of substituents of "substituted carbamoyl", "substituted sulfamoyl" or "substituted amino" include substituted or unsubstituted alkyl (an example of a substituent of substituted alkyl includes halogen, hydroxy, carboxy, nitro, cyano, alkyl, aryl, cycloalkyl, cycloalkenyl, heteroaryl or heterocyclyl. e.g. methyl, ethyl, isopropyl, tert-butyl or $CF_3$);

substituted or unsubstituted alkenyl (an example of a substituent of substituted alkenyl includes halogen, hydroxy, carboxy, nitro, cyano, alkyl, aryl, cycloalkyl, cycloalkenyl, heteroaryl or heterocyclyl. e.g. vinyl);

substituted or unsubstituted aryl (an example of a substituent of substituted aryl includes halogen, hydroxy, carboxy, nitro, cyano, alkyl, aryl, cycloalkyl, cycloalkenyl, heteroaryl or heterocyclyl. e.g. phenyl or naphthyl);

substituted or unsubstituted cycloalkyl (an example of a substituent of substituted cycloalkyl includes halogen, hydroxy, carboxy, nitro, cyano, alkyl, aryl, cycloalkyl, cycloalkenyl, heteroaryl or heterocyclyl. e.g. cyclopropyl or cyclobutyl);

substituted or unsubstituted cycloalkenyl (an example of a substituent of substituted cycloalkenyl includes halogen, hydroxy, carboxy, nitro, cyano, alkyl, aryl, cycloalkyl, cycloalkenyl, heteroaryl or heterocyclyl. e.g. cyclopropenyl);

substituted or unsubstituted heteroaryl (an example of a substituent of substituted heteroaryl includes halogen, hydroxy, carboxy, nitro, cyano, alkyl, aryl, cycloalkyl, cycloalkenyl, heteroaryl or heterocyclyl);

substituted or unsubstituted heterocyclyl (an example of a substituent of substituted heterocyclyl includes halogen, hydroxy, carboxy, nitro, cyano, alkyl, aryl, cycloalkyl, cycloalkenyl, heteroaryl or heterocyclyl);

substituted or unsubstituted arylalkyl (an example of a substituent of substituted arylalkyl includes halogen, hydroxy, carboxy, nitro, cyano, alkyl, aryl, cycloalkyl, cycloalkenyl, heteroaryl or heterocyclyl);

substituted or unsubstituted alkyloxy (an example of a substituent of substituted alkyloxy includes halogen, hydroxy, carboxy, nitro, cyano, alkyl, aryl, cycloalkyl, cycloalkenyl, heteroaryl or heterocyclyl. e.g. methoxy or ethoxy);

substituted or unsubstituted aryloxy (an example of a substituent of substituted aryloxy includes halogen, hydroxy, carboxy, nitro, cyano, alkyl, aryl, cycloalkyl, cycloalkenyl, heteroaryl or heterocyclyl. e.g. phenyloxy);

substituted or unsubstituted cycloalkyloxy (an example of a substituent of substituted cycloalkyloxy includes halogen, hydroxy, carboxy, nitro, cyano, alkyl, aryl, cycloalkyl, cycloalkenyl, heteroaryl or heterocyclyl);

substituted or unsubstituted cycloalkenyloxy (an example of a substituent of substituted cycloalkenyloxy includes halogen, hydroxy, carboxy, nitro, cyano, alkyl, aryl, cycloalkyl, cycloalkenyl, heteroaryl or heterocyclyl);

substituted or unsubstituted heteroaryloxy (an example of a substituent of substituted heteroaryloxy includes halogen, hydroxy, carboxy, nitro, cyano, alkyl, aryl, cycloalkyl, cycloalkenyl, heteroaryl or heterocyclyl);

substituted or unsubstituted heterocyclyloxy (an example of a substituent of substituted heterocyclyloxy includes halogen, hydroxy, carboxy, nitro, cyano, alkyl, aryl, cycloalkyl, cycloalkenyl, heteroaryl or heterocyclyl);

substituted or unsubstituted acyl (an example of a substituent of substituted acyl includes halogen, hydroxy, carboxy, nitro, cyano, alkyl, aryl, cycloalkyl, cycloalkenyl, heteroaryl or heterocyclyl);

substituted or unsubstituted alkyloxycarbonyl (an example of a substituent of substituted alkyloxycarbonyl includes halogen, hydroxy, carboxy, nitro, cyano, alkyl, aryl, cycloalkyl, cycloalkenyl, heteroaryl or heterocyclyl. e.g. methoxycarbonyl, ethoxycarbonyl or tert-butoxycarbonyl);

aryloxycarbonyl; cycloalkyloxycarbonyl; cycloalkenyloxycarbonyl; heteroaryloxycarbonyl; heterocyclyloxycarbonyl;

substituted or unsubstituted sulfamoyl (an example of a substituent of substituted sulfamoyl includes halogen, hydroxy, carboxy, nitro, cyano, alkyl, aryl, cycloalkyl, cycloalkenyl, heteroaryl or heterocyclyl);

substituted or unsubstituted alkylsulfonyl (an example of a substituent of substituted alkylsulfonyl includes halogen, hydroxy, carboxy, nitro, cyano, alkyl, aryl, cycloalkyl, cycloalkenyl, heteroaryl or heterocyclyl. e.g. methanesulfonyl or ethanesulfonyl);

substituted or unsubstituted arylsulfonyl (an example of a substituent of substituted arylsulfonyl includes halogen, hydroxy, carboxy, nitro, cyano, alkyl, aryl, cycloalkyl, cycloalkenyl, heteroary or heterocyclyl);

substituted or unsubstituted heteroarylsulfonyl (an example of a substituent of substituted heteroarylsulfonyl includes halogen, hydroxy, carboxy, nitro, cyano, alkyl, aryl, cycloalkyl, cycloalkenyl, heteroaryl or heterocyclyl);

substituted or unsubstituted cycloalkylsulfonyl (an example of a substituent of substituted cycloalkylsulfonyl includes halogen, hydroxy, carboxy, nitro, cyano, alkyl, aryl, cycloalkyl, cycloalkenyl, heteroaryl or heterocyclyl);

substituted or unsubstituted cycloalkenylsulfonyl (an example of a substituent of substituted cycloalkenylsulfonyl includes halogen, hydroxy, carboxy, nitro, cyano, alkyl, aryl, cycloalkyl, cycloalkenyl, heteroaryl or heterocyclyl);

substituted or unsubstituted heterocyclylsulfonyl (an example of a substituent of substituted heterocyclylsulfonyl includes halogen, hydroxy, carboxy, nitro, cyano, alkyl, aryl, cycloalkyl, cycloalkenyl, heteroaryl or heterocyclyl);

substituted or unsubstituted carbamoyl (an example of a substituent of substituted carbamoyl includes halogen, hydroxy, carboxy, nitro, cyano, alkyl, aryl, cycloalkyl, cycloalkenyl, heteroaryl or heterocyclyl);

halogen; hydroxy; carboxy; nitro; cyano; alkylsulfinyl; cycloalkylsulfinyl; cycloalkenylsulfinyl; arylsulfinyl; heteroarylsulfinyl; heterocyclylsulfinyl; amino and the like.

The alkyl part of "alkylamino", "arylalkylamino", "alkyloxycarbonylamino", "alkylsulfonylamino", "alkylcarbamoyl", "alkylsulfonylcarbamoyl", "heteroarylalkylcarbamoyl", "alkyloxycarbamoyl", "alkyloxycarbonyl" and "alkylsulfinyl" means the above-described "alkyl".

The alkenyl part of "alkenyloxy" means the above-described "alkenyl".

The aryl part of "arylalkyl", "arylamino", "arylalkylamino", "arylsulfonylamino", "aryloxycarbonyl" and "arylsulfinyl" means the above-described "aryl".

The heteroaryl part of "heteroarylamino", "heteroarylsulfonylamino", "heteroarylalkylcarbamoyl", "heteroaryloxycarbonyl" and "heteroarylsulfinyl" means the above-described "heteroaryl".

The cycloalkyl part of "cycloalkylamino", "cycloalkylsulfonylamino", "cycloalkyloxycarbonyl" and "cycloalkylsulfinyl" means the above-described "cycloalkyl".

The cycloalkenyl part of "cycloalkenylamino", "cycloalkenylsulfonylamino", "cycloalkenyloxycarbonyl" and "cycloalkenylsulfinyl" means the above-described "cycloalkenyl".

The heterocyclyl part of "heterocyclylamino", "heterocyclylsulfonylamino", "heterocyclyloxycarbonyl" and "heterocyclylsulfinyl" means the above-described "heterocyclyl".

Among the compounds of the present invention, the compounds in the following embodiment are preferred.

X is —O—, —S—, —NR$^5$—, —C(=O)—, —C(=O)NR$^6$— or —SO$_2$—, and preferably —O—, —S— or —NR$^5$—. Further preferably, X is —O—.

R$^5$ is hydrogen or substituted or unsubstituted alkyl, and preferably substituted or unsubstituted alkyl.

R$^6$ is hydrogen, or substituted or unsubstituted alkyl, and preferably hydrogen.

Y is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl.

Preferably, Y is substituted or unsubstituted aryl, substituted or unsubstituted heteroaryl, substituted or unsubstituted cycloalkyl, substituted or unsubstituted cycloalkenyl, or substituted or unsubstituted heterocyclyl.

Further preferably, Y is substituted or unsubstituted heterocyclyl.

When Y is substituted or unsubstituted heterocyclyl, the substituted or unsubstituted heterocyclyl is preferably

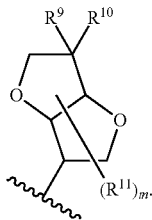

$R^9$ and $R^{10}$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino.

Preferably, one of $R^9$ and $R^{10}$ is hydroxy, and the other is hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino.

Further preferably, one of $R^9$ and $R^{10}$ is hydroxyl, and the other is hydrogen, or substituted or unsubstituted alkyl.

$R^{11}$ is each independently halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino.

m is an integer of 0 to 7, and preferably an integer of 0 to 4. Further preferably, m is 0 or 1.

T is —$CR^7$═ or —N═, and preferably —N═.

U is —$CR^8$═ or —N═, and preferably —$CR^8$═.

$R^1$ is hydrogen, substituted or unsubstituted alkyl, or substituted or unsubstituted amino, and preferably hydrogen, or substituted or unsubstituted alkyl. Further preferably, $R^1$ is hydrogen.

$R^2$ is hydrogen, halogen, cyano, nitro, carboxy, substituted or unsubstituted alkyl, substituted or unsubstituted alkenyl, substituted or unsubstituted acyl, substituted or unsubstituted carbamoyl, substituted or unsubstituted alkylthio, substituted or unsubstituted alkylsulfinyl, substituted or unsubstituted alkylsulfonyl, or substituted or unsubstituted alkyloxycarbonyl. Preferably, $R^2$ is hydrogen, halogen or cyano. Further preferably, $R^2$ is hydrogen or cyano.

$R^3$ is halogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino.

Preferably, $R^3$ is substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, or substituted or unsubstituted amino.

Further preferably, $R^3$ is substituted or unsubstituted aryl, substituted or unsubstituted heteroaryl, or substituted or unsubstituted alkyloxy.

Particularly preferred, $R^3$ is substituted or unsubstituted aryl.

$R^4$, $R^7$ and $R^8$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino.

Preferably, $R^4$ is hydrogen, halogen or cyano, and further preferably hydrogen or halogen.

Preferably, $R^7$ is hydrogen.

Preferably, $R^8$ is hydrogen.

Preferred combinations of substituents of a compound represented by formula (I) include the following 1) to 25):

1) a compound wherein Y is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl, and $R^3$ is substituted or unsubstituted aryl, substituted or unsubstituted heteroaryl, or substituted or unsubstituted alkyloxy, 2) a compound wherein Y is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl, and $R^3$ is substituted or unsubstituted aryl, 3) a compound wherein Y is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl, and $R^4$ is hydrogen or halogen, 4) a compound wherein Y is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl, and T is —N=, 5) a compound wherein Y is substituted or unsubstituted alkyl, substituted or unsubstituted alkenyl, or substituted or unsubstituted alkynyl, and $R^3$ is substituted or unsubstituted aryl, substituted or unsubstituted heteroaryl, or substituted or unsubstituted alkyloxy, 6) a compound wherein Y is substituted or unsubstituted alkyl, substituted or unsubstituted alkenyl, or substituted or unsubstituted alkynyl, and $R^3$ is substituted or unsubstituted aryl, 7) a compound wherein Y is substituted or unsubstituted aryl, substituted or unsubstituted heteroaryl, substituted or unsubstituted cycloalkyl, substituted or unsubstituted cycloalkenyl, or substituted or unsubstituted heterocyclyl, and $R^3$ is substituted or unsubstituted aryl, substituted or unsubstituted heteroaryl, or substituted or unsubstituted alkyloxy, 8) a compound wherein Y is substituted or unsubstituted aryl, substituted or unsubstituted heteroaryl, substituted or unsubstituted cycloalkyl, substituted or unsubstituted cycloalkenyl, or substituted or unsubstituted heterocyclyl, and $R^3$ is substituted or unsubstituted aryl, 9) a compound wherein Y is substituted or unsubstituted alkyl, substituted or unsubstituted alkenyl, or substituted or unsubstituted alkynyl, and $R^4$ is hydrogen or halogen, 10) a compound wherein Y is substituted or unsubstituted aryl, substituted or unsubstituted heteroaryl, substituted or unsubstituted cycloalkyl, substituted or unsubstituted cycloalkenyl, or substituted or unsubstituted heterocyclyl, and $R^4$ is hydrogen or halogen, 11) a compound wherein Y is substituted or unsubstituted aryl, substituted or unsubstituted heteroaryl, substituted or unsubstituted cycloalkyl, substituted or unsubstituted cycloalkenyl, or substituted or unsubstituted heterocyclyl, and T is —N=, 12) a compound wherein Y is substituted or unsubstituted alkyl, substituted or unsubstituted alkenyl, or substituted or unsubstituted alkynyl, and T is —N=, 13) a compound wherein $R^3$ is substituted or unsubstituted aryl, substituted or unsubstituted heteroaryl, or substituted or unsubstituted alkyloxy, and $R^4$ is hydrogen or halogen, 14) a compound wherein $R^3$ is substituted or unsubstituted aryl, and $R^4$ is hydrogen or halogen, 15) a compound wherein T is —N=, and $R^3$ is substituted or unsubstituted aryl, substituted or unsubstituted heteroaryl, or substituted or unsubstituted alkyloxy, 16) a compound wherein T is —N=, and $R^3$ is substituted or unsubstituted aryl, 17) a compound wherein T is —N=, and $R^4$ is hydrogen or halogen, 18) a compound wherein Y is substituted or unsubstituted aryl, substituted or unsubstituted heteroaryl, substituted or unsubstituted cycloalkyl, substituted or unsubstituted cycloalkenyl, or substituted or unsubstituted heterocyclyl, $R^3$ is substituted or unsubstituted aryl, substituted or unsubstituted heteroaryl, or substituted or unsubstituted alkyloxy, and $R^4$ is hydrogen or halogen, 19) a compound wherein Y is substituted or unsubstituted aryl, substituted or unsubstituted heteroaryl, substituted or unsubstituted cycloalkyl, substituted or unsubstituted cycloalkenyl, or substituted or unsubstituted heterocyclyl, $R^3$ is substituted or unsubstituted aryl, substituted or unsubstituted heteroaryl, or substituted or unsubstituted alkyloxy, $R^4$ is hydrogen or halogen, and T is —N=, 20) a compound wherein Y is substituted or unsubstituted aryl, substituted or unsubstituted heteroaryl, substituted or unsubstituted cycloalkyl, substituted or unsubstituted cycloalkenyl, or substituted or unsubstituted heterocyclyl, $R^3$ is substituted or unsubstituted aryl, and $R^4$ is hydrogen or halogen, 21) a compound wherein Y is substituted or unsubstituted aryl, substituted or unsubstituted heteroaryl, substituted or unsubstituted cycloalkyl, substituted or unsubstituted cycloalkenyl, or substituted or unsubstituted heterocyclyl, $R^3$ is substituted or unsubstituted aryl, $R^4$ is hydrogen or halogen, and T is —N=, 22) a compound wherein Y is substituted or unsubstituted alkyl, substituted or unsubstituted alkenyl, or substituted or unsubstituted alkynyl, $R^3$ is substituted or unsubstituted aryl, substituted or unsubstituted heteroaryl, or substituted or unsubstituted alkyloxy, and $R^4$ is hydrogen or halogen, 23) a compound wherein Y is substituted or unsubstituted alkyl, substituted or unsubstituted alkenyl, or substituted or unsubstituted alkynyl, $R^3$ is substituted or unsubstituted aryl, substituted or unsubstituted heteroaryl, or substituted or unsubstituted alkyloxy, $R^4$ is hydrogen or halogen, and T is —N=, 24) a compound wherein Y is substituted or unsubstituted alkyl, substituted or unsubstituted alkenyl, or substituted or unsubstituted alkynyl, $R^3$ is substituted or unsubstituted aryl, and $R^4$ is hydrogen or halogen, 25) a compound wherein Y is substituted or unsubstituted alkyl, substituted or unsubstituted alkenyl, or substituted or unsubstituted alkynyl, $R^3$ is substituted or unsubstituted aryl, $R^4$ is hydrogen or halogen, and T is —N=.

Preferred combinations of substituents of a compound represented by formula (II) include the following 1) to 62):

1) a compound wherein X is —O—, —S—, —$NR^5$—, —C(=O)—, or —C(=O)$NR^6$—, and $R^1$ is hydrogen, 2) a compound wherein X is —O—, —S—, or —$NR^5$—, and $R^1$ is hydrogen, 3) a compound wherein X is —O—, and $R^1$ is hydrogen, 4) a compound wherein $R^1$ is hydrogen, and Y is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl, 5) a compound wherein $R^1$ is hydrogen, and Y is substituted or unsubstituted aryl, substituted or unsubstituted heteroaryl, substituted or unsubstituted cycloalkyl, substituted or unsubstituted cycloalkenyl, or substituted or unsubstituted heterocyclyl, 6) a compound wherein $R^1$ is hydrogen, and Y is substituted or unsubstituted alkyl, substituted or unsubstituted alkenyl, or substituted or unsubstituted alkynyl, 7) a compound wherein $R^1$ is hydrogen, and $R^3$ is substituted or unsubstituted aryl, substituted or unsubstituted heteroaryl, or substituted or unsubstituted alkyloxy, 8) a compound wherein $R^1$ is hydrogen, and $R^3$ is substituted or unsubstituted aryl, 9) a compound wherein $R^1$ is hydrogen, and $R^4$ is hydrogen or halogen, 10) a compound wherein $R^1$ is hydrogen, and T is —N=, 11) a compound wherein X is —O—, —S—, or —$NR^5$—, and Y is substituted or unsubstituted alkyl, substituted or unsubstituted alkenyl, or substituted or unsubstituted alkynyl, 12) a compound wherein X is —O—, —S—, or —$NR^5$—, and Y is substituted or unsubstituted aryl, substituted or unsubstituted heteroaryl, substituted or unsubstituted cycloalkyl, substituted or unsubstituted cycloalkenyl, or substituted or unsubstituted heterocyclyl, 13) a compound wherein X is —O—, and Y is substituted or unsubstituted alkyl, substituted or unsubstituted alkenyl, or substituted or unsubstituted alkynyl, 14) a compound wherein X is —O—, and Y is substituted or unsubstituted aryl, substituted or unsubstituted heteroaryl, substituted or unsubstituted cycloalkyl, substituted or unsubstituted cycloalkenyl, or substituted or unsubstituted heterocyclyl, 15) a compound wherein X is —O—, —S—, or —$NR^5$—, and $R^3$ is substituted or unsubstituted aryl, substituted or unsubstituted heteroaryl, or substituted or unsubstituted alkyloxy, 16) a compound wherein X is —O—, —S—, or —$NR^5$—, and $R^3$ is substituted or unsubstituted aryl, 17) a compound wherein X is —O—, and $R^3$ is substituted or unsubstituted aryl, substituted or unsubstituted heteroaryl, or substituted or unsubstituted alkyloxy, 18) a compound wherein X is —O—, and $R^3$ is substituted or unsubstituted aryl, 19) a compound wherein X is —O—, —S—, or —$NR^5$—, and $R^4$ is hydrogen or halogen, 20) a compound wherein X is —O—, and $R^4$ is hydrogen or halogen, 21) a compound wherein X is —O—, —S—, or —$NR^5$—, and T is —N=, 22) a compound wherein X is —O—, and T is —N=, 23) a compound wherein Y is substituted or unsubstituted alkyl, substituted or unsubstituted alkenyl, or substituted or unsubstituted alkynyl, and $R^3$ is substituted or unsubstituted aryl, substituted or unsubstituted heteroaryl, or substituted or unsubstituted alkyloxy, 24) a compound wherein Y is substituted or unsubstituted alkyl, substituted or unsubstituted alkenyl, or substituted or unsubstituted alkynyl, and $R^3$ is substituted or unsubstituted aryl, 25) a compound wherein Y is substituted or unsubstituted aryl, substituted or unsubstituted heteroaryl, substituted or unsubstituted cycloalkyl, substituted or unsubstituted cycloalkenyl, or substituted or unsubstituted heterocyclyl, and $R^3$ is substituted or unsubstituted aryl, substituted or unsubstituted heteroaryl, or substituted or unsubstituted alkyloxy, 26) a compound wherein Y is substituted or unsubstituted aryl, substituted or unsubstituted heteroaryl, substituted or unsubstituted cycloalkyl, substituted or unsubstituted cycloalkenyl, or substituted or unsubstituted heterocyclyl, and $R^3$ is substituted or unsubstituted aryl, 27) a compound wherein Y is substituted or unsubstituted alkyl, substituted or unsubstituted alkenyl, or substituted or unsubstituted alkynyl, and $R^4$ is hydrogen or halogen, 28) a compound wherein Y is substituted or unsubstituted aryl, substituted or unsubstituted heteroaryl, substituted or unsubstituted cycloalkyl, substituted or unsubstituted cycloalkenyl, or substituted or unsubstituted heterocyclyl, and
$R^4$ is hydrogen or halogen,
29) a compound wherein Y is substituted or unsubstituted aryl, substituted or unsubstituted heteroaryl, substituted or unsubstituted cycloalkyl, substituted or unsubstituted cycloalkenyl, or substituted or unsubstituted heterocyclyl, and
T is —N═,
30) a compound wherein Y is substituted or unsubstituted alkyl, substituted or unsubstituted alkenyl, or substituted or unsubstituted alkynyl, and
T is —N═,
31) a compound wherein $R^3$ is substituted or unsubstituted aryl, substituted or unsubstituted heteroaryl, or substituted or unsubstituted alkyloxy, and
$R^4$ is hydrogen or halogen,
32) a compound wherein T is —N═, and
$R^3$ is substituted or unsubstituted aryl, substituted or unsubstituted heteroaryl, or substituted or unsubstituted alkyloxy,
33) a compound wherein T is —N═, and
$R^3$ is substituted or unsubstituted aryl,
34) a compound wherein T is —N═, and
$R^4$ is hydrogen or halogen,
35) a compound wherein $R^1$ is hydrogen,
X is —O—, —S—, or —NR⁵—, and
Y is substituted or unsubstituted aryl, substituted or unsubstituted heteroaryl, substituted or unsubstituted cycloalkyl, substituted or unsubstituted cycloalkenyl, or substituted or unsubstituted heterocyclyl,
36) a compound wherein $R^1$ is hydrogen,
X is —O—, —S—, or —NR⁵—, and
Y is substituted or unsubstituted alkyl, substituted or unsubstituted alkenyl, or substituted or unsubstituted alkynyl,
37) a compound wherein $R^1$ is hydrogen,
X is —O—, and
Y is substituted or unsubstituted aryl, substituted or unsubstituted heteroaryl, substituted or unsubstituted cycloalkyl, substituted or unsubstituted cycloalkenyl, or substituted or unsubstituted heterocyclyl,
38) a compound wherein $R^1$ is hydrogen,
X is —O—, and
Y is substituted or unsubstituted alkyl, substituted or unsubstituted alkenyl, or substituted or unsubstituted alkynyl,
39) a compound wherein $R^1$— is hydrogen,
X is —O—, —S—, or —NR⁵—, and
$R^3$ is substituted or unsubstituted aryl, substituted or unsubstituted heteroaryl, or substituted or unsubstituted alkyloxy,
40) a compound wherein $R^1$ is hydrogen,
X is —O—, —S—, or —NR⁵—, and
$R^3$ is substituted or unsubstituted aryl,
41) a compound wherein $R^1$ is hydrogen,
X is —O—, and
$R^3$ is substituted or unsubstituted aryl, substituted or unsubstituted heteroaryl, or substituted or unsubstituted alkyloxy,
42) a compound wherein $R^1$ is hydrogen,
X is —O—, and
$R^3$ is substituted or unsubstituted aryl,
43) a compound wherein $R^1$ is hydrogen,
Y is substituted or unsubstituted aryl, substituted or unsubstituted heteroaryl, substituted or unsubstituted cycloalkyl, substituted or unsubstituted cycloalkenyl, or substituted or unsubstituted heterocyclyl, and
$R^3$ is substituted or unsubstituted aryl, substituted or unsubstituted heteroaryl, or substituted or unsubstituted alkyloxy,
44) a compound wherein $R^1$ is hydrogen,
Y is substituted or unsubstituted aryl, substituted or unsubstituted heteroaryl, substituted or unsubstituted cycloalkyl, substituted or unsubstituted cycloalkenyl, or substituted or unsubstituted heterocyclyl, and
$R^3$ is substituted or unsubstituted aryl,
45) a compound wherein $R^1$ is hydrogen,
Y is substituted or unsubstituted alkyl, substituted or unsubstituted alkenyl, or substituted or unsubstituted alkynyl, and
$R^3$ is substituted or unsubstituted aryl, substituted or unsubstituted heteroaryl, or substituted or unsubstituted alkyloxy,
46) a compound wherein $R^1$ is hydrogen,
Y is substituted or unsubstituted alkyl, substituted or unsubstituted alkenyl, or substituted or unsubstituted alkynyl, and
$R^3$ is substituted or unsubstituted aryl,
47) a compound wherein $R^1$ is hydrogen,
X is —O—, —S—, or —NR⁵—,
Y is substituted or unsubstituted aryl, substituted or unsubstituted heteroaryl, substituted or unsubstituted cycloalkyl, substituted or unsubstituted cycloalkenyl, or substituted or unsubstituted heterocyclyl, and
$R^3$ is substituted or unsubstituted aryl, substituted or unsubstituted heteroaryl, or substituted or unsubstituted alkyloxy,
48) a compound wherein $R^1$ is hydrogen,
X is —O—, —S—, or —NR⁵—,
Y is substituted or unsubstituted aryl, substituted or unsubstituted heteroaryl, substituted or unsubstituted cycloalkyl, substituted or unsubstituted cycloalkenyl, or substituted or unsubstituted heterocyclyl, and
$R^3$ is substituted or unsubstituted aryl,
49) a compound wherein $R^1$ is hydrogen,
X is —O—, —S—, or —NR⁵—,
Y is substituted or unsubstituted alkyl, substituted or unsubstituted alkenyl, or substituted or unsubstituted alkynyl, and
$R^3$ is substituted or unsubstituted aryl, substituted or unsubstituted heteroaryl, or substituted or unsubstituted alkyloxy,
50) a compound wherein $R^1$ is hydrogen,
X is —O—, —S—, or —NR⁵—,
Y is substituted or unsubstituted alkyl, substituted or unsubstituted alkenyl, or substituted or unsubstituted alkynyl, and
$R^3$ is substituted or unsubstituted aryl,
51) a compound wherein $R^1$ is hydrogen,
X is —O—,
Y is substituted or unsubstituted aryl, substituted or unsubstituted heteroaryl, substituted or unsubstituted cycloalkyl, substituted or unsubstituted cycloalkenyl, or substituted or unsubstituted heterocyclyl, and
$R^3$ is substituted or unsubstituted aryl, substituted or unsubstituted heteroaryl, or substituted or unsubstituted alkyloxy,
52) a compound wherein $R^1$ is hydrogen,
X is —O—,
Y is substituted or unsubstituted aryl, substituted or unsubstituted heteroaryl, substituted or unsubstituted cycloalkyl, substituted or unsubstituted cycloalkenyl, or substituted or unsubstituted heterocyclyl, and
$R^3$ is substituted or unsubstituted aryl,
53) a compound wherein $R^1$ is hydrogen,
X is —O—,
Y is substituted or unsubstituted alkyl, substituted or unsubstituted alkenyl, or substituted or unsubstituted alkynyl,
$R^3$ is substituted or unsubstituted aryl, substituted or unsubstituted heteroaryl, or substituted or unsubstituted alkyloxy,
54) a compound wherein $R^1$ is hydrogen,
X is —O—,
Y is substituted or unsubstituted alkyl, substituted or unsubstituted alkenyl, or substituted or unsubstituted alkynyl, and
$R^3$ is substituted or unsubstituted aryl,
55) a compound wherein $R^1$ is hydrogen,
X is —O—, —S—, or —$NR^5$—,
Y is substituted or unsubstituted aryl, substituted or unsubstituted heteroaryl, substituted or unsubstituted cycloalkyl, substituted or unsubstituted cycloalkenyl, or substituted or unsubstituted heterocyclyl,
$R^3$ is substituted or unsubstituted aryl, substituted or unsubstituted heteroaryl, or substituted or unsubstituted alkyloxy, and $R^4$ is hydrogen or halogen,
56) a compound wherein $R^1$ is hydrogen,
X is —O—, —S—, or —$NR^5$—,
Y is substituted or unsubstituted aryl, substituted or unsubstituted heteroaryl, substituted or unsubstituted cycloalkyl, substituted or unsubstituted cycloalkenyl, or substituted or unsubstituted heterocyclyl,
$R^3$ is substituted or unsubstituted aryl, and
$R^4$ is hydrogen or halogen,
57) a compound wherein $R^1$ is hydrogen,
X is —O—, —S—, or —$NR^5$—,
Y is substituted or unsubstituted alkyl, substituted or unsubstituted alkenyl, or substituted or unsubstituted alkynyl,
$R^3$ is substituted or unsubstituted aryl, substituted or unsubstituted heteroaryl, or substituted or unsubstituted alkyloxy, and
$R^4$ is hydrogen or halogen,
58) a compound wherein $R^1$ is hydrogen,
X is —O—, —S—, or —$NR^5$—,
Y is substituted or unsubstituted alkyl, substituted or unsubstituted alkenyl, or substituted or unsubstituted alkynyl,
$R^3$ is substituted or unsubstituted aryl, and
$R^4$ is hydrogen or halogen,
59) a compound wherein $R^1$ is hydrogen,
X is —O—,
Y is substituted or unsubstituted aryl, substituted or unsubstituted heteroaryl, substituted or unsubstituted cycloalkyl, substituted or unsubstituted cycloalkenyl, or substituted or unsubstituted heterocyclyl,
$R^3$ is substituted or unsubstituted aryl, substituted or unsubstituted heteroaryl, or substituted or unsubstituted alkyloxy,
$R^4$ is hydrogen or halogen,
60) a compound wherein $R^1$ is hydrogen,
X is —O—,
Y is substituted or unsubstituted aryl, substituted or unsubstituted heteroaryl, substituted or unsubstituted cycloalkyl, substituted or unsubstituted cycloalkenyl, or substituted or unsubstituted heterocyclyl,
$R^3$ is substituted or unsubstituted aryl, and
$R^4$ is hydrogen or halogen,
61) a compound wherein $R^1$ is hydrogen,
X is —O—,
Y is substituted or unsubstituted alkyl, substituted or unsubstituted alkenyl, or substituted or unsubstituted alkynyl,
$R^3$ is substituted or unsubstituted aryl, substituted or unsubstituted heteroaryl, or substituted or unsubstituted alkyloxy, and
$R^4$ is hydrogen or halogen,
62) a compound wherein $R^1$ is hydrogen,
X is —O—,
Y is substituted or unsubstituted alkyl, substituted or unsubstituted alkenyl, or substituted or unsubstituted alkynyl,
$R^3$ is substituted or unsubstituted aryl, and
$R^4$ is hydrogen or halogen.

Preferred combinations of substituents of a compound represented by formula (III) include the following 1) to 41):
1) a compound wherein X is —O—, —S—, or —$NR^5$—, and
Y is substituted or unsubstituted alkyl, substituted or unsubstituted alkenyl, or substituted or unsubstituted alkynyl,
2) a compound wherein X is —O—, —S—, or —$NR^5$—, and
Y is substituted or unsubstituted aryl, substituted or unsubstituted heteroaryl, substituted or unsubstituted cycloalkyl, substituted or unsubstituted cycloalkenyl, or substituted or unsubstituted heterocyclyl,
3) a compound wherein X is —O—, and
Y is substituted or unsubstituted alkyl, substituted or unsubstituted alkenyl, or substituted or unsubstituted alkynyl,
4) a compound wherein X is —O—, and
Y is substituted or unsubstituted aryl, substituted or unsubstituted heteroaryl, substituted or unsubstituted cycloalkyl, substituted or unsubstituted cycloalkenyl, or substituted or unsubstituted heterocyclyl,
5) a compound wherein X is —O—, —S—, or —$NR^5$—, and
$R^3$ is substituted or unsubstituted aryl, substituted or unsubstituted heteroaryl, or substituted or unsubstituted alkyloxy,
6) a compound wherein X is —O—, —S—, or —$NR^5$—, and
$R^3$ is substituted or unsubstituted aryl,
7) a compound wherein X is —O—, and
$R^3$ is substituted or unsubstituted aryl, substituted or unsubstituted heteroaryl, or substituted or unsubstituted alkyloxy,
8) a compound wherein X is —O—, and
$R^3$ is substituted or unsubstituted aryl,
9) a compound wherein X is —O—, —S—, or —$NR^5$—, and
$R^4$ is hydrogen or halogen,
10) a compound wherein X is —O—, and
$R^4$ is hydrogen or halogen,
11) a compound wherein X is —O—, —S—, or —$NR^5$—, and
T is —N=,
12) a compound wherein X is —O—, and
T is —N=,
13) a compound wherein Y is substituted or unsubstituted alkyl, substituted or unsubstituted alkenyl, or substituted or unsubstituted alkynyl, and
$R^3$ is substituted or unsubstituted aryl, substituted or unsubstituted heteroaryl, or substituted or unsubstituted alkyloxy,
14) a compound wherein Y is substituted or unsubstituted alkyl, substituted or unsubstituted alkenyl, or substituted or unsubstituted alkynyl, and
$R^3$ is substituted or unsubstituted aryl, 15) a compound wherein Y is substituted or unsubstituted aryl, substituted or unsubstituted heteroaryl, substituted or unsubstituted cycloalkyl, substituted or unsubstituted cycloalkenyl, or substituted or unsubstituted heterocyclyl, and
$R^3$ is substituted or unsubstituted aryl, substituted or unsubstituted heteroaryl, or substituted or unsubstituted alkyloxy,
16) a compound wherein Y is substituted or unsubstituted aryl, substituted or unsubstituted heteroaryl, substituted or unsubstituted cycloalkyl, substituted or unsubstituted cycloalkenyl, or substituted or unsubstituted heterocyclyl, and
$R^3$ is substituted or unsubstituted aryl,
17) a compound wherein Y is substituted or unsubstituted alkyl, substituted or unsubstituted alkenyl, or substituted or unsubstituted alkynyl, and
$R^4$ is hydrogen or halogen,
18) a compound wherein Y is substituted or unsubstituted aryl, substituted or unsubstituted heteroaryl, substituted or unsubstituted cycloalkyl, substituted or unsubstituted cycloalkenyl, or substituted or unsubstituted heterocyclyl, and
$R^4$ is hydrogen or halogen,
19) a compound wherein Y is substituted or unsubstituted aryl, substituted or unsubstituted heteroaryl, substituted or unsubstituted cycloalkyl, substituted or unsubstituted cycloalkenyl, or substituted or unsubstituted heterocyclyl, and
T is —N═,
20) a compound wherein Y is substituted or unsubstituted alkyl, substituted or unsubstituted alkenyl, or substituted or unsubstituted alkynyl, and
T is —N═,
21) a compound wherein $R^3$ is substituted or unsubstituted aryl, substituted or unsubstituted heteroaryl, or substituted or unsubstituted alkyloxy, and
$R^4$ is hydrogen or halogen,
22) a compound wherein $R^3$ is substituted or unsubstituted aryl, and
$R^4$ is hydrogen or halogen,
23) a compound wherein T is —N═,
$R^3$ is substituted or unsubstituted aryl, substituted or unsubstituted heteroaryl, or substituted or unsubstituted alkyloxy,
24) a compound wherein T is —N═, and
$R^3$ is substituted or unsubstituted aryl,
25) a compound wherein T is —N═, and
$R^4$ is hydrogen or halogen,
26) a compound wherein X is —O—, —S—, or —$NR^5$—,
Y is substituted or unsubstituted aryl, substituted or unsubstituted heteroaryl, substituted or unsubstituted cycloalkyl, substituted or unsubstituted cycloalkenyl, or substituted or unsubstituted heterocyclyl, and
$R^3$ is substituted or unsubstituted aryl, substituted or unsubstituted heteroaryl, or substituted or unsubstituted alkyloxy,
27) a compound wherein X is —O—, —S—, or —$NR^5$—,
Y is substituted or unsubstituted aryl, substituted or unsubstituted heteroaryl, substituted or unsubstituted cycloalkyl, substituted or unsubstituted cycloalkenyl, or substituted or unsubstituted heterocyclyl, and
$R^3$ is substituted or unsubstituted aryl,
28) a compound wherein X is —O—, —S—, or —$NR^5$—,
Y is substituted or unsubstituted alkyl, substituted or unsubstituted alkenyl, or substituted or unsubstituted alkynyl, and
$R^3$ is substituted or unsubstituted aryl, substituted or unsubstituted heteroaryl, or substituted or unsubstituted alkyloxy,
29) a compound wherein X is —O—, —S—, or —$NR^5$—,
Y is substituted or unsubstituted alkyl, substituted or unsubstituted alkenyl, or substituted or unsubstituted alkynyl, and
$R^3$ is substituted or unsubstituted aryl,
30) a compound wherein X is —O—,
Y is substituted or unsubstituted aryl, substituted or unsubstituted heteroaryl, substituted or unsubstituted cycloalkyl, substituted or unsubstituted cycloalkenyl, or substituted or unsubstituted heterocyclyl, and
$R^3$ is substituted or unsubstituted aryl, substituted or unsubstituted heteroaryl, or substituted or unsubstituted alkyloxy,
31) a compound wherein X is —O—,
Y is substituted or unsubstituted aryl, substituted or unsubstituted heteroaryl, substituted or unsubstituted cycloalkyl, substituted or unsubstituted cycloalkenyl, or substituted or unsubstituted heterocyclyl, and
$R^3$ is substituted or unsubstituted aryl,
32) a compound wherein X is —O—,
Y is substituted or unsubstituted alkyl, substituted or unsubstituted alkenyl, or substituted or unsubstituted alkynyl, and
$R^3$ is substituted or unsubstituted aryl, substituted or unsubstituted heteroaryl, or substituted or unsubstituted alkyloxy,
33) a compound wherein X is —O—,
Y is substituted or unsubstituted alkyl, substituted or unsubstituted alkenyl, or substituted or unsubstituted alkynyl, and
$R^3$ is substituted or unsubstituted aryl,
34) a compound wherein X is —O—, —S—, or —$NR^5$—,
Y is substituted or unsubstituted aryl, substituted or unsubstituted heteroaryl, substituted or unsubstituted cycloalkyl, substituted or unsubstituted cycloalkenyl, or substituted or unsubstituted heterocyclyl,
$R^3$ is substituted or unsubstituted aryl, substituted or unsubstituted heteroaryl, or substituted or unsubstituted alkyloxy, and
$R^4$ is hydrogen or halogen,
35) a compound wherein X is —O—, —S—, or —$NR^5$—,
Y is substituted or unsubstituted aryl, substituted or unsubstituted heteroaryl, substituted or unsubstituted cycloalkyl, substituted or unsubstituted cycloalkenyl, or substituted or unsubstituted heterocyclyl,
$R^3$ is substituted or unsubstituted aryl, and
$R^4$ is hydrogen or halogen,
36) a compound wherein X is —O—, —S—, or —$NR^5$—,
Y is substituted or unsubstituted alkyl, substituted or unsubstituted alkenyl, or substituted or unsubstituted alkynyl,
$R^3$ is substituted or unsubstituted aryl, substituted or unsubstituted heteroaryl, or substituted or unsubstituted alkyloxy, and
$R^4$ is hydrogen or halogen, 37) a compound wherein X is —O—, —S—, or —NR$^5$—, Y is substituted or unsubstituted alkyl, substituted or unsubstituted alkenyl, or substituted or unsubstituted alkynyl,
R$^3$ is substituted or unsubstituted aryl, and
R$^4$ is hydrogen or halogen,
38) a compound wherein X is —O—,
Y is substituted or unsubstituted aryl, substituted or unsubstituted heteroaryl, substituted or unsubstituted cycloalkyl, substituted or unsubstituted cycloalkenyl, or substituted or unsubstituted heterocyclyl,
R$^3$ is substituted or unsubstituted aryl, substituted or unsubstituted heteroaryl, or substituted or unsubstituted alkyloxy, and
R$^4$ is hydrogen or halogen,
39) a compound wherein X is —O—, Y is substituted or unsubstituted aryl, substituted or unsubstituted heteroaryl, substituted or unsubstituted cycloalkyl, substituted or unsubstituted cycloalkenyl, or substituted or unsubstituted heterocyclyl,
R$^3$ is substituted or unsubstituted aryl, and
R$^4$ is hydrogen or halogen,
40) a compound wherein X is —O—,
Y is substituted or unsubstituted alkyl, substituted or unsubstituted alkenyl, or substituted or unsubstituted alkynyl,
R$^3$ is substituted or unsubstituted aryl, substituted or unsubstituted heteroaryl, or substituted or unsubstituted alkyloxy, and
R$^4$ is hydrogen or halogen,
41) a compound wherein X is —O—,
Y is substituted or unsubstituted alkyl, substituted or unsubstituted alkenyl, or substituted or unsubstituted alkynyl,
R$^3$ is substituted or unsubstituted aryl, and
R$^4$ is hydrogen or halogen.

One or more hydrogen, carbon or other atoms of the compounds of formula (I), formula (II) and formula (III) of the present invention can be replaced by an isotope of the hydrogen, carbon or other atoms.

For example, compounds of formula (I) include all radiolabeled forms of compounds of formula (I). The "radioactive labeling," "radiolabeled form" and the like of the compound of formula (I) are encompassed by the present invention and useful as a research and/or diagnostic tool in metabolism pharmacokinetic studies and in binding assays.

Examples of isotopes that can be incorporated into the compound of formula (I) of the present invention include isotopes of hydrogen, carbon, nitrogen, oxygen, phosphorous, sulfur, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F and $^{36}$Cl, respectively. Radiolabeled compounds of the present invention can be prepared by methods known in the art. For example, tritium-labeled compounds of formula (I) can be prepared by introducing tritium into the particular compound of formula (I), for example, by catalytic dehalogenation with tritium. This method may include reacting a suitably halogen-substituted precursor of a compound of formula (I) with tritium gas in the presence of a suitable catalyst such as Pd/C, in the presence or absence of a base. Other suitable methods for preparing tritiated compounds can be found in Isotopes in the Physical and Biomedical Sciences, Vol. 1, Labeled Compounds (Part A), Chapter 6 (1987). $^{14}$C-labeled compounds can be prepared by employing starting materials having a $^{14}$C carbon.

As a pharmaceutically acceptable salt of the present compound, the following salts can be included.

As a basic salt, example includes alkali metal salt such as sodium salt or potassium salt; alkaline earth metal salt such as calcium salt or strontium salt; metal salt such as beryllium salt, magnesium salt, zinc salt or transition metal salt; ammonium salt; aliphatic amine salt such as trimethylamine salt, triethylamine salt, dicyclohexylamine salt, ethanolamine salt, diethanolamine salt, triethanolamine salt, procaine salt, meglumine salt, diethanolamine salt or ethylenediamine salt; aralkylamine salt such as N,N-dibenzylethylenediamine salt or benethamine salt; heterocyclic aromatic amine salt such as pyridine salt, picoline salt, quinoline salt, or isoquinoline salt; quaternary ammonium salt such as tetramethylammonium salt, tetraethylammonium salt, benzyltrimethylammonium salt, benzyltriethylammonium salt, benzyltributylammonium salt, methyltrioctylammonium salt, or tetrabutylammonium salt; basic amino acid salt such as arginine salt or lysine salt or the like.

As an acidic salt, example includes inorganic acid salt such as hydrochloride, sulfate, nitrate, phosphate, carbonate, hydrogencarbonate, or perchlorate; organic acid salt such as acetate, propionate, lactate, maleate, fumarate, tartrate, malate, citrate or ascorbate; sulfonate such as methanesulfonate, isethionate, benzenesulfonate or p-toluenesulfonate; acidic amino acid salt such as aspartate or glutamate or the like.

A compound represented by formula (I), formula (II) and formula (III) in the present invention or its pharmaceutically acceptable salt can form a solvate (e.g. hydrate etc.) and/or a crystal polymorph, and the present invention also contains such various types of solvate and crystal polymorph. In the "solvate", any number of solvent molecules (e.g. water molecule etc.) may be coordinated with a compound represented by formula (I). When left in the atmosphere, a compound represented by formula (I) or its pharmaceutically acceptable salt may absorb water, and a case where adsorbed water is attached thereto or a case where hydrate is formed may arise. In addition, by recrystallization of a compound represented by formula (I) or its pharmaceutically acceptable salt, a crystal polymorph thereof can be formed.

A compound represented by formula (I), formula (II) and formula (III) in the present invention or its pharmaceutically acceptable salt can form a prodrug, and the present invention also contains such various types of prodrug. The prodrugs are a derivative of the compound of the present invention, which has a chemically or metabolically decomposable group, and a compound which is changed into the compound of the present invention, which is pharmaceutically active, by solvolysis or in vivo under physiological conditions. The prodrugs contain a compound which is converted into a compound represented by formula (I), formula (II) or formula (III) by enzymatic oxidation, reduction, hydrolysis and the like in living organisms under physiological conditions; a compound which is converted into a compound represented by formula (I), formula (II) or formula (III) by hydrolysis by e.g. gastric acid; and the like. A method for selecting and a method for producing a proper prodrug derivative are described in e.g. Design of Prodrugs, Elsevier, Amsterdam 1985. Prodrugs can have activity in themselves.

When a compound represented by formula (I), formula (II) and formula (III) or its pharmaceutically acceptable salt has a hydroxyl group, prodrugs such as an acyloxy derivative and a sulfonyloxy derivative are exemplified, which derivatives are produced, for example, by a reaction of a compound having a hydroxy group and a proper acyl halide, a proper acid anhydride, a proper sulfonyl chloride, a proper sulfonyl anhydride and a mixed anhydride, or a reaction using a condensing agent. Examples thereof include $CH_3COO$—, $C_2H_5COO$—, tert-BuCOO—, $C_{15}H_{31}COO$—, PhCOO—, (m-NaOOCPh)COO—, NaOOCCH$_2$CH$_2$COO—, CH$_3$CH(NH$_2$)COO—, CH$_2$N(CH$_3$)$_2$COO—, CH$_3$SO$_3$—, CH$_3$CH$_2$SO$_3$—, CF$_3$SO$_3$—, CH$_2$FSO$_3$—, CF$_3$CH$_2$SO$_3$—, p-CH$_3$O-PhSO$_3$—, PhSO$_3$— and p-CH$_3$PhSO$_3$—.

The term "activating" means that the compound of the present invention activates the function of AMPK.

The term "pharmaceutically acceptable" means preventively or therapeutically harmless.

A general method for producing the compound of the present invention will be illustrated below. For extraction, purification and the like, treatment which is carried out in common experiments in organic chemistry may be carried out.

A compound represented by formula (I) can be synthesized as follows.

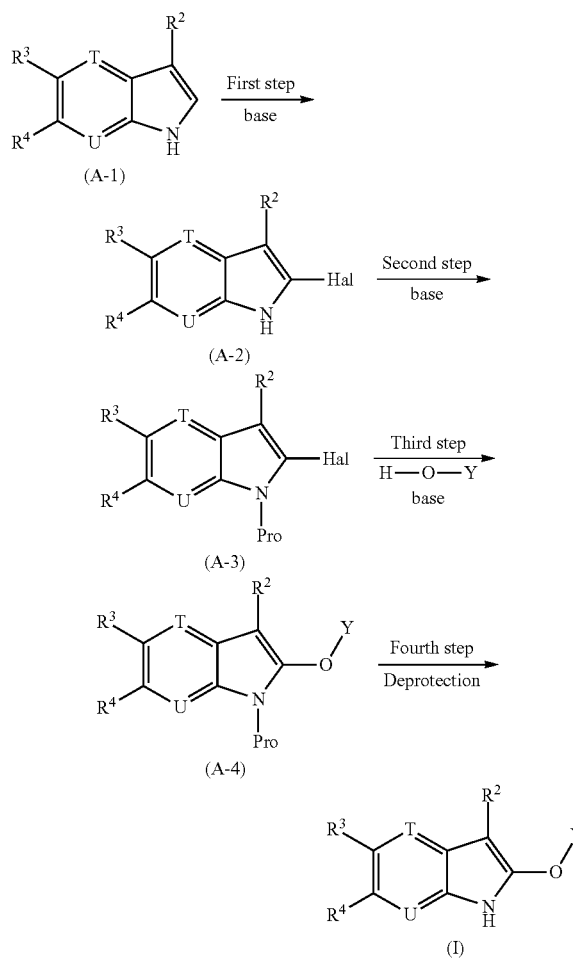

wherein, each symbol has the same meaning as above, and as a compound represented by formula (A-1), a known compound can be used and a compound which is derived from a known compound by a conventional method can be used. "Hal" is halogen, Pro is a protecting group. Pro includes a benzyl group, a benzoyl group and SEM (trimethylsilylethoxymethyl) and the like.

First Step

The first step is the step for producing a compound represented by formula (A-2) by halogenation of a compound represented by formula (A-1).

As a solvent, example includes N,N-dimethylformamide, dimethylsulfoxide, aromatic hydrocarbons (e.g. toluene, benzene, xylene etc.), saturated hydrocarbons (e.g. cyclohexane, hexane etc.), halogenated hydrocarbons (e.g. dichloromethane, chloroform, 1,2-dichloroethane etc.), ethers (e.g. tetrahydrofuran, diethyl ether, dioxane, 1,2-dimethoxyethane etc.), esters (e.g. methyl acetate, ethyl acetate etc.), ketones (e.g. acetone, methylethylketone etc.), nitriles (e.g. acetonitrile etc.), alcohols (e.g. methanol, ethanol, t-butanol etc.), water, a mixed solvent thereof or the like.

Preferably, N,N-dimethylformamide, halogenated hydrocarbons (e.g. dichloromethane, chloroform, 1,2-dichloroethane etc.), ethers (e.g. tetrahydrofuran, diethylether, dioxane, 1,2-dimethoxyethane etc.) or nitriles (e.g. acetonitrile etc.) can be used. Further preferably, alcohols (e.g. methanol, ethanol, t-butanol etc.) can be used.

As a base, example includes metal hydrides (e.g. sodium hydride etc.), metal hydroxides (e.g. sodium hydroxide, potassium hydroxide, lithium hydroxide, barium hydroxide etc.), metal carbonates (e.g. sodium carbonate, calcium carbonate, cesium carbonate etc.), metal alkoxides (e.g. sodium methoxide, sodium ethoxide, potassium t-butoxide etc.), sodium hydrogen carbonate, metal sodium, metal amides, organic amines (e.g. triethylamine, diisopropylethylamine, DBU, 2,6-lutidine etc.), pyridine, alkyllithiums (n-BuLi, sec-BuLi, tert-BuLi), or the like.

Although a base can be used, there is no need to use it. Preferably, metal hydrides (e.g. sodium hydride etc.), metal amides (e.g. lithium hexamethyldisilazide etc.), alkyllithiums (n-BuLi, sec-BuLi, tert-BuLi) or the like can be used.

The reaction can be carried out at −78 to 100° C. for 0.5 to 24 hours.

As a halogenating agent, I$_2$, Br$_2$, NIS (N-iodosuccinimide), NBS (N-bromosuccinimide) or NCS (N-chlorosuccinimide) can be used.

Second Step

The second step is the step for producing a compound represented by formula (A-3) from a compound represented by formula (A-2).

As a solvent, a solvent described in the first step can be used. Preferably, N,N-dimethylformamide, ethers (e.g. tetrahydrofuran, diethylether, dioxane, 1,2-dimethoxyethane etc.), halogenated hydrocarbons (e.g. dichloromethane, chloroform, 1,2-dichloroethane etc.), nitriles (e.g. acetonitrile etc.) or the like can be used.

As a base, a base described in the first step can be used. Preferably, metal hydrides (e.g. sodium hydride etc.), metal sodium, organic amines (e.g. triethylamine, diisopropylethylamine, DBU, 2,6-lutidine etc.), pyridine or the like can be used.

The reaction can be carried out at 0 to 100° C. for 0.5 to 12 hours.

Third Step

The third step is the step for producing a compound represented by formula (A-4) by reacting a compound represented by formula (A-3) and a compound represented by formula: H—O—Y.

As a compound represented by formula: H—O—Y, example includes phenol, methanol, ethanol or the like.

As a solvent, a solvent described in the first step can be used. Preferably, N,N-dimethylformamide, dimethyl sulfoxide, ethers (e.g. tetrahydrofuran, diethylether, dioxane, 1,2-dimethoxyethane etc.), nitriles (e.g. acetonitrile etc.) or the like can be used.

As a base, a base described in the first step can be used. Preferably, metal hydrides (e.g. sodium hydride etc.), metal carbonates (e.g. sodium carbonate, calcium carbonate, cesium carbonate etc.), metal amides, organic amines (e.g. triethylamine, diisopropylethylamine, DBU, 2,6-lutidine etc.), pyridine, alkyllithiums (n-BuLi, sec-BuLi, tert-BuLi) or the like can be used.

Further preferably, metal hydrides (e.g. sodium hydride etc.) or metal carbonates (e.g. sodium carbonate, calcium carbonate, cesium carbonate etc.) can be used.

The reaction can be carried out at 0 to 100° C. for 0.5 to 12 hours.

(when Hal is Bromine or Iodine)

The reaction can be carried out using conditions for a reaction which is known as the Ullmann reaction.

As a solvent, a solvent described in the first step can be used. Preferably, N,N-dimethylformamide, dimethylsulfoxide, ethers (e.g. tetrahydrofuran, diethyl ether, dioxane, 1,2-dimethoxyethane etc.), nitriles (e.g. acetonitrile etc.) or the like can be used.

As a base, a bases described in the third step can be used. Preferably, metal hydrides (e.g. sodium hydride etc.), metal carbonates (e.g. sodium carbonate, calcium carbonate, cesium carbonate etc.), metal amides, organic amines (e.g. triethylamine, diisopropylethylamine, DBU, 2,6-lutidine etc.), pyridine, alkyllithiums (n-BuLi, sec-BuLi, tert-BuLi) or the like can be used.

Further preferably, metal carbonates (e.g. sodium carbonate, calcium carbonate, cesium carbonate etc.) can be used.

As a catalyst, copper iodide can be used.

The reaction can be carried out at room temperature to 100° C. for 0.5 to 12 hours.

Fourth Step

The fourth step is the step for producing a compound represented by formula (I) by deprotection of a compound represented by formula (A-4).

As a solvent, a solvent described in the first step can be used. Preferably, N,N-dimethylformamide, halogenated hydrocarbons (e.g. dichloromethane, chloroform, 1,2-dichloroethane etc.), ethers (e.g. tetrahydrofuran, diethyl ether, dioxane, 1,2-dimethoxyethane etc.), esters (e.g. methyl acetate, ethyl acetate etc.), nitriles (e.g. acetonitrile etc.), alcohols (e.g. methanol, ethanol, t-butanol etc.) or the like can be used.

The reaction can be carried out in the presence of hydrochloric acid, TFA (trifluoroacetic acid), TBAF (tetrabutylammoniumfluoride) or the like at 0 to 100° C. for 0.5 to 168 hours.

A compound represented by formula (III) can be synthesized as follows.

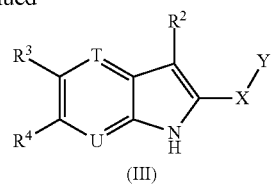

(III)

wherein, each symbol has the same meaning as above. "Hal" is halogen, Pro is a protecting group. Pro includes a benzyl group, a benzoyl group and SE M (trimethylsilylethoxymethyl) and the like.

Among compounds represented by formula (A-5), a compound, wherein X is —O—, —S— or —NR$^5$, can be synthesized as follows.

Fifth Step

The fifth step is the step for producing a compound represented by formula (A-5) by reacting a compound represented by formula (A-3) and a compound represented by formula: H—X—Y.

When X is —O—, example of a compound represented by formula: H—O—Y includes phenol, methanol, ethanol or the like.

When X is —S—, example of a compound represented by formula: H—S—Y includes thiophenol, methanethiol, ethanethiol or the like.

When X is —NR$^5$—, example of a compound represented by formula: H—NR$^5$—Y includes aniline, methylamine, ethylamine or the like.

The reaction may be carried out in the same manner as the third step.

Sixth Step

The sixth step is the step for producing a compound represented by formula (III) by deprotection of a compound represented by formula (A-5). The reaction may be carried out in the same manner as the fourth step.

Among compounds represented by formula (II), a compound, wherein R$^1$ is substituted or unsubstituted alkyl, can be synthesized, for example, from a compound represented by formula (III) by an alkylation reaction using sodium hydride and an alkylhalide.

The substituents R$^1$, R$^2$, R$^3$, R$^4$, R$^7$ and R$^8$ can be introduced in any step of the above-described first to sixth steps.

For Example, the substituent R$^3$ can be introduced as follows.

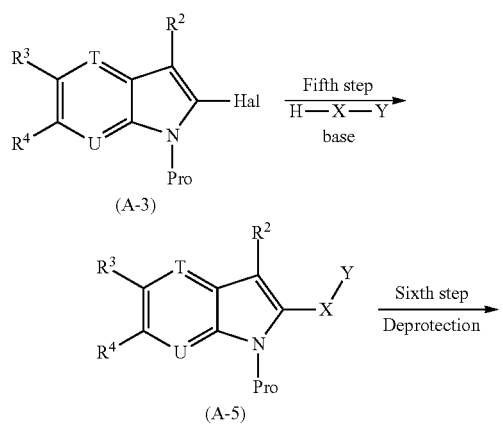

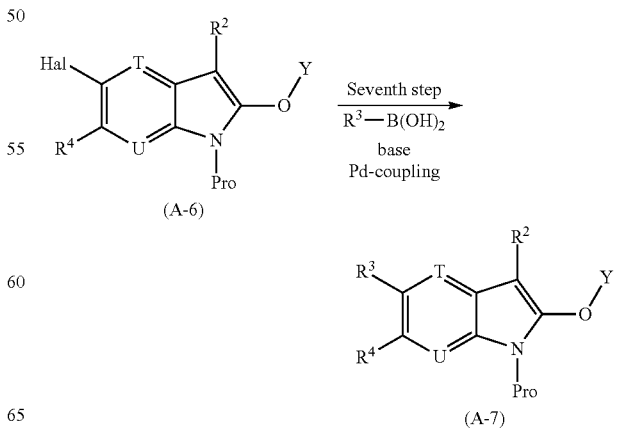

wherein, each symbol has the same meaning as above, and as a compound represented by formula (A-6), a known compound can be used and a compound which is derived from a known compound by a conventional method can be used. "Hal" is halogen, Pro is a protecting group. Pro includes a benzyl group, a benzoyl group and SEM (trimethylsilylethoxymethyl) and the like.

Seventh Step

The seventh step is the step for producing a compound represented by formula (A-7) by reacting a compound represented by formula (A-6) and a compound represented by formula: $R^3$—$B(OH)_2$ in the presence of a palladium catalyst. As a compound represented by formula: $R^3$—$B(OH)_2$, boronic acid ester can be used.

As a solvent, a solvent described in the first step can be used. Preferably, N,N-dimethylformamide, aromatic hydrocarbons (e.g. toluene, benzene, xylene etc.) or ethers (e.g. tetrahydrofuran, diethyl ether, dioxane, 1,2-dimethoxyethane etc.) can be used.

As a base, a base described in the first step can be used. Preferably, metal carbonates (e.g. sodium carbonate, calcium carbonate, cesium carbonate etc.) or organic amines (e.g. triethylamine, diisopropylethylamine, DBU, 2,6-lutidine etc.) can be used.

The reaction may be carried out in the presence of a palladium catalyst (e.g. $Pd(PPh_3)_4$, $PdCl_2$, $Pd(OAc)_2$, $Pd(dba)_2$ etc.) and a phosphine ligand (e.g. $PPh_3$, BINAP etc.) at a temperature, at which a solvent to be used is refluxed, for 0.5 to 12 hours.

When using microwave, the reaction can be carried out at 80 to 200° C. for 5 minutes to one hour.

Example of a compound represented by formula: $R^3$—$B(OH)_2$ includes phenylboronic acid or the like.

Among compounds represented by formula (A-7), a compound, wherein $R^3$ is substituted or unsubstituted alkyloxy, substituted or unsubstituted cycloalkyloxy, substituted or unsubstituted cycloalkenyloxy or substituted or unsubstituted heterocyclyloxy, can be synthesized, by converting the halogen group of the compound represented by formula (A-6) into the hydroxyl group via boronic acid ester, and an alkylation reaction using Mitsunobu reaction or various halide.

As a boronic acid ester, example includes pinacol boronic acid ester or the like.

A compound represented by formula (A-2) can also be synthesized by the following method.

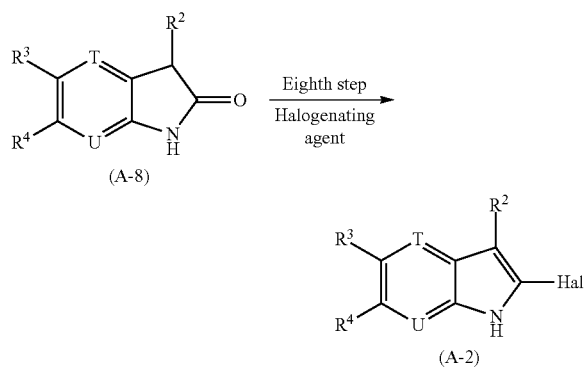

wherein each symbol has the same meaning as above, and as a compound represented by formula (A-8), a known compound can be used or a compound which is derived from a known compound by a conventional method can be used. "Hal" means halogen.

Eighth Step

The eighth step is the step for producing a compound represented by formula (A-2) by reacting a compound represented by formula (A-8) and a halogenating agent.

Although a solvent described in the first step can be used, there is no need to use it.

As a halogenating agent, example includes phosphorus oxychloride, phosphorus pentachloride, oxalyl chloride, thionyl chloride, sulfuryl chloride, dichloro triphenylphosphorane, or the like.

Particularly preferably, phosphorus oxychloride, phosphorus pentachloride, oxalyl chloride or thionyl chloride can be used.

The reaction can be carried out at 0 to 120° C. for 0.5 to 24 hours.

Various types of substituent of the compound of the present invention can be introduced by reference to (1) Alan R. Katriszly et al., Comprehensive Heterocyclic Chemistry, (2) Alan R. Katriszly et al., Comprehensive Heterocyclic Chemistry II, (3) RODD'S CHEMISTRY OF CARBON COMPOUNDS VOLUME IV HETEROCYCLIC COMPOUNDS and the like.

The compound of the present invention has an excellent AMPK activating effect. Therefore, the compound can be used for the treatment or prevention of a disease concerning AMPK, particularly disease such as type II diabetes, hyperglycemia, metabolic syndrome, obesity, hypercholesterolemia and/or hypertension. Particularly, the compound is useful in the treatment or prevention of type II diabetes, hyperglycemia, metabolic syndrome or obesity.

A pharmaceutical composition of the present invention can be administered orally or parenterally. Methods for parenteral administration include dermal, subcutaneous, intravenous, intraarterial, intramuscular, intraperitoneal, transmucosal, inhalation, transnasal, ophthalmic, inner ear or vaginal administration and the like.

In case of oral administration, any forms, which are usually used, such as oral solid formulations (e.g., tablets, powders, granules, capsules, pills, films or the like), oral liquid formulations (e.g., suspension, emulsion, elixir, syrup, lemonade, spirit, aromatic water, extract, decoction, tincture or the like) and the like may prepared according to the usual method and administered. The tablets can be sugar-coated tablets, film-coated tablets, enteric-coating tablets, sustained-release tablets, troche tablets, sublingual tablets, buccal tablets, chewable tablets or orally dispersing tablets. Powders and granules can be dry syrups. Capsules can be soft capsules, micro capsules or sustained-release capsules.

In case of parenteral administration, any forms, which are usually used, such as injections, drips, external preparations (e.g., ophthalmic drops, nasal drops, ear drops, aerosols, inhalations, lotion, infusion, liniment, mouthwash, enema, ointment, plaster, jelly, cream, patch, cataplasm, external powder, suppository or the like) and the like can be preferably administered. Injections can be emulsions whose type is O/W, W/O, O/W/O, W/O/W or the like.

The pharmaceutical composition may be manufactured by mixing an effective amount of the compound of the present invention with various pharmaceutical additives suitable for the formulation, such as excipients, binders, moistening agents, disintegrants, lubricants, diluents and the like. Furthermore, the pharmaceutical composition can be for pediatric patients, geriatric patients, serious cases or operations by appropriately changing the effective amount of the compound of the present invention, formulation and/or various pharmaceutical additives. The pediatric pharmaceutical compositions are preferably administered to patients under 12 or 15 years old. In addition, the pediatric pharmaceutical compositions can be administered to patients who are under 27 days old after the birth, 28 days to 23 months old after the birth, 2 to 11 years old, 12 to 16 years old, or 18 years old. The geriatric pharmaceutical compositions are preferably administered to patients who are 65 years old or over.

Although the dosage of a pharmaceutical composition of the present invention should be determined in consideration of the patient's age and body weight, the type and degree of diseases, the administration route and the like, a usual oral dosage is 0.05 to 100 and preferably 0.1 to 10 mg/kg/day. For parenteral administration, although the dosage highly varies with administration routes, a usual dosage is 0.005 to 10 and preferably 0.01 to 1 mg/kg/day. The dosage may be administered in one to several divisions per day.

A compound of the present invention can be used in combination with an insulin secretagogue (e.g. a sulfonylurea (SU) drug), a fast-acting insulin secretagogue (e.g. a phenylalanine derivative), a glucose uptake inhibitor (e.g. an α-glucosidase inhibitor (α-GI drug)), an insulin resistance improving drug (e.g. a biguanide drug (BG drug), a thiazolidine derivative (TZD drug)), an insulin formulation, a peptidyl peptidase IV (DPP-IV) inhibitor, a GLP-1 receptor agonist, a sodium-dependent glucose transporter 1 (SGLT1) inhibitor, a sodium-dependent glucose transporter 2 (SGLT 2) inhibitor and the like (hereinafter, abbreviated as concomitant drugs) for the purpose of an increase in the effect of the compound, a decrease in a dose of the compound or the like. In this case, the time when a compound of the present invention and a concomitant drug are administered is not restricted, and they can be administered to a subject of administration simultaneously or at intervals. Further, a compound of the present invention and a concomitant drug can be administered as two kinds of formulation comprising each active ingredient and as a single formulation comprising both active ingredients.

The dose of a concomitant drug can be suitably selected on the basis of a dosage which is clinically used. In addition, the mixing ratio of a compound of the present invention and a concomitant drug can be suitably selected depending on a subject of administration, an administration route, a target disease, symptoms, combination and the like. When a subject of administration is a human, for example, 0.01 to 100 parts by weight of a concomitant drug can be used per part by weight of a compound of the present invention.

The present invention is further explained by the following Examples, which are not intended to limit the scope of the present invention.

NMR spectrum data of the compounds of the present invention and intermediates thereof were shown. NMR analysis obtained in each example was measured by 400 MHz, and measured using CDCl$_3$, Methanol-d4 (MeOD) or dimethylsulfoxide (d6-DMSO).

LC/MS was measured under the following conditions.
(Method A)
Column: ACQUITY UPLC BEH C18 (1.7 μm i.d. 2.1×50 mm) (Waters)
Flow rate: 0.8 mL/min
UV detection wavelength: 254 nm
Mobile phase: [A] 0.1% formic acid-containing aqueous solution, [B] 0.1% formic acid-containing acetonitrile solution
Gradient: a linear gradient of the solvent [B] from 10 to 100% was carried out for 3.5 minutes and the solvent [B] at 100% was maintained for 0.5 minutes.
(Method B)
Column: Shim-pack XR-ODS (2.2 μm, i.d. 50×3.0 mm) (Shimadzu)
Flow rate: 1.6 mL/min
UV detection wavelength: 254 nm
Mobile phase: [A] 0.1% formic acid-containing aqueous solution, [B] 0.1% formic acid-containing acetonitrile solution
Gradient: a linear gradient of the solvent [B] from 10 to 100% was carried out for 3 minutes and the solvent [B] at 100% was maintained for 0.5 minutes.
(Method C)
Column: ACQUITY UPLC(Registered trademark) BEH C18 (1.7 μm i.d. 2.1×50 mm) (Waters)
Flow rate: 0.55 mL/min
UV detection wavelength: 254 nm
Mobile phase: [A] 0.1% formic acid-containing aqueous solution, [B] 0.1% formic acid-containing acetonitrile solution
Gradient: a linear gradient of the solvent [B] from 5 to 100% was carried out for 3 minutes and the solvent [B] at 100% was maintained for 0.5 minutes.

The meaning of each term in Examples is as follows.
DMF: N,N-dimethylformamide
THF: tetrahydrofuran
Pd(PPh$_3$)$_4$: tetrakis(triphenylphosphine)palladium(0)
POCl$_3$: phosphorus oxychloride
PdCl$_2$(dtbpf): 1,1'-Bis(di-tert-butylphosphino)ferrocene]dichloropalladium(II)
NCS: N-chlorosuccinimide
NBS: N-bromosuccinimide
TFA: trifluoroacetic acid
TBAF: tetrabutylammonium fluoride
DIAD: diisopropyl azodicarboxylate
UHP: urea hydrogen peroxide
mCPBA: m-chloroperoxybenzoic acid
HMPA: hexamethylphosphoric triamide Example 1

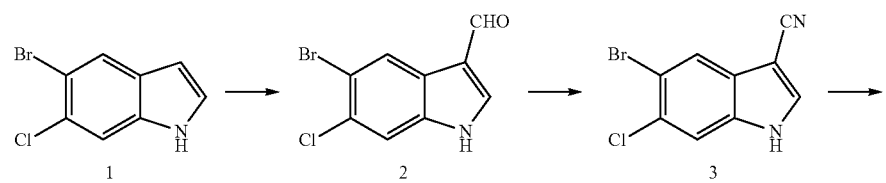

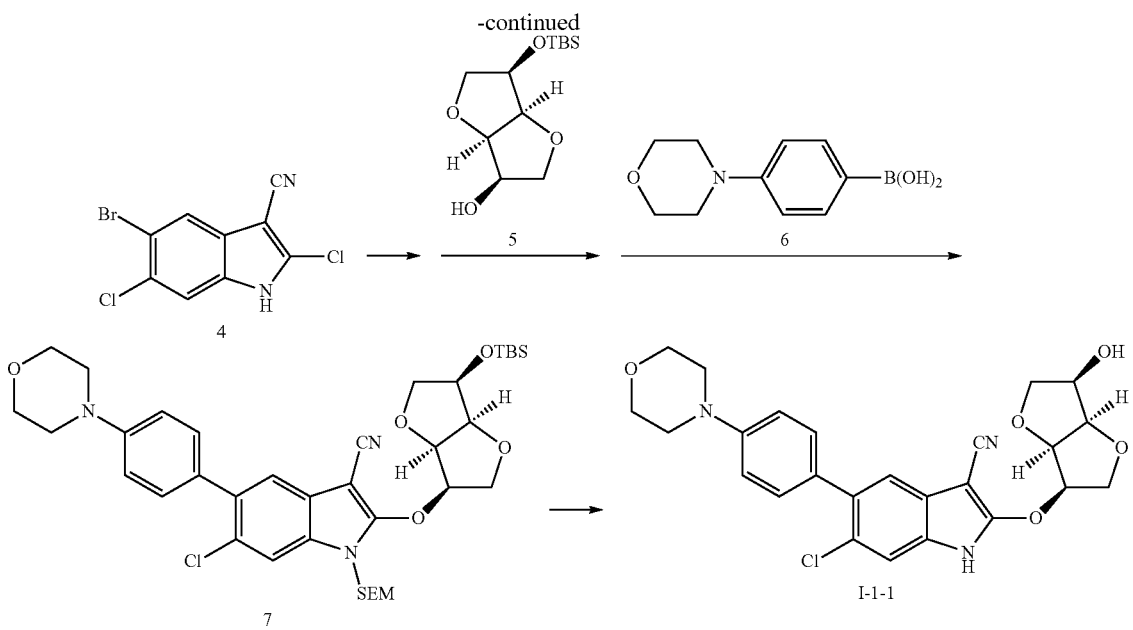

5-bromo-6-chloro-1H-indole 1 (2.00 g, 8.68 mmol) was dissolved in DMF (5 mL) and dichloromethane (5 mL), and POCl$_3$ (5 mL) was added thereto, and the reaction mixture was stirred at room temperature for approximately an hour. Thereafter, the reaction mixture was treated with iced water, and then dichloromethane was removed under reduced pressure. The precipitated solid was filtered to obtain Compound 2 (2.10 g, 93.6%).
Compound 2;
Method B
  LC/MS retention time=1.77 min.
  MS (ESI) m/z=259.75 (M+H)$^+$.

Compound 2 (1.00 g, 3.87 mmol) and hydroxyamine hydrochloride (296 mg, 4.26 mmol) were dissolved in pyridine (5 mL), and the mixture was stirred at room temperature for approximately an hour. Thereafter, acetic anhydride (804 µl, 8.51 mmol) was added thereto, and the reaction mixture was stirred with heating at 90° C. for approximately an hour. The mixture was cooled to room temperature, diluted with ethyl acetate, and washed with 2N aqueous solution of hydrochloric acid and water. The obtained organic layer was dried over magnesium sulfate and concentrated under reduced pressure. The precipitated solid was filtered to obtain Compound 3 (673 mg, 68.1%).
Compound 3;
Method B
  LC/MS retention time=1.98 min.
  MS (ESI) m/z=254.70 (M−H)$^-$.

Compound 3 (310 mg, 1.21 mmol) was suspended in carbon tetrachloride (3 mL) and THF (3 mL), and N-chlorosuccinimide (194 mg, 1.46 mmol) was added thereto, and the reaction mixture was stirred with heating. Thereafter, N-chlorosuccinimide (582 mg, 4.37 mmol) was added thereto, the reaction mixture was stirred with heating at 70° C. The mixture was cooled to room temperature and treated with 1 M aqueous solution of sodium thiosulfate. The precipitated solid was suspended by adding chloroform and filtered. The solid obtained from the filtrate and the above collected solid were combined to obtain crude Compound 4.
Compound 4;
Method B
  LC/MS retention time=2.17 min.
  MS (ESI) m/z=288.70 (M−H)$^-$.

Compound 4 (200 mg, 0.690 mmol) was dissolved in DMF (2 mL), and 60% NaH (33.1 mg, 0.828 mmol) was added thereto, and the mixture was stirred at room temperature for 3 minutes. Thereafter, 2-(chloromethoxy)ethyl trimethyl silane (147 µl, 0.828 mmol) was added thereto, and the reaction mixture was stirred at room temperature for 30 minutes. To the reaction mixture was added ethyl acetate, and the resulting mixture was washed with water and brine. The obtained organic layer was dried over magnesium sulfate and concentrated under reduced pressure. A half of the obtained residue and Compound 5 (135 mg, 0.518 mmol) was dissolved in DMF (1 mL), and 60% NaH (21 mg, 0.518 mmol) was added thereto, and the reaction mixture was stirred at room temperature for approximately 2 hours. To the reaction mixture was added ethyl acetate, and the resulting mixture was washed with water and brine. The obtained organic layer was dried over magnesium sulfate and concentrated under reduced pressure. To the obtained residue were added ethanol (2 mL), 2 M aqueous solution of potassium carbonate (518 µL, 1.04 mmol), Compound 6 (93 mg, 0.449 mmol) and PdCl$_2$ (dtbpf) (22.5 mg, 0.035 mmol), and the reaction mixture was stirred with heating at 60° C. for approximately 2 hours. To the reaction mixture was added ethyl acetate, and the resulting mixture was washed with water and brine. The obtained organic layer was dried over magnesium sulfate and concentrated under reduced pressure. The obtained residue was purified by silica gel column chromatography to obtain Compound 7 (76.8 mg, 30.6%).
Compound 7;
Method B
  LC/MS retention time=3.44 min.
  MS (ESI) m/z=726.25 (M+H)$^+$.

Compound 7 (76.8 mg, 0.106 mmol) was dissolved in chloroform (1 mL), and trifluoroacetic acid (1 mL) was added thereto, and the reaction mixture was stirred at room temperature over night. Thereafter, the solvent was removed under reduced pressure, and the obtained residue was made basic with 2N aqueous solution of sodium hydroxide, and methanol was added thereto, and the resulting mixture was stirred at room temperature. The mixture was acidized with 2N aqueous solution of hydrochloric acid, and then extracted with a mixture of chloroform and methanol. The obtained organic layer was dried over magnesium sulfate and concentrated under reduced pressure. The obtained residue was purified by reverse-phase chromatography to obtain Compound (I-1-1) (26.3 mg, 51.6%).

Compound (I-1-1); (MeOD) δ: 3.20 (4H, t, J=4.8 Hz), 3.61 (1H, t, J=8.7 Hz), 3.85-3.92 (5H, m), 4.08 (1H, dd, J=10.5, 5.0 Hz), 4.17-4.29 (2H, m), 4.44 (1H, t, J=5.1 Hz), 4.98 (1H, t, J=5.4 Hz), 5.38 (1H, td, J=5.3, 3.3 Hz), 7.02 (2H, d, J=8.8 Hz), 7.29 (1H, s), 7.34 (3H, t, J=8.0 Hz).
Method B
LC/MS retention time=1.77 min.
MS (ESI) m/z=482.00 (M+H)⁺.

Example 2

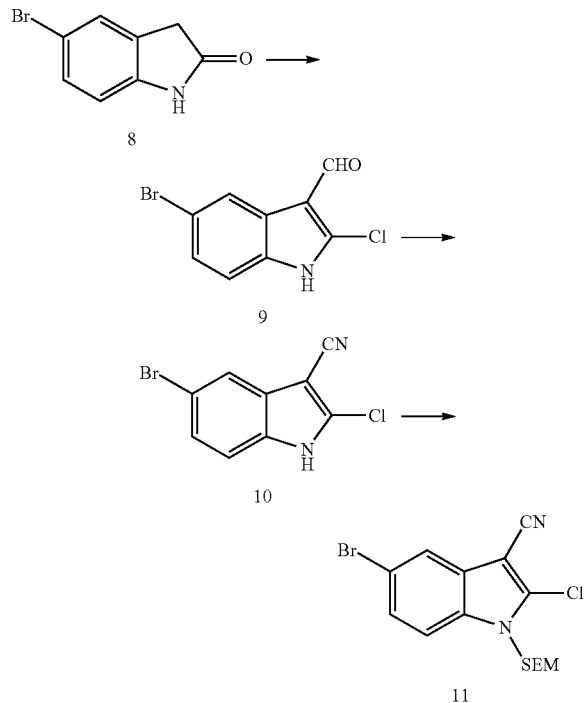

To a solution of DMF (5 mL) and dichloromethane (5 mL) was added POCl₃ (5 mL) at room temperature, and the mixture was stirred for 10 minutes. Thereafter, a suspention of 5-bromooxyindole 8 (2.55 g, 12 mmol) in dichloromethane (12.5 mL)/pyridine (2.5 mL) was added thereto, and the reaction mixture was stirred at room temperature for approximately 2 hours and then at 40° C. for approximately 4 hours. The reaction mixture was treated with iced water and concentrated under reduced pressure. The precipitated solid was filtered. The precipitated solid from the filtrate was filtered to obtain Compound 9 (819.5 mg, 26.4%).
Compound 9;
Method B
LC/MS retention time=1.80 min.
MS (ESI) m/z=259.75 (M+H)⁺.

To Compound 9 (100 mg, 0.387 mmol) were added pyridine (1 mL) and hydroxylamine hydrochloride (29.6 mg, 0.426 mmol), and the mixture was stirred at room temperature for approximately an hour. Thereafter, acetic anhydride (160 μL, 1.7 mmol) was added thereto, and the reaction mixture was stirred with heating at 80° C. for approximately 2 hours. The mixture was cooled to room temperature, diluted with ethyl acetate, and washed with 2N aqueous solution of hydrochloric acid and water. The obtained organic layer was dried over magnesium sulfate and concentrated under reduced pressure. The obtained residue was purified by silica gel column chromatography to obtain Compound 10 (56 mg, 56.7%).
Compound 10;
Method B
LC/MS retention time=1.99 min.
MS (ESI) m/z=254.80 (M−H)⁻.

Compound 10 (55 mg, 0.215 mmol) was dissolved in DMF (1 mL), and 60% NaH (10.3 mg, 0.258 mmol) was added thereto, and the mixture was stirred at room temperature for 3 minutes. Thereafter, 2-(chloromethoxy)ethyltrimethylsilane (42 μL, 0.237 mmol) was added thereto, and the reaction mixture was stirred at room temperature for 40 minutes. To the reaction mixture was added ethyl acetate, and the resulting mixture was washed with water and brine. The obtained organic layer was dried over magnesium sulfate and concentrated under reduced pressure. The obtained residue was purified by silica gel column chromatography to obtain Compound 11 (47.6 mg, 57.3%).
Method B
LC/MS retention time=2.99 min.
MS (ESI) m/z=388.80 (M+H)⁺.

Example 3

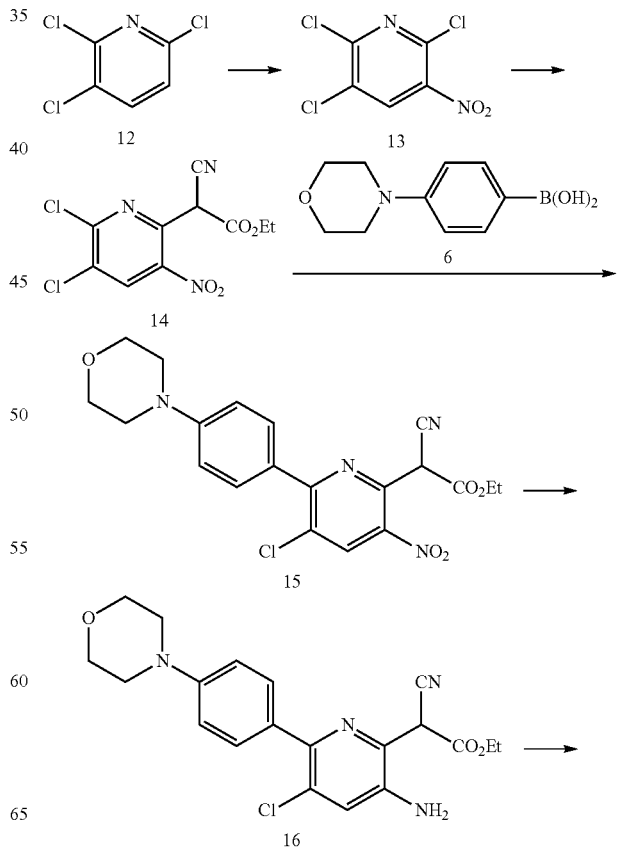

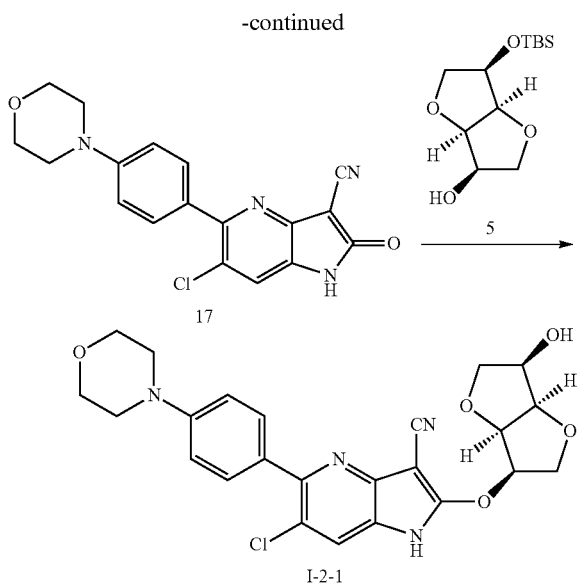

To Compound 12 (5.47 g, 30 mmol) were added nitric acid (30 mL) and concentrated sulfuric acid (24 mL) at room temperature, and the reaction mixture was warmed up to 100° C. and stirred with heating for approximately 8 hours. The reaction mixture was added to iced water, the resulting mixture was stirred. The precipitated solid was filtered to obtain Compound 13 (6.82 g, 64.7%).
Compound 13;
Method B
    LC/MS retention time=2.03 min.
    Ethyl 2-cyanoacetate (2.98 g, 26.4 mmol) was diluted with t-BuOH (60 mL), and t-BuOK (2.96 g, 26.4 mmol) and Compound 13 (3.00 g, 13.2 mmol) were added thereto under ice-cooling, and the reaction mixture was warmed up to room temperature and then stirred. After being stirred for approximately 40 minutes, the reaction mixture was treated with 2N aqueous solution of hydrochloric acid and extracted with ethyl acetate. The organic layer was washed with water and brine, dried over magnesium sulfate, and concentrated under reduced pressure. The obtained residue was purified by silica gel column chromatography to obtain Compound 14 (1.81 g, 32.8%).
Compound 14;
Method B
    LC/MS retention time=2.07 min.
    To Compound 14 (3.90 mmol) were added 1,4-dioxane (30 mL), 2M aqueous solution of potassium carbonate (5.85 mL, 11.7 mmol), Compound 6 (889 mg, 4.29 mmol) and Pd(PPh$_3$)$_4$ (451 mg, 0.390 mmol), and the reaction mixture was stirred with heating at 100° C. To the reaction mixture was added ethyl acetate, and the resulting organic layer was washed with brine. The obtained organic layer was dried over magnesium sulfate and concentrated under reduced pressure. The obtained residue was purified by silica gel column chromatography to obtain Compound 15 (728 mg, 43.3%).
Compound 15;
Method B
    LC/MS retention time=2.28 min.
    MS (ESI) m/z=430.95 (M+H)$^+$.
    To Compound 15 (500 mg, 11.6 mmol) were added 95% ethanol (15 mL) and 5% Pt/C (100 mg), and the reaction mixture was stirred under a hydrogen atmosphere at room temperature. The reaction mixture was diluted with chloroform, dried over magnesium sulfate, filtered with Celite, and concentrated under reduced pressure. The obtained residue was purified by silica gel column chromatography to obtain Compound 16 (228 mg, 49.0%).
Compound 16;
Method B
    LC/MS retention time=2.09 min.
    MS (ESI) m/z=400.95 (M+H)$^+$.
    To Compound 16 (185 mg, 0.462 mmol) were added ethanol (4 mL) and 2N aqueous solution of sodium hydroxide (0.231 mL, 0.462 mmol), and the reaction mixture was stirred with heating under microwave irradiation at 150° C. The reaction mixture was treated with 2N aqueous solution of hydrochloric acid, and a mixture of chloroform and methanol was added thereto. The resulting mixture was dried over magnesium sulfate, filtered and concentrated under reduced pressure to obtain Compound 17 (59.6 mg, 36.4%).
Compound 17;
Method B
    LC/MS retention time=1.32 min.
    MS (ESI) m/z=355.15 (M+H)$^+$.
    To Compound 17 (40.0 mg, 0.113 mmol) was added POCl$_3$ (2.3 mL), and the reaction mixture was stirred with heating at 100° C. and then concentrated under reduced pressure. The obtained residue was treated with chloroform and a saturated aqueous solution of sodium hydrogen carbonate. Thereafter, the mixture was extracted with a mixture of chloroform and methanol, and the organic layer was dried over magnesium sulfate and concentrated under reduced pressure. The obtained residue was dissolved in DMF (1 mL), and 60% NaH (6.4 mg, 0.161 mmol) and 2-(chloromethoxy)ethyl trimethyl silane (29 μL, 0.161 mmol) were added thereto under ice-cooling, and the reaction mixture was stirred. Thereafter, 60% NaH (6.4 mg, 0.161 mmol) and 2-(chloromethoxy)ethyl trimethyl silane (29 μL, 0.161 mmol) were added thereto under ice-cooling, and the mixture was stirred. To the reaction mixture was added ethyl acetate, and the organic layer was washed with water, dried over magnesium sulfate and concentrated under reduced pressure. The obtained residue and Compound 5 (55.7 mg, 0.214 mmol) were dissolved in DMF (1 mL), and 60% NaH (3.9 mg, 0.161 mmol) was added thereto under ice-cooling, and the mixture was stirred. Thereafter, Compound 5 (55.7 mg, 0.214 mmol) and 60% NaH (3.9 mg, 0.161 mmol) were added thereto, and the resulting mixture was stirred. To the reaction mixture, ethyl acetate was added, and the organic layer was washed with water, dried over magnesium sulfate and concentrated under reduced pressure. To the obtained residue was added trifluoroacetic acid (2 ml), and the reaction mixture was stirred at room temperature over night. Thereafter, the solvent was removed under reduced pressure, and the obtained residue was diluted with methanol, and 2N aqueous solution of sodium hydroxide was added thereto, and the resulting mixture was stirred at room temperature. The mixture was acidized with 2N aqueous solution of hydrochloric acid, and then extracted with a mixture of chloroform and methanol. The obtained organic layer was dried over magnesium sulfate and concentrated under reduced pressure. The obtained residue was purified by silica gel column chromatography to obtain Compound (I-2-1) (26.3 mg, 51.6%).
Compound (I-2-1);
Method B
    LC/MS retention time=1.77 min.
    MS (ESI) m/z=483.00 (M+H)$^+$.

¹H-NMR (MeOD) δ: 3.23-3.27 (4H, m), 3.61 (1H, t, J=8.8 Hz), 3.85-3.94 (5H, m), 4.06-4.12 (1H, m), 4.23-4.31 (2H, m), 4.45 (1H, t, J=5.1 Hz), 5.03 (1H, t, J=5.5 Hz), 5.46-5.51 (1H, m), 7.07 (2H, d, J=9.0 Hz), 7.60 (2H, d, J=8.8 Hz), 7.75 (1H, s).

Example 4

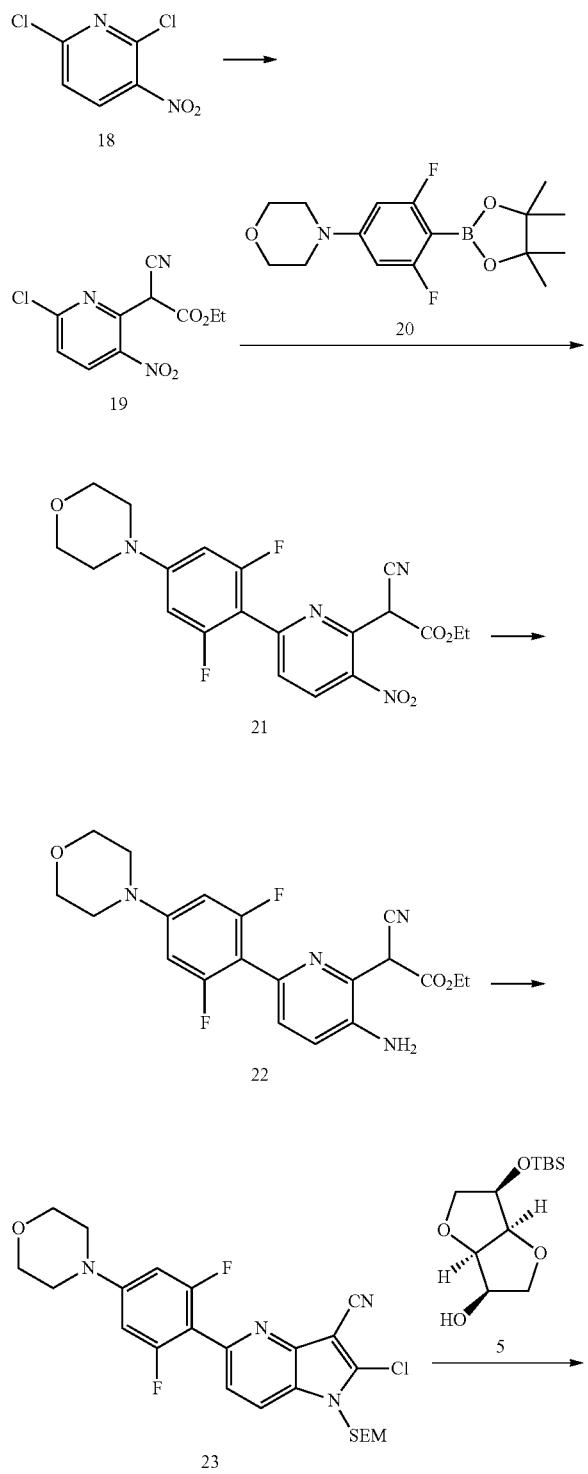

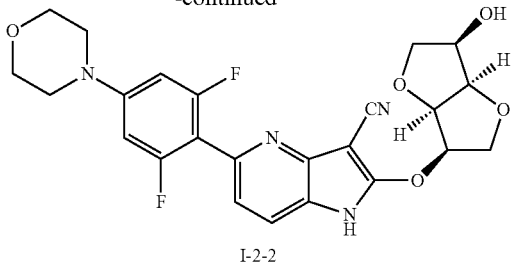

I-2-2

To t-BuOH (12.5 mL) was added t-BuOK (1.12 g, 10 mmol) at room temperature, and ethyl 2-cyanoacetate (1.13 g, 10 mmol) and a solution of Compound 18 (0.965 g, 5 mmol) in t-BuOH (12.5 mL) were added thereto under ice-cooling, and the reaction mixture was warmed up to room temperature and stirred. The solvent was removed under reduced pressure, and the obtained residue was treated with 2N aqueous solution of hydrochloric acid and extracted with ethyl acetate. The obtained organic layer was dried over magnesium sulfate and concentrated under reduced pressure. The obtained residue was purified by silica gel column chromatography to obtain Compound 19 (1.18 g, 87.2%).
Compound 19;
Method B
  LC/MS retention time=1.79 min.
  MS (ESI) m/z=269.80 (M+H)⁺.

To Compound 19 (929 mg, 3.45 mmol) was added 1,4-dioxane (20 mL), and the mixture was warmed up to 100° C., and 2M aqueous solution of potassium carbonate (5.17 mL, 10.3 mmol), PdCl₂ (dtbpf) (225 mg, 0.345 mmol) and Compound 20 (1344 mg, 4.13 mmol) were added thereto, and the resulting mixture was stirred with heating at 100° C. To the reaction mixture was added ethyl acetate, and the organic layer was washed with brine. The obtained organic layer was dried over magnesium sulfate and the solvent was removed under reduced pressure. The obtained residue was purified by silica gel column chromatography to obtain Compound 21 (1056 mg, 70.9%).
Compound 21;
Method B
  LC/MS retention time=2.10 min.

To Compound 21 (800 mg, 1.85 mmol) were added 95% ethanol (16 mL) and 5% Pd/C (160 mg), and the reaction mixture was stirred under a hydrogen atmosphere at room temperature. The reaction mixture was diluted with chloroform, dried over magnesium sulfate, filtered with Celite, and concentrated under reduced pressure. The obtained residue was purified by silica gel column chromatography to obtain Compound 22 (341 mg, 45.5%).
Compound 22;
Method B
  LC/MS retention time=1.98 min.

To Compound 22 (250 mg, 0.621 mmol) was added ethanol (4.5 mL), and the reaction mixture was stirred with heating under microwave irradiation at 150° C. After completion of the reaction, insolubles was collected by filtration. To the filtrate was added POCl₃ (2.0 mL), and the mixture was stirred with heating at 100° C. and concentrated under reduced pressure. The obtained residue was treated with ethyl acetate and a saturated aqueous solution of sodium hydrogen carbonate. Thereafter, the mixture was extracted with a mixture of chloroform and methanol, and the organic layer was dried over magnesium sulfate and concentrated under reduced pressure. The obtained residue was dissolved in DMF (4 mL), and 60% NaH (27.2 mg, 0.680 mmol) and 2-(chloromethoxy)ethyl trimethyl silane (121 μL, 0.680 mmol) were added thereto under ice-cooling, and the mixture was stirred. To the reaction mixture was added ethyl acetate, and the organic layer was washed with water and a saturated aqueous solution of ammonium chloride. The obtained organic layer was dried over magnesium sulfate and concentrated under reduced pressure. The obtained residue was purified by silica gel column chromatography to obtain Compound 23 (130 mg, 56.7%).

Compound 23;
Method B
LC/MS retention time=2.75 min.
MS (ESI) m/z=505.05 (M+H)$^+$.

Compound 5 (27.1 mg, 0.104 mmol) was dissolved in DMF (0.5 mL), and 60% NaH (3.9 mg, 0.161 mmol) was added thereto, and the mixture was stirred at room temperature. Thereafter, Compound 23 (35 mg, 0.069 mmol) was added thereto under ice-cooling, and the reaction mixture was stirred. To the reaction mixture was added ethyl acetate, and the organic layer was washed with water and brine, dried over magnesium sulfate, and concentrated under reduced pressure. To the obtained residue was added trifluoroacetic acid (1 ml), and the reaction mixture was stirred at room temperature over night. Thereafter, the solvent was removed under reduced pressure, and the obtained residue was diluted with methanol, and 2N aqueous solution of sodium hydroxide was added thereto, and the mixture was stirred at room temperature. The resulting mixture was acidized with 2N aqueous solution of hydrochloric acid, and then extracted with a mixture of chloroform and methanol. The obtained organic layer was dried over magnesium sulfate and concentrated under reduced pressure. The obtained residue was purified by silica gel column chromatography to obtain Compound (I-2-2) (32.8 mg, 97.7%).

Compound (I-2-2);
Method B
LC/MS retention time=1.39 min.
MS (ESI) m/z=485.30 (M+H)$^+$.
$^1$H-NMR (MeOD) δ: 3.26-3.30 (OH, m), 3.57-3.64 (1H, m), 3.80-3.86 (4H, m), 3.87-3.92 (1H, m), 4.08 (1H, dd, J=10.8, 4.8 Hz), 4.22-4.30 (2H, m), 4.45 (1H, t, J=5.1 Hz), 5.03 (1H, t, J=5.4 Hz), 5.48-5.54 (1H, m), 6.69 (2H, d, J=11.8 Hz), 7.33 (1H, d, J=8.3 Hz), 7.88 (1H, d, J=8.3 Hz).

Example 5

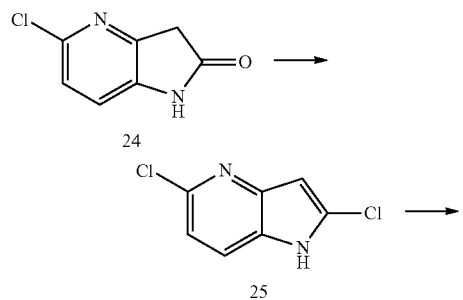

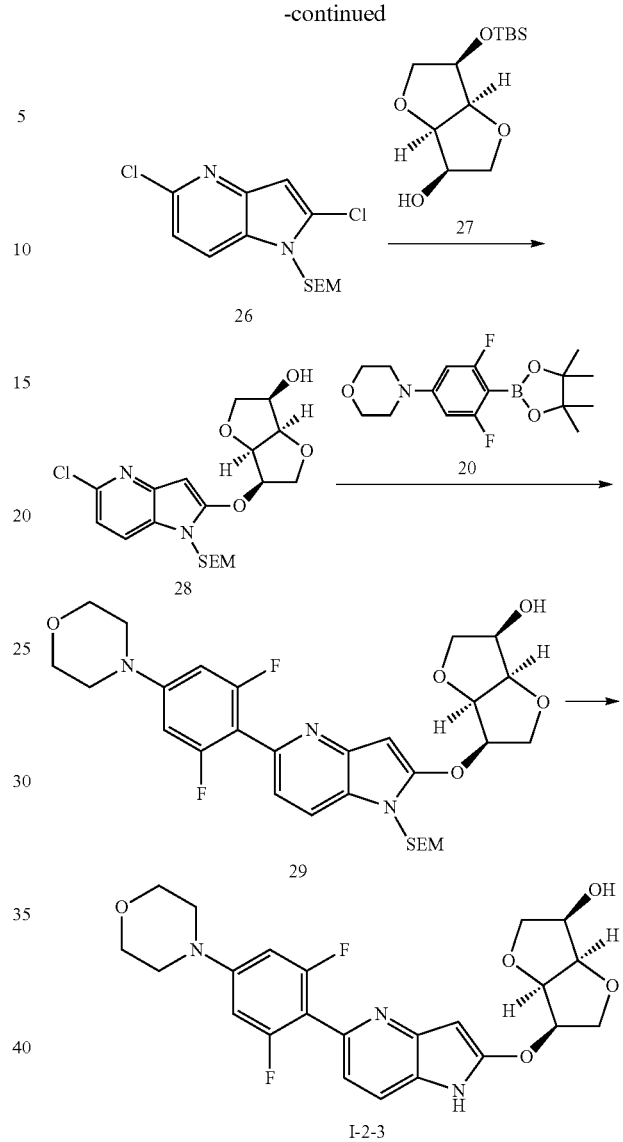

To Compound 24 (5.00 g, 29.7 mmol) were added 1,2-dichloroethane (100 mL), POCl$_3$ (5.51 mL, 59.3 mmol) and pyridine (2.64 mL, 32.6 mmol), the reaction mixture was stirred with heating at 80° C. After completion of the reaction, the reaction mixture was treated with water. The aqueous layer was washed with a mixture of chloroform and methanol, and filtered with Celite. The obtained aqueous layer was neutralized with 2 M aqueous solution of potassium carbonate. The precipitated solid was filtered. The precipitated solid was suspended by adding methanol and filtered again. The filtrate was extracted with a mixture of chloroform and methanol, and the organic layer was dried over magnesium sulfate and concentrated under reduced pressure. The obtained residue and the above collected solids were combined to obtain Compound 25 (3.00 g, 54.1%).

Compound 25;
Method B
LC/MS retention time=1.45 min.
MS (ESI) m/z=187.00 (M+H)$^+$.

Compound 25 (2.95 g, 15.8 mmol) was dissolved in DMF (30 mL), and 60% NaH (757 mg, 18.9 mmol) and 2-(chloromethoxy)ethyl trimethyl silane (3.08 mL, 17.4 mmol) were added thereto under ice-cooling, and the reaction mixture was stirred. To the reaction mixture was added ethyl acetate, and the organic layer was washed with water. The obtained organic layer was dried over magnesium sulfate and concentrated under reduced pressure. The obtained residue was purified by silica gel column chromatography to obtain Compound 26 (4.30 g, 85.9%).

Compound 26;
Method B
LC/MS retention time=2.73 min.
MS (ESI) m/z=316.90 (M+H)$^+$.

To Compound 27 (4.61 g, 31.5 mmol) were added a solution of Compound 26 (1.00 g, 3.15 mmol) in DMF (8 mL). 60% NaH (378 mg, 9.46 mmol) was added thereto under nitrogen atmosphere, and the reaction mixture was stirred at room temperature. Thereafter, the obtained reaction mixture was stirred with heating under microwave irradiation at 150° C. for 2 hours. To the reaction mixture was added ethyl acetate, and the organic layer was washed with 2N aqueous solution of hydrochloric acid and water. The obtained organic layer was dried over magnesium sulfate and concentrated under reduced pressure. The obtained residue was purified by silica gel column chromatography to obtain Compound 28 (877 mg, 65.2%).

Compound 28;
Method B
LC/MS retention time=2.12 min.
MS (ESI) m/z=427.00 (M+H)$^+$.

To Compound 28 (140 mg, 0.328 mmol) was added 1,4-dioxane (4 mL), and the mixture was warmed up to 100° C., and 2 M aqueous solution of potassium carbonate (0.492 mL, 0.984 mmol), PdCl$_2$ (dtbpf) (21.4 mg, 0.033 mmol) and Compound 20 (213 mg, 0.656 mmol) were added thereto, and the reaction mixture was stirred with heating at 100° C. Until Compound 28 disappeared, the reaction mixture was stirred with heating by addition of PdCl$_2$ (dtbpf) and Compound 20. To the reaction mixture was added ethyl acetate, and the organic layer was washed with brine. The obtained organic layer was dried over magnesium sulfate and concentrated under reduced pressure. The obtained residue was purified by silica gel column chromatography to obtain Compound 29 (84.2 mg, 43.5%).

Compound 29;
Method B
LC/MS retention time=1.61 min.
MS (ESI) m/z=590.20 (M+H)$^+$.

To Compound 29 (60 mg, 0.102 mmol) was added trifluoroacetic acid (1 ml), and the reaction mixture was stirred at room temperature over night. Thereafter, the solvent was removed under reduced pressure, and the obtained residue was diluted with chloroform and then added to a saturated aqueous solution of sodium hydrogen carbonate, and the resulting mixture was stirred. Thereafter, methanol was added thereto, and the resulting mixture was stirred at room temperature, and extracted with a mixture of chloroform and methanol. The obtained organic layer was dried over magnesium sulfate and concentrated under reduced pressure. The obtained residue was purified by silica gel column chromatography to obtain Compound (I-2-3) (31.6 mg, 67.6%).

Compound (I-2-3);
Method B
LC/MS retention time=0.96 min.
MS (ESI) m/z=460.30 (M+H)$^+$.
$^1$H-NMR (MeOD) δ: 3.22-3.26 (4H, m), 3.64 (1H, t, J=8.4 Hz), 3.82-3.87 (4H, m), 3.95 (1H, dd, J=8.3, 6.8 Hz), 4.03 (1H, dd, J=9.5, 6.0 Hz), 4.21 (1H, dd, J=9.7, 6.1 Hz), 4.29-4.34 (1H, m), 5.04-5.10 (1H, m), 5.86 (1H, s), 6.63 (2H, d, J=11.3 Hz), 7.06 (1H, d, J=8.0 Hz), 7.59 (1H, d, J=8.0 Hz).

Example 6

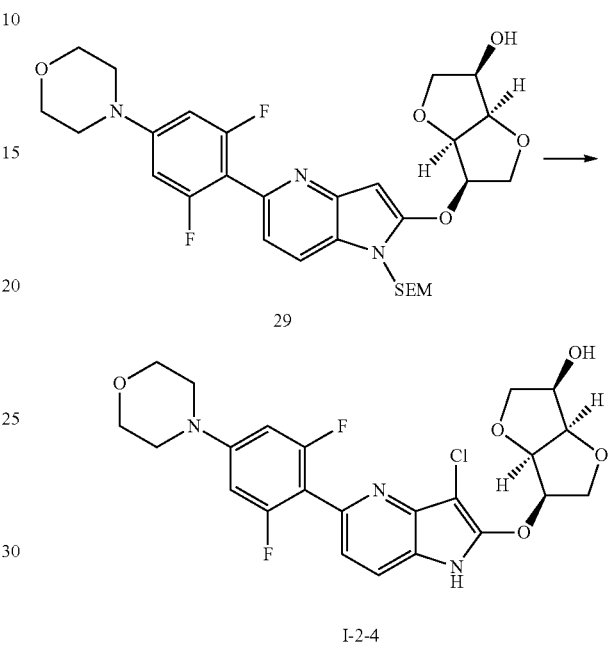

Compound 29 (60 mg, 0.102 mmol) was dissolved in DMF (0.6 mL), and NCS (14.7 mg, 0.11 mmol) was added thereto, and the reaction mixture was stirred at room temperature. To the reaction mixture was added ethyl acetate, and the organic layer was washed with water. The obtained organic layer was dried over magnesium sulfate and concentrated under reduced pressure. To the obtained residue was added trifluoroacetic acid (1 ml), and the reaction mixture was stirred at room temperature over night. Thereafter, the solvent was removed under reduced pressure, and the obtained residue was diluted with chloroform and then added to a saturated aqueous solution of sodium hydrogen carbonate, and the resulting mixture was stirred. Thereafter, methanol was added thereto, and the resulting mixture was stirred, and extracted with a mixture of chloroform and methanol. The obtained organic layer was dried over magnesium sulfate and concentrated under reduced pressure. The obtained residue was purified by silica gel column chromatography to obtain Compound (I-2-4) (42.3 mg, 84.0%).

Compound (I-2-4);
Method B
LC/MS retention time=1.10 min.
MS (ESI) m/z=494.05 (M+H)$^+$.
$^1$H-NMR (MeOD) δ: 3.23-3.28 (4H, m), 3.71 (1H, t, J=8.7 Hz), 3.82-3.87 (4H, m), 3.93-3.99 (1H, m), 4.09-4.17 (2H, m), 4.25-4.32 (1H, m), 4.47 (1H, t, J=5.1 Hz), 5.31-5.38 (1H, m), 6.65 (2H, d, J=10.8 Hz), 7.11-7.18 (1H, m), 7.69 (1H, d, J=8.3 Hz).

Example 7

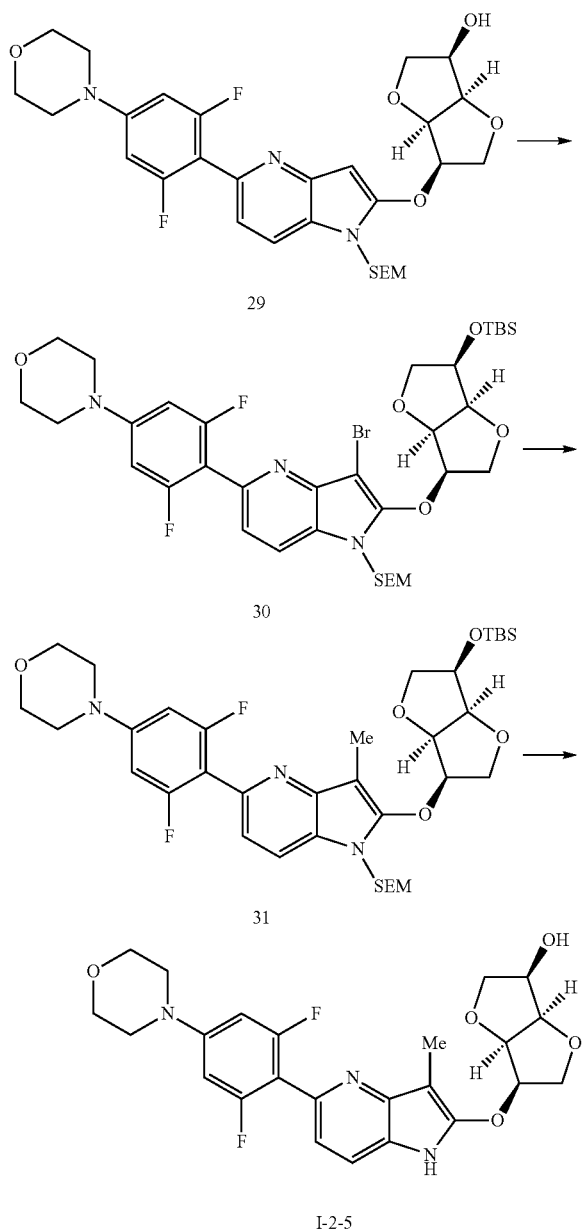

Compound 29 (135 mg, 0.229 mmol) was dissolved in DMF (2.7 mL), and NBS (40.7 mg, 0.229 mmol) was added thereto, and the reaction mixture was stirred at room temperature. To the reaction mixture was added ethyl acetate, and the organic layer was washed with water. The obtained organic layer was dried over magnesium sulfate and concentrated under reduced pressure. The obtained residue was dissolved in DMF (0.5 mL), and a solution of tert-Butyldimethylsilyl Chloride (51.8 mg, 0.344 mmol) in imidazole (23.4 mg, 0.344 mmol) and DMF (1.0 mL) was added thereto, and the reaction mixture was stirred at room temperature. On the way, imidazole (the amount of ⅓ of the amount of initial addition) and tert-Butyldimethylsilyl Chloride (the amount of ⅓ of the amount of initial addition) were added thereto, and the resulting mixture was stirred at room temperature. To the reaction mixture was added ethyl acetate, and the organic layer was washed with water. The obtained organic layer was dried over magnesium sulfate and concentrated under reduced pressure. The obtained residue was purified by silica gel column chromatography to obtain Compound 30 (124.3 mg, 69.3%).

Compound 30;
Method B
LC/MS retention time=3.34 min.

Compound 30 (50 mg, 0.064 mmol) was dissolved in THF (0.5 mL), and the reaction mixture was cooled to −78° C., and a solution of n-BuLi in hexane (1.58 M, 0.044 mL, 0.070 mmol) was added thereto, and the reaction mixture was stirred for a few minutes. Thereafter, a solution of MeI (0.016 mL, 0.255 mmol) in THF (0.1 mL) was added thereto, and the reaction mixture was stirred at −78° C. A solution of n-BuLi in hexane (1.58 M, 0.044 mL, 0.070 mmol) was added thereto, and the resulting mixture was stirred at −78° C. Thereafter, to the reaction mixture was added a saturated aqueous solution of ammonium chloride and extracted with ethyl acetate. The organic layer was washed with water, dried over magnesium sulfate and concentrated under reduced pressure. The obtained residue was purified by silica gel column chromatography to obtain Compound 31 (22.9 mg, 49.9%).

Compound 31;
Method B
LC/MS retention time=2.69 min.

To Compound 31 (22 mg, 0.031 mmol) was added trifluoroacetic acid (1 ml), and the reaction mixture was stirred at room temperature over night. Thereafter, the solvent was removed under reduced pressure, and the obtained residue was diluted with chloroform and then added to a saturated aqueous solution of sodium hydrogen carbonate, and the resulting mixture was stirred. Thereafter, methanol was added thereto, and the resulting mixture was stirred at room temperature, and extracted with chloroform. The obtained organic layer was dried over magnesium sulfate and concentrated under reduced pressure. The obtained residue was purified by silica gel column chromatography to obtain Compound (I-2-5) (14.3 mg, 98.6%).

Compound (I-2-5);
LC/MS retention time=1.01 min.
MS (ESI) m/z=474.05 (M+H)$^+$.

Example 8

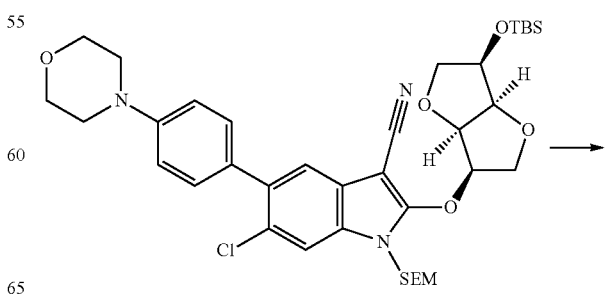

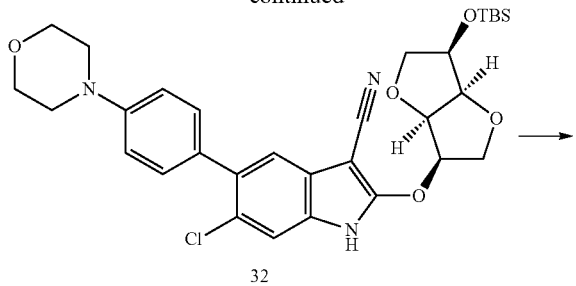

32

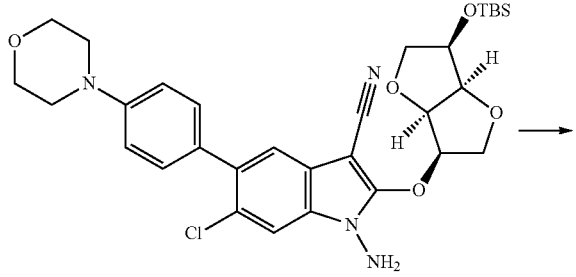

33

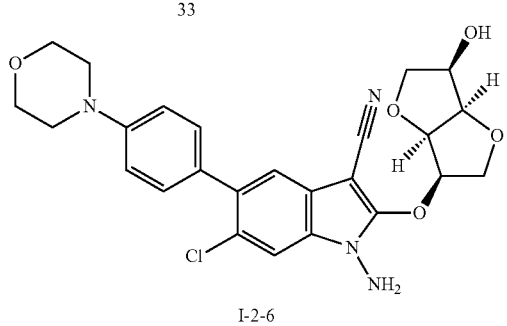

I-2-6

To a solution of Compound 7 (300 mg, 0.413 mmol) in dichloromethane (1.5 mL) was added TFA (30.5 mg, 0.310 mmol) at 0° C., and the reaction mixture was stirred at room temperature for 30 minutes. The reaction mixture was quenched with 2N aqueous solution of sodium hydroxide and extracted with ethyl acetate. The organic layer was concentrated under reduced pressure. The obtained residue was purified by silica gel column chromatography to obtain Compound 32 (113 mg, 0.189 mmol, 46%) as a white solid.

Compound 32; $^1$H-NMR (CDCl$_3$) δ: 0.13-0.14 (m, 6H), 0.93 (s, 9H), 3.24 (s, 4H), 3.69 (t, J=8.2 Hz, 1H), 3.90-3.93 (m, 5H), 4.09-4.11 (m, 1H), 4.19-4.22 (m, 1H), 4.33-4.35 (m, 1H), 4.42 (s, 1H), 4.93 (s, 1H), 5.36-5.37 (m, 1H), 6.96-6.98 (m, 2H), 7.35-7.37 (m, 3H), 7.48 (s, 1H), 8.51 (s, 1H).

To a solution of Compound 32 (84.9 mg, 0.142 mmol) in DMF (0.5 ml) was added NaH (8.0 mg, 0.199 mmol) at room temperature, and the reaction mixture was stirred for 10 minutes. O-(diphenylphosphinyl)hydroxylamine (46.5 mg, 0.199 mmol) was added thereto, and the reaction mixture was stirred at room temperature over night. The reaction mixture was quenched with water and extracted with ethyl acetate. The organic layer was concentrated under reduced pressure to obtain a crude product of Compound 33. The obtained crude product (69.2 mg) was used for the following reaction.

To a solution of the crude product (69.2 mg) in THF (0.35 mL) was added 1M TBAF/THF (0.226 mL, 0.226 mmol), and the reaction mixture was stirred at room temperature for an hour. The reaction mixture was purified by silica gel column chromatography and then solidified with hexane/ethyl acetate to obtain Compound (I-2-6) (12.6 mg, 0.113 mmol, 22% in 2 steps) as an orange solid.

Compound (I-2-6); $^1$H-NMR (CDCl$_3$) δ: 2.75-2.77 (m, 1H), 3.23 (s, 4H), 3.84-3.87 (m, 1H), 3.89 (s, 4H), 3.94-3.96 (m, 1H), 4.31-4.32 (m, 3H), 4.65-4.67 (m, 1H), 4.77 (s, 2H), 4.81-4.83 (m, 1H), 5.62 (d, J=4.5 Hz, 1H), 6.97 (d, J=8.5 Hz, 2H), 7.38 (d, J=8.3 Hz, 2H), 7.48 (s, 1H), 7.58 (s, 1H).

Example 9

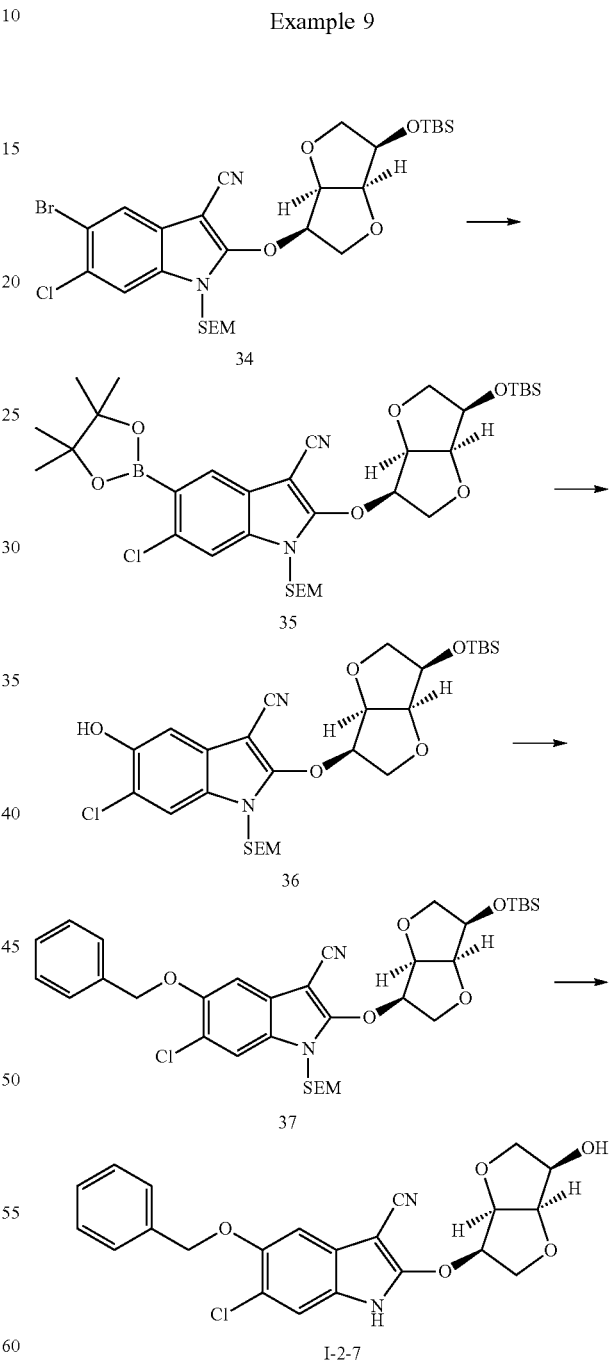

To a solution of Compound 34 (50.0 mg, 0.078 mmol) in dioxane (0.5 mL) were successively added PdCl$_2$(dppf).CH$_2$Cl$_2$ (6.3 mg, 7.8 nmol), Bis(pinacolato)diboron (29.6 mg, 0.116 mmol) and potassium acetate (30.5 mg, 0.310 mmol) at room temperature, and the reaction mixture was stirred at 100° C. for 2 hours. The solvent was removed under reduced pressure to obtain a crude product of Compound 35. The obtained crude product (47.1 mg) was used for the following reaction.

To a solution of the crude product (47.1 mg) in THF (0.5 ml) were added hydrogen peroxide solution (30%, 8.35 μl, 0.082 mmol) and 2N aqueous solution of sodium hydroxide (41 μl, 0.082 mmol) at 0° C., and the reaction mixture was stirred at 0° C. for 1.5 hours. The reaction mixture was quenched with a saturated aqueous solution of ammonium chloride and extracted with ethyl acetate. The organic layer was concentrated under reduced pressure. The obtained residue was purified by silica gel column chromatography to obtain Compound 36 (20.7 mg, 0.036 mmol, 46% in 2 steps) as a colorless oil.

To Compound 37 (24.9 mg) was added 1M TBAF/THF (0.517 mL, 0.517 mmol), and the reaction mixture was stirred with heating at 80° C. for 3 hours. The reaction mixture was purified by silica gel column chromatography and then solidified with hexane/ethyl acetate to obtain Compound (I-2-7) (4.3 mg, 0.010 mmol, 29% in 2 steps) as a white solid.

Compound (I-2-7); $^{1}$H-NMR (DMSO-D6) δ: 3.41 (t, J=8.7 Hz, 1H), 3.76 (t, J=7.5 Hz, 1H), 4.01-4.11 (m, 3H), 4.32 (t, J=5.0 Hz, 1H), 4.84 (t, J=5.3 Hz, 1H), 5.03 (d, J=6.8 Hz, 1H), 5.24-5.26 (m, 3H), 7.16 (s, 1H), 7.33-7.34 (m, 2H), 7.41 (t, J=7.4 Hz, 2H), 7.50 (d, J=7.3 Hz, 2H).

Example 10

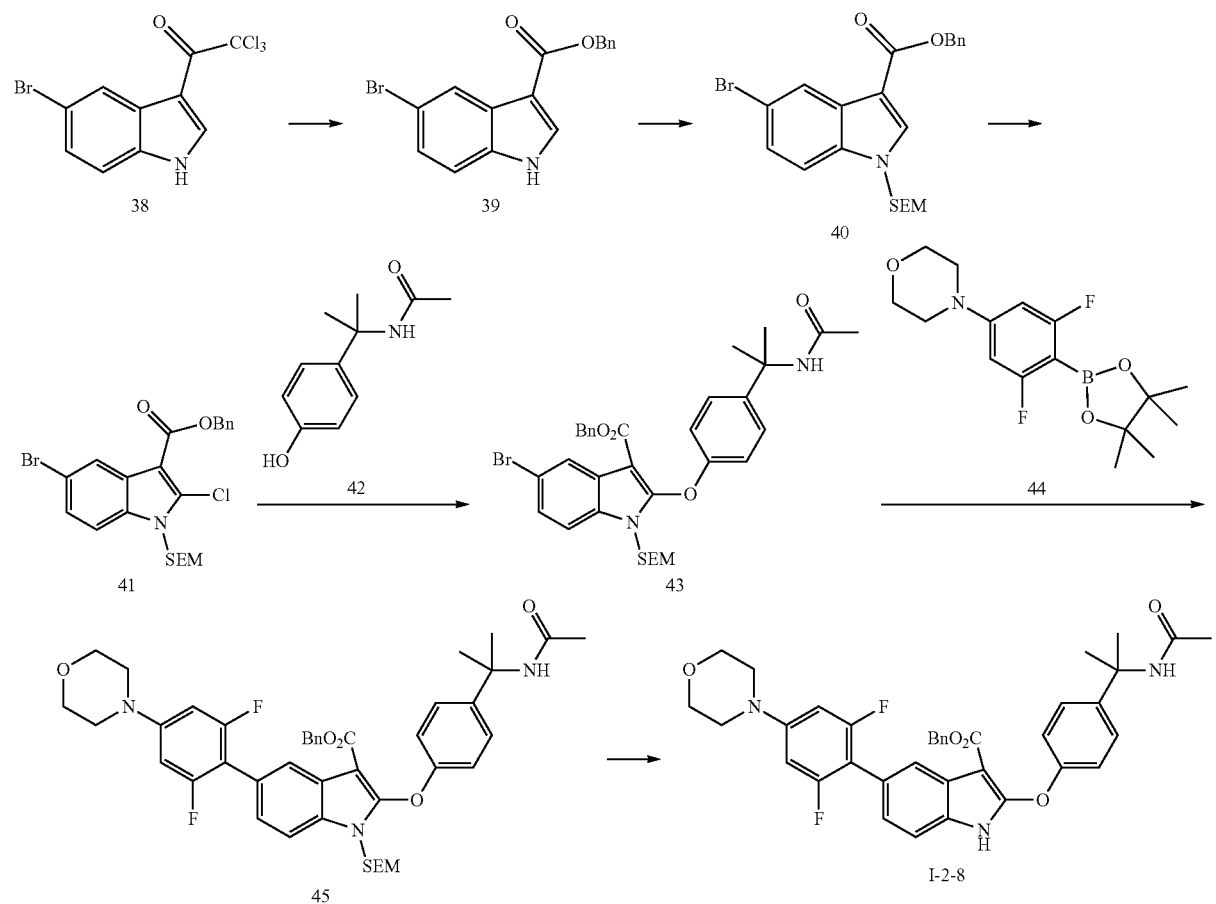

Compound 36; $^{1}$H-NMR (DMSO-D6) δ: −0.07-−0.05 (m, 9H), 0.08-0.09 (m, 6H), 0.80-0.88 (m, 11H), 3.45-3.50 (m, 3H), 3.77 (t, J=7.2 Hz, 1H), 4.01-4.07 (m, 2H), 4.30-4.36 (m, 2H), 4.86 (t, J=5.4 Hz, 1H), 5.35-5.44 (m, 3H), 6.95 (s, 1H), 7.54 (s, 1H), 9.96 (s, 1H).

To a solution of Compound 36 (20.7 mg, 0.036 mmol) in THF (0.4 mL) were successively added benzyl alcohol (5.4 μg, 0.0052 mmol), triphenylphosphine (13.6 mg, 0.052 mmol) and DIAD (10.1 μl, 0.052 mmol), and the reaction mixture was stirred at room temperature for an hour. The reaction mixture was passed through silica gel, and obtained Compound 37 (24.9 mg) was used for the following reaction.

To a solution of Compound 38 (4.72 g, 13.8 mmol) in N,N-dimethylformamide (24 mL) were successively added benzyl alcohol (4.48 g, 41.5 mmol) and NaH (0.829 g, 60% Wt, 20.7 mmol), and the reaction mixture was stirred at 50° C. for 3 hours. Thereafter, to the reaction mixture were added a saturated aqueous solution of ammonium chloride and ethyl acetate, and the resulting mixture was extracted. The organic layer was washed with brine, dried over sodium sulfate and concentrated under reduced pressure. The obtained residue was purified by silica gel column chromatography to obtain Compound 39 (4.0 g, 12.1 mmol, 88%) as a light yellow solid.

Compound 39; $^{1}$H-NMR (DMSO-d6) δ: 5.33 (s, 2H), 7.31-7.48 (m, 7H), 8.10 (s, 1H), 8.18 (s, 1H).

To a solution of Compound 39 (5.0 g, 15.1 mmol) in N,N-dimethylformamide (50 mL) was added NaH (100 mg, 2.50 mmol) at 0° C., and the reaction mixture was stirred for 30 minutes. Thereafter, to the reaction suspension was added 2-(chloromethoxy)ethyl trimethyl silane (3.22 mL, 18.2 mmol) at 0° C., and the mixture was stirred for an hour. To the reaction mixture were added a saturated aqueous solution of ammonium chloride and ethyl acetate, and the resulting mixture was extracted. The organic layer was washed with brine, dried over sodium sulfate and concentrated under reduced pressure. The obtained residue was purified by silica gel column chromatography to obtain Compound 40 (5.62 g, 12.2 mmol, 81%) as a light yellow solid.

Compound 40; $^1$H-NMR (CDCl$_3$) δ: −0.06 (s, 9H), 0.87 (t, J=8.0 Hz, 2H), 3.45 (t, J=8.0 Hz, 2H), 5.39 (s, 2H), 5.46 (s, 2H), 7.34-7.49 (m, 7H), 7.88 (s, 1H), 8.35 (s, 1H).

To a solution of Compound 40 (5.82 g, 12.6 mmol) in THF (100 mL) was added 1.0 M lithium hexadisilazide in THF (27.8 mL, 27.8 mmol) at −78° C., and the reaction mixture was stirred for 10 minutes. Thereafter, to the reaction suspension was added 1,1,1,2,2,2-hexachloroethane (8.98 g, 37.9 mmol) at −78° C., the mixture was warmed up to room temperature and stirred an hour. To the reaction mixture were added 1N aqueous solution of hydrochloric acid and ethyl acetate, and the resulting mixture was extracted. The organic layer was washed with brine, dried over sodium sulfate and concentrated under reduced pressure. The obtained residue was purified by silica gel column chromatography to obtain Compound 41 (3.16 g, 6.39 mmol, 51%) as a yellow solid.

Compound 41; $^1$H-NMR (CDCl$_3$) δ: −0.06 (s, 9H), 0.89 (t, J=8.0 Hz, 2H), 3.53 (t, J=8.0 Hz, 2H), 5.44 (s, 2H), 5.60 (s, 2H), 7.34-7.40 (m, 5H), 7.50-7.52 (m, 2H), 8.30 (s, 1H).

To a solution of Compound 41 (1.0 g, 2.0 mmol) in N,N-dimethylformamide (10 mL) were successively added N-(2-(4-hydroxyphenyl)2-propaninacetamide 42 (0.488 g, 2.53 mmol) and NaH (0.101 g, 60% Wt, 2.53 mmol) at 0° C., and the reaction mixture was stirred at room temperature for an hour. Thereafter, to the reaction mixture were added a saturated aqueous solution of ammonium chloride and ethyl acetate, and the resulting mixture was extracted. The organic layer was washed with brine, dried over sodium sulfate and concentrated under reduced pressure to obtain a crude product of Compound 43.

To a solution of the crude product 43 (943 mg, 1.45 mmol) in 1,4-dioxane (9.4 mL) were successively added boronic acid ester 44 (612 mg, 1.88 mmol), PdCl$_2$ (dtbpf) (94 mg, 0.15 mmol), 2M aqueous solution of potassium carbonate (2.21 mL, 4.34 mmol), and the reaction mixture was stirred at 100° C. for 80 minutes. To the reaction mixture were added a saturated aqueous solution of ammonium chloride and ethyl acetate, and the resulting mixture was extracted. The organic layer was dried over sodium sulfate and concentrated under reduced pressure. The obtained residue was purified by silica gel column chromatography to obtain Compound 45 (1.01 g, 1.31 mmol, 91%) as an orange-yellow solid.

Compound 45; $^1$H-NMR (CDCl$_3$) δ: −0.07 (s, 9H), 0.86 (t, J=8.0 Hz, 2H), 1.68 (s, 6H), 1.96 (s, 3H), 3.21 (t, J=4.0 Hz, 4H), 3.50 (t, J=8.0 Hz, 2H), 3.88 (t, J=4.0 Hz, 4H), 5.17 (s, 2H), 5.43 (s, 2H), 5.62 (s, 1H), 6.49-6.52 (m, 2H), 7.19-7.29 (m, 7H), 7.37-7.39 (m, 1H), 7.54-7.56 (m, 1H), 8.30 (s, 1H).

To a solution of Compound 45 (40 mg, 0.052 mmol) in dichloromethane (0.4 mL) was added trifluoroacetic acid (0.3 mL, 4.0 mmol), and the reaction mixture was stirred at room temperature for 2 hours. The solvent of the reaction mixture was removed under reduced pressure. The obtained residue was dissolved in THF (0.6 mL), and 2M aqueous solution of sodium hydroxide (0.6 mL) was successively added thereto, and the reaction mixture was stirred at room temperature for 2 hours. To the reaction mixture were added a saturated aqueous solution of ammonium chloride, chloroform and methanol, and the resulting mixture was extracted. The organic layer was dried over sodium sulfate and concentrated under reduced pressure. The obtained residue was purified by silica gel column chromatography to obtain Compound (I-2-8) (11.5 mg, 0.018 mmol, 35%) as a white solid.

Compound (I-2-8); $^1$H-NMR (DMSO-d6) δ: 1.54 (s, 6H), 1.85 (s, 3H), 3.12 (t, J=4.0 Hz, 4H), 3.74 (t, J=4.0 Hz, 4H), 5.15 (s, 2H), 6.50-6.55 (m, 2H), 6.90-6.94 (m, 2H), 7.07-7.31 (m, 9H), 7.95 (s, 1H).

Example 11

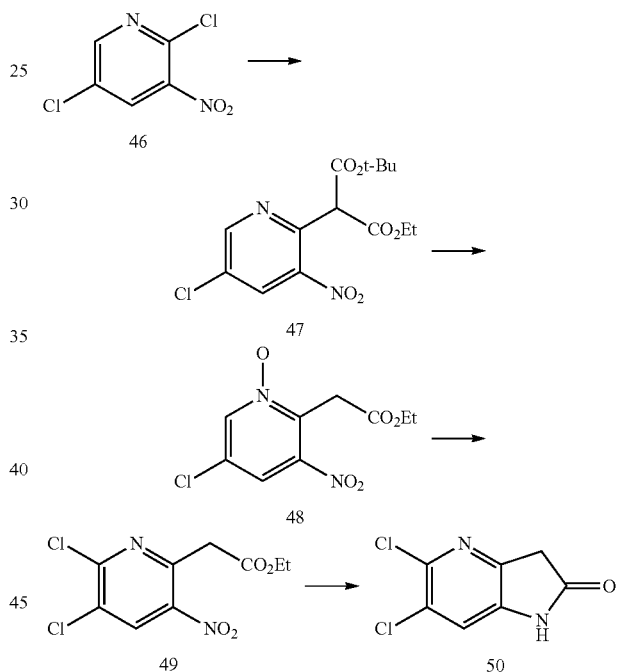

Compound 46 (1.70 g, 8.81 mmol) was dissolved in DMF (17 mL), and t-butyl ethylmalonate (3.34 ml, 17.62 mmol) was added thereto, and the reaction mixture was cooled under ice-cooling. 60% NaH (705 mg, 17.62 mmol) was added thereto and the reaction mixture was stirred at room temperature. After completion of the reaction, the reaction mixture was cooled under ice-cooling, and 2N aqueous solution of hydrochloric acid (10 ml) was added thereto, and the resulting mixture was extracted with ethyl acetate. The organic layer was washed with water, dried over magnesium sulfate and concentrated under reduced pressure. The obtained residue was purified by silica gel column chromatography to obtain Compound 47 (2.69 g, 88.8%). Compound 47; $^1$H-NMR (CDCl$_3$) δ: 1.30 (3H, t, J=7.2 Hz), 1.49 (9H, s), 4.25-4.36 (2H, m), 5.38 (1H, s), 8.46 (1H, s), 8.77 (1H, s).

Compound 47 (1.00 g, 2.90 mmol) was dissolved in chloroform (5 mL) and trifluoroacetic acid (5 ml), and the reaction mixture was stirred at room temperature. After completion of the reaction, the solvent was removed under reduced pressure. The obtained residue was diluted with chloroform, and the resulting mixture was neutralized with 2 M aqueous solution of potassium carbonate. The obtained organic layer was dried over magnesium sulfate and concentrated under reduced pressure. A part of the obtained residue (500 mg) was dissolved in dichloromethane (5 ml), and UHP (385 mg, 4.09 mmol) and anhydride trifluoroacetic acid (0.383 ml, 2.72 mmol) were added thereto, and the reaction mixture was stirred at room temperature. After completion of the reaction, to the reaction mixture was added a saturated aqueous solution of sodium hydrogen carbonate, and the resulting mixture was extracted with chloroform. The obtained residue was purified by silica gel column chromatography to obtain Compound 48 (0.417 g, 76.4%).

Compound 48; $^1$H-NMR (CDCl$_3$) δ: 1.28 (3H, t, J=7.2 Hz), 4.21 (2H, q, J=6.9 Hz), 4.36 (2H, s), 7.89 (1H, s), 8.50 (1H, s).

To Compound 48 (400 mg, 1.53 mmol) were added phosphorus oxychloride (4 ml) and tetrabutylammonium chloride (427 mg, 1.53 mmol), and the reaction mixture was stirred with heating at 70° C. After completion of the reaction, to the reaction mixture was added ice, and the resulting mixture was extracted with diethyl ether. The obtained organic layer was dried over magnesium sulfate and concentrated under reduced pressure. The obtained residue was purified by silica gel column chromatography to obtain Compound 49 (210 mg, 49.2%).

Compound 49; 1H-NMR (CDCl$_3$) δ: 1.27 (3H, t, J=6.9 Hz), 4.19 (2H, q, J=6.9 Hz), 4.28 (2H, s), 8.54 (1H, s).

Compound 49 (38 mg, 0.136 mmol) was diluted with methanol (0.5 ml), and a catalytic amount of 5% Pt/C was added thereto, and the reaction mixture was stirred under a hydrogen atmosphere at room temperature. After completion of the reaction, the reaction mixture was diluted with a mixture of chloroform and methanol, and filtered with Celite. The obtained filtrate was concentrated under reduced pressure. A part of the obtained residue (25 mg) was diluted with DMF (0.5 ml), and potassium t-butoxide (12.4 mg, 0.11 mmol) was added thereto, and the reaction mixture was stirred at room temperature. To the reaction mixture was added 2N aqueous solution of hydrochloric acid (0.11 ml), and the resulting mixture was extracted with ethyl acetate. Thereafter, the organic layer was washed with water, dried over magnesium sulfate and concentrated under reduced pressure to obtain Compound 50 (17.6 mg, 84.1%).
Compound 50;
Method B
 LC/MS retention time=1.21 min.
 MS (ESI) m/z=202.85 (M+H)$^+$.

Example 12

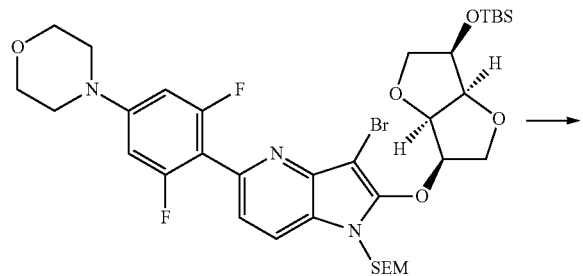

30

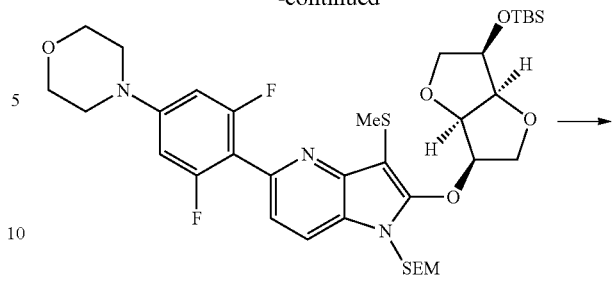

51

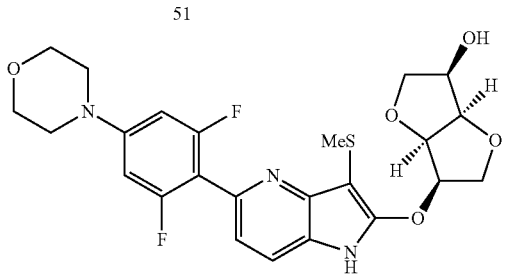

I-3-1

Compound 30 (114.5 mg, 0.146 mmol) was dissolved in THF (1.49 mL), and the mixture was cooled to −78° C., and a solution of n-BuLi in hexane (1.65 M, 0.177 mL, 0.293 mmol) was added thereto, and the reaction mixture was stirred for 20 minutes. Thereafter, 1,2-dimethyldisulfane (0.065 mL, 0.731 mmol) was added thereto, and the reaction mixture was stirred at −78° C. for 30 minutes. After being stirred at −30° C. for 30 minutes, to the reaction mixture was added a saturated aqueous solution of ammonium chloride, and the resulting mixture was extracted with ethyl acetate. The organic layer was washed with water, dried over sodium sulfate and concentrated under reduced pressure. The obtained residue was purified by silica gel column chromatography to obtain Compound 51 (64.0 mg, 58.3%).
Compound 51;
Method A
 LC/MS retention time=3.39 min.
 MS (ESI) m/z=750.30 (M+H)$^+$.

Compound 51 (29.0 mg, 0.039 mmol) was dissolved in CH$_2$Cl$_2$ (0.29 mL), and trifluoroacetic acid (0.29 ml) was added thereto, and the reaction mixture was stirred at room temperature for 4 hours. Thereafter, the solvent was removed under reduced pressure, and the obtained residue was diluted with chloroform. The mixture was added to a saturated aqueous solution of sodium hydrogen carbonate, and the resulting mixture was stirred. Thereafter, methanol was added thereto, and the resulting mixture was stirred at room temperature and extracted with chloroform. The obtained organic layer was dried over sodium sulfate and concentrated under reduced pressure. The obtained residue was purified by silica gel column chromatography to obtain Compound (I-3-1) (14.7 mg, 75.2%). Compound (I-3-1); $^1$H-NMR (DMSO-d6) δ: 2.24 (s, 3H), 3.20 (t, J=4.0 Hz, 4H), 3.75 (m, 5H), 3.93-4.13 (m, 3H), 4.34 (t, J=4.0 Hz, 1H), 4.81 (t, J=4.0 Hz, 1H), 5.02 (d, J=8.0 Hz, 1H), 5.41 (dd, J=12.0, 4.0 Hz, 1H), 6.72 (d, J=12.0 Hz, 2H), 7.04 (d, J=8.0 Hz, 1H), 7.58 (d, J=8.0 Hz, 1H).
Method A
 LC/MS retention time=1.22 min.
 MS (ESI) m/z=506.2 (M+H)$^+$.

Example 13

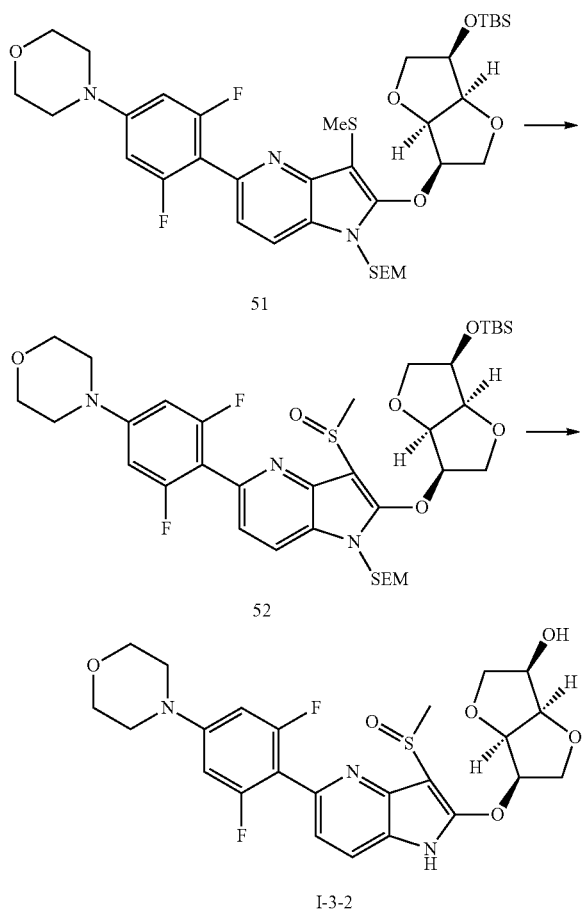

Compound 51 (25.0 mg, 0.033 mmol) was dissolved in CH$_2$Cl$_2$ (0.5 mL), and 77% mCPBA (14.9 mg, 0.067 mmol) was added thereto, and the reaction mixture was stirred for 100 minutes. The reaction mixture was quenched with a saturated aqueous solution of sodium hydrogen carbonate and extracted with ethyl acetate. The solvent was removed under reduced pressure to obtain a crude product of Compound 52. The obtained crude product (29.0 mg) was used for the following reaction.

Compound 52;
Method A
  LC/MS retention time=3.38 min.
  MS (ESI) m/z=766.3 (M+H)$^+$.

The crude product (29.0 mg) was dissolved in CH$_2$Cl$_2$ (0.29 mL), and trifluoroacetic acid (0.29 ml) was added thereto, and the reaction mixture was stirred at room temperature for an hour. Thereafter, the solvent was removed under reduced pressure, and the obtained residue was diluted with chloroform. The mixture was added to a saturated aqueous solution of sodium hydrogen carbonate, and the resulting mixture was stirred. Thereafter, methanol was added thereto, and the resulting mixture was stirred at room temperature and extracted with chloroform. The obtained organic layer was dried over sodium sulfate and concentrated under reduced pressure. The obtained residue was purified by silica gel column chromatography to obtain Compound (I-3-2) (7.5 mg, 38.0%). Compound (I-3-2);

$^1$H-NMR (DMSO-d6) δ: 3.21 (m, 7H), 3.53-3.77 (m, 5H), 3.97-4.14 (m, 3H), 4.30-4.34 (m, 1H), 4.83-4.87 (m, 1H), 5.06-5.08 (m, 1H), 5.24 (s, 1H), 6.73 (d, J=8.0 Hz, 2H), 7.15 (d, J=8.0 Hz, 1H), 7.70 (d, J=8.0 Hz, 1H).
  LC/MS retention time=1.11 min.
  MS (ESI) m/z=521.1 (M+H)$^+$.

Example 14

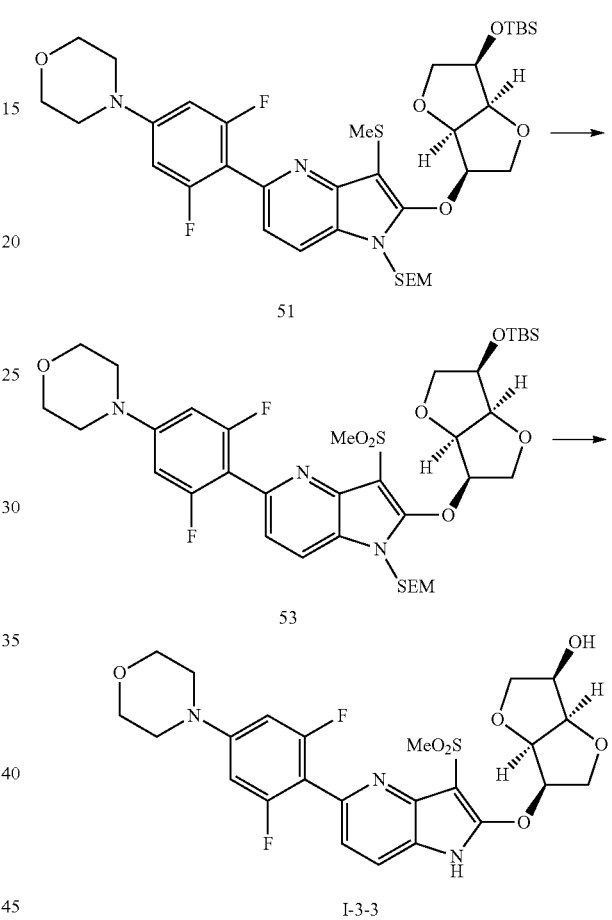

Compound 51 (25.7 mg, 0.034 mmol) was dissolved in CH$_2$Cl$_2$ (0.51 mL), and 77% mCPBA (38.4 mg, 0.172 mmol) was added thereto, and the reaction mixture was stirred at room temperature for 140 minutes. Thereafter, a saturated aqueous solution of sodium bisulfite (0.257 mL, 0.103 mmol) and 28% aqueous solution of ammonia (0.027 mL, 0.343 mmol) were added thereto, and the reaction mixture was stirred at room temperature for 165 minutes. The reaction mixture was extracted with a mixture of chloroform and methanol, and the solvent was removed under reduced pressure to obtain a crude product of Compound 53. The obtained crude product (27.0 mg) was used for the following reaction.

Compound 53;
Method A
  LC/MS retention time=3.46 min.
  MS (ESI) m/z=782.30 (M+H)$^+$.

The crude product (27.0 mg) was dissolved in CH$_2$Cl$_2$ (0.27 mL), and trifluoroacetic acid (0.27 ml) was added thereto, and the reaction mixture was stirred at room temperature for an hour. Thereafter, the solvent was removed under reduced pressure, and the obtained residue was diluted with chloroform. The mixture was added to a saturated aqueous solution of sodium hydrogen carbonate, and the resulting mixture was stirred. Thereafter, methanol was added thereto, and the resulting mixture was stirred at room temperature and extracted with chloroform. The obtained organic layer was dried over sodium sulfate and concentrated under reduced pressure. The obtained residue was purified by silica gel column chromatography to obtain Compound (I-3-3) (14.7 mg, 79.8%). Compound (I-3-3); $^1$H-NMR (DMSO-d6) δ: 2.72 (d, J=8.0 Hz, 1H), 3.26 (s, 3H), 3.27 (t, J=4.0 Hz, 4H), 3.69-3.73 (m, 1H), 3.87 (t, J=4.0 Hz, 4H), 3.95-3.99 (m, 1H), 4.10-4.17 (m, 1H), 4.28-4.35 (m, 2H), 4.59 (t, J=4.0 Hz, 1H), 4.98 (t, J=4.0 Hz, 1H), 5.71 (dd, J=12.0, 8.0 Hz, 1H), 6.52 (d, J=12.0 Hz, 2H), 7.23 (d, J=8.0 Hz, 1H), 7.90 (d, J=8.0 Hz, 1H).

LC/MS retention time=1.30 min.

MS (ESI) m/z=538.1 (M+H)$^+$

Example 15

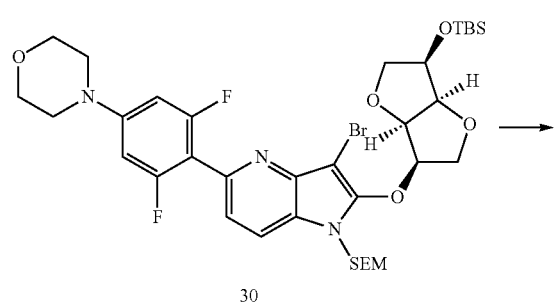

30

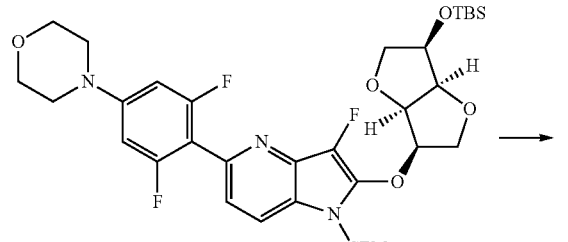

54

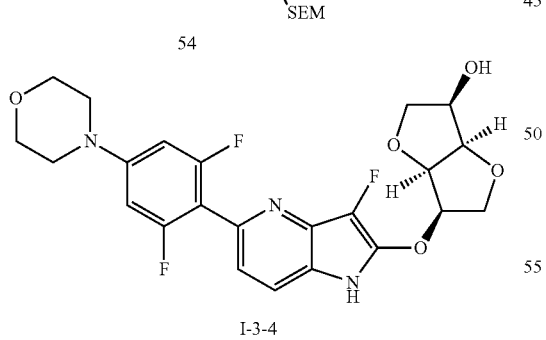

I-3-4

Compound 30 (250.0 mg, 0.319 mmol) was dissolved in THF (2.1 mL), and the mixture was cooled to −78° C., and a solution of n-BuLi in hexane (1.65 M, 0.387 mL, 0.639 mmol) was added thereto, and the reaction mixture was stirred for 15 minutes. Thereafter, HMPA (0.111 mL, 0.639 mmol) and N-Fluorobenzenesulfonimide (0.503 g, 1.60 mmol) were added thereto, the resulting mixture was stirred at −78° C. for 30 minutes. After being stirred at −30° C. for 30 minutes, to the reaction mixture was added a saturated aqueous solution of ammonium chloride, and the resulting mixture was extracted with ethyl acetate. The organic layer was washed with water, dried over sodium sulfate and concentrated under reduced pressure. The obtained residue was purified by silica gel column chromatography to obtain Compound 54 (16.6 mg, 7.2%).

Compound 54;

Method A

LC/MS retention time=3.52 min.

MS (ESI) m/z=722.30 (M+H)$^+$.

Compound 54 (16.0 mg, 0.022 mmol) was dissolved in CH$_2$Cl$_2$ (0.16 mL), trifluoroacetic acid (0.16 ml) was added thereto, and the reaction mixture was stirred at room temperature for 3 hours. Thereafter, the solvent was removed under reduced pressure, and the obtained residue was diluted with chloroform. The mixture was added to a saturated aqueous solution of sodium hydrogen carbonate, and the resulting mixture was stirred. Thereafter, methanol was added thereto, and the resulting mixture was stirred at room temperature and extracted with chloroform. The obtained organic layer was dried over sodium sulfate and concentrated under reduced pressure. The obtained residue was purified by reverse-phase chromatography to obtain Compound (I-3-4) (2.7 mg, 25.5%).

Compound (I-3-4); $^1$H-NMR (CDCl$_3$) δ: 3.19 (t, J=4.0 Hz, 4H), 3.75-3.79 (m, 1H), 3.86 (t, J=4.0 Hz, 4H), 4.02-4.15 (m, 2H), 4.23-4.27 (m, 1H), 4.36 (brs, 1H), 4.59 (t, J=4.0 Hz, 1H), 4.75 (t, J=4.0 Hz, 1H), 5.12 (d, J=8.0 Hz, 1H), 6.48 (d, J=12.0 Hz, 2H), 7.20 (d, J=8.0 Hz, 1H), 7.51 (d, J=8.0 Hz, 1H).

Method A

LC/MS retention time=1.19 min.

MS (ESI) m/z=478.2 (M+H)$^+$.

Example 16

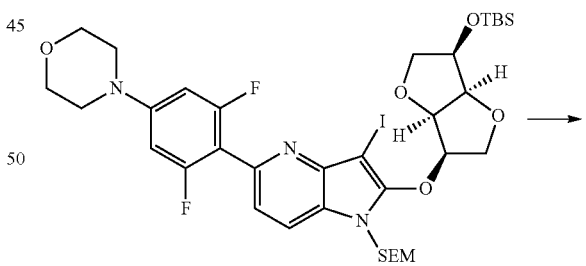

55

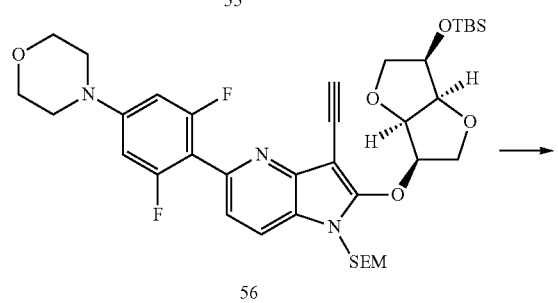

56

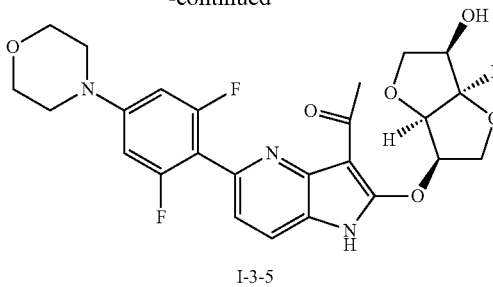

I-3-5

Compound 55 (108.0 mg, 0.130 mmol) was dissolved in Et₃N (0.13 mL), and trimethylacetylene (0.037 ml, 0.260 mmol), CuI (5.0 mg, 0.026 mmol), Pd(PPh₃)₄ (15.0 mg, 0.013 mmol) were added thereto, and the reaction mixture was stirred at 60° C. for 90 minutes. Thereafter, the solvent was removed under reduced pressure, and to the obtained residue were added methanol (0.26 mL) and K₂CO₃ (72.0 mg, 0.052 mmol), and the reaction mixture was stirred at room temperature for 5 hours. To the reaction mixture was added water, and the resulting mixture was extracted with ethyl acetate. The organic layer was washed with water, dried over sodium sulfate and concentrated under reduced pressure. The obtained residue was purified by silica gel column chromatography to obtain Compound 56 (62.8 mg, 66.3%).

Compound 56;
Method A
  LC/MS retention time=3.50 min.
  MS (ESI) m/z=728.30 (M+H)⁺.

Compound 56 (31.0 mg, 0.043 mmol) was dissolved in CH₂Cl₂ (0.31 mL), and trifluoroacetic acid (0.31 ml) was added thereto, and the reaction mixture was stirred at room temperature for 2 hours. Thereafter, the solvent was removed under reduced pressure, and the obtained residue was diluted with chloroform. The mixture was added to a saturated aqueous solution of sodium hydrogen carbonate, and the resulting mixture was stirred. Thereafter, methanol was added thereto, the resulting mixture was stirred at room temperature and extracted with chloroform. The obtained organic layer was dried over sodium sulfate and concentrated under reduced pressure. The obtained residue was purified by silica gel column chromatography to obtain Compound (I-3-5) (13.9 mg, 65.0%).

Compound (I-3-5);
  LC/MS retention time=1.20 min.
  MS (ESI) m/z=502.2 (M+H)⁺.

Example 17

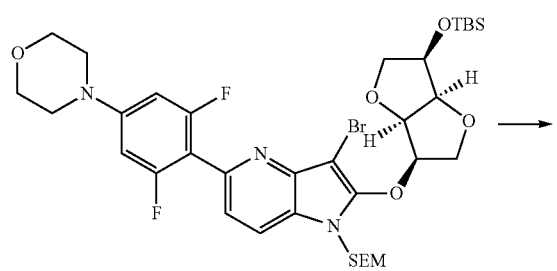

30

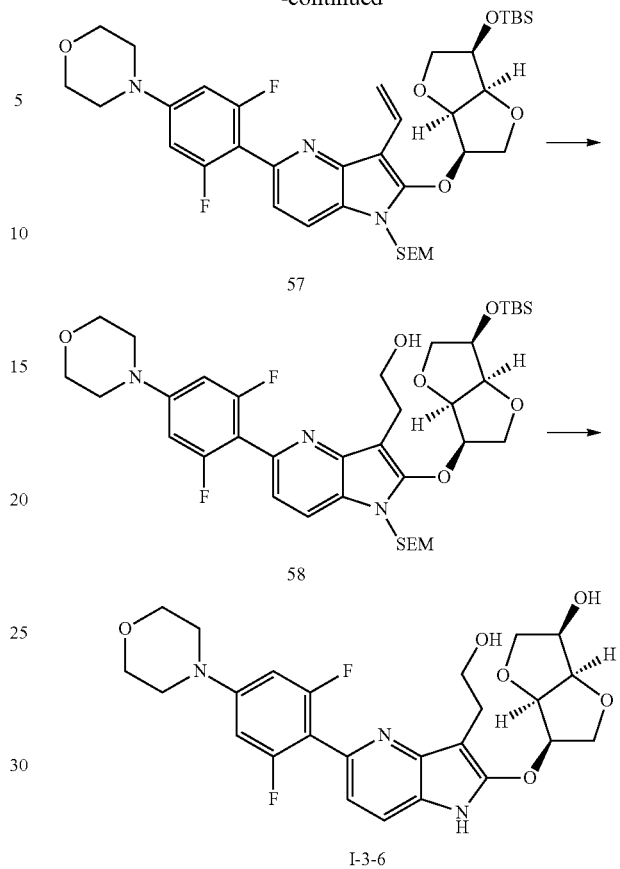

Compound 30 (137.0 mg, 0.175 mmol) was dissolved in DMF (1.1 mL), and tributyltine (0.153 ml, 0.525 mmol) and Pd(PPh₃)₄ (48.5 mg, 0.042 mmol) were added thereto, and the reaction mixture was stirred at 100° C. for 5 hours. To the reaction mixture was added water, and the resulting mixture was extracted with ethyl acetate. The organic layer was washed with water, dried over sodium sulfate and concentrated under reduced pressure. The obtained residue was purified by silica gel column chromatography to obtain Compound 57 (90.0 mg, 70.5%).

Compound 57
Method A
  LC/MS retention time=3.68 min.
  MS (ESI) m/z=730.3 (M+H)⁺

Compound 57 (78.5 mg, 0.108 mmol) was dissolved in THF (1.2 mL), and BH₃·SMe₂ (0.073 ml, 0.763 mmol) was added thereto, and the reaction mixture was stirred at room temperature for 3.5 hours. Thereafter, 1N NaOH (0.6 mL) and 30% hydrogen peroxide solution (0.6 mL) were added thereto, and the reaction mixture was stirred at room temperature for 2 hours. To the reaction mixture was added a saturated aqueous solution of ammonium chloride, and the resulting mixture was extracted with ethyl acetate. The organic layer was washed with water, dried over sodium sulfate and concentrated under reduced pressure. The obtained residue was purified by silica gel column chromatography to obtain Compound 58 (14.4 mg, 17.9%).

Compound 58;
Method A
  LC/MS retention time=3.36 min.
  MS (ESI) m/z=748.4 (M+H)⁺

Compound 58 (12.0 mg, 0.016 mmol) was dissolved in CH₂Cl₂ (0.12 mL), and trifluoroacetic acid (0.12 ml) was added thereto, and the reaction mixture was stirred at room temperature for 4 hours. Thereafter, the solvent was removed under reduced pressure, and the obtained residue was diluted with chloroform. The mixture was added to a saturated aqueous solution of sodium hydrogen carbonate, and the resulting mixture was stirred. Thereafter, methanol was added thereto, and the resulting mixture was stirred at room temperature and extracted with chloroform. The obtained organic layer was dried over sodium sulfate and concentrated under reduced pressure. The obtained residue was purified by silica gel column chromatography to obtain Compound (I-3-6) (4.2 mg, 52.0%).
Compound (I-3-6);
LC/MS retention time=1.15 min.
MS (ESI) m/z=504.2 (M+H)⁺.

Example 18

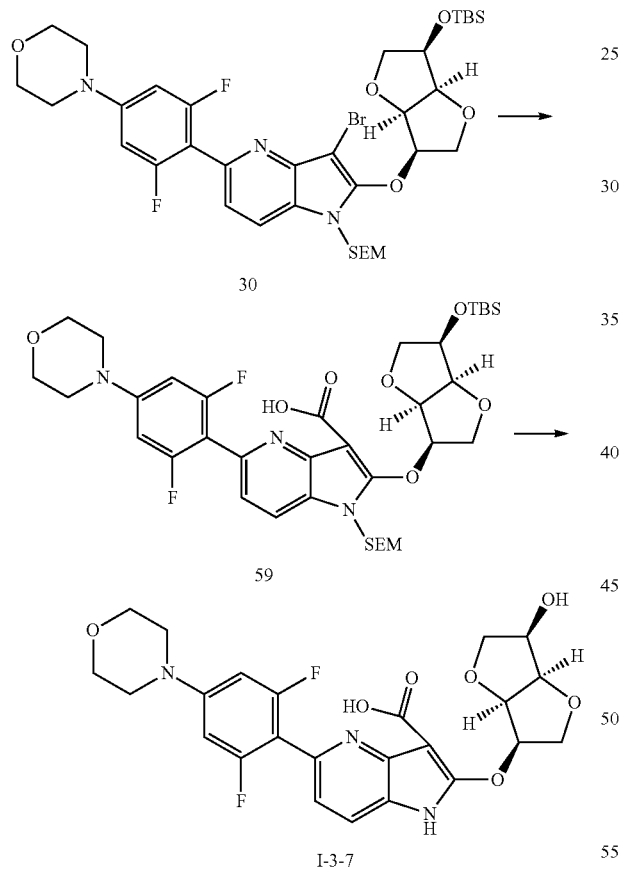

Compound 30 (50.0 mg, 0.0634 mmol) was dissolved in THF (0.43 mL), and the mixture was cooled to −78° C., and a solution of n-BuLi in hexane (1.65 M, 0.077 mL, 0.128 mmol) was added thereto, and the reaction mixture was stirred for 15 minutes. Thereafter, HMPA (0.022 mL, 0.128 mmol) and dry ice were added thereto, and the reaction mixture was warmed up to room temperature and stirred for an hour. To the reaction mixture was added a saturated aqueous solution of ammonium chloride, and the resulting mixture was extracted with ethyl acetate. The organic layer was washed with water, dried over sodium sulfate and concentrated under reduced pressure. The obtained residue was purified by silica gel column chromatography to obtain Compound 59 (30.0 mg, 62.8%).
Compound 59;
Method A
LC/MS retention time=3.58 min.
MS (ESI) m/z=748.3 (M+H)⁺.
Compound 59 (30.0 mg, 0.031 mmol) was dissolved in CH₂Cl₂ (0.24 mL), and trifluoroacetic acid (0.24 ml) was added thereto, and the reaction mixture was stirred at room temperature for 5 hours. Thereafter, the solvent was removed under reduced pressure, and the obtained residue was diluted with chloroform. The mixture was added to a saturated aqueous solution of sodium hydrogen carbonate, and the resulting mixture was stirred. Thereafter, methanol was added thereto, and the resulting mixture was stirred at room temperature and extracted with chloroform. The obtained organic layer was dried over sodium sulfate and concentrated under reduced pressure. The obtained residue was purified by silica gel column chromatography to obtain Compound (I-3-7) (2.1 mg, 10.4%).
Compound (I-3-7);
Method A
LC/MS retention time=1.10 min.
MS (ESI) m/z=504.2 (M+H)⁺.

Example 19

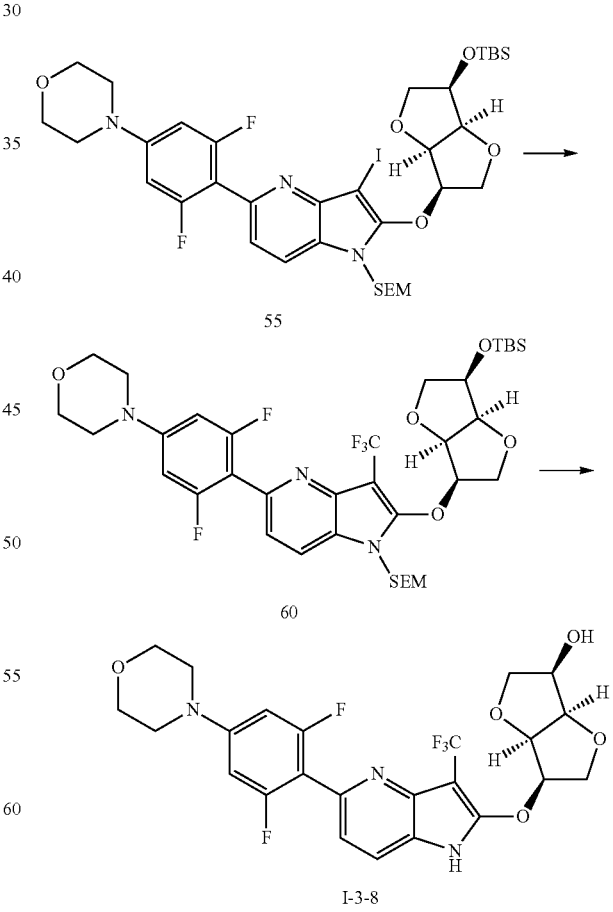

Compound 55 (200.0 mg, 0.245 mmol) was dissolved in DMF (1.0 mL), and Cu (46.7 mg, 0.736 mmol) and diphenyl (trifluoromethyl)sulfonium (132.0 mg, 0.490 mmol) were added thereto, and the reaction mixture was stirred at 60° C. for 90 minutes. Thereafter, Cu (140.1 mg, 2.21 mmol) and diphenyl(trifluoromethyl)sulfonium (396.0 mg, 1.47 mmol) were added in three additions every 90 minutes, and the reaction mixture was stirred at 60° C. for 90 minutes. To the reaction mixture was added a saturated aqueous solution of ammonium chloride, and the resulting mixture was extracted with ethyl acetate. The organic layer was washed with water, dried over sodium sulfate and concentrated under reduced pressure. The obtained residue was purified by silica gel column chromatography to obtain Compound 60 (75.0 mg, 40.4%).
Compound 60;
Method A
  LC/MS retention time=3.24 min.
  MS (ESI) m/z=758.3 (M+H)⁺.
Compound 60 (73.0 mg, 0.096 mmol) was dissolved in CH$_2$Cl$_2$ (0.57 mL), and trifluoroacetic acid (0.57 ml) was added thereto, and the reaction mixture was stirred at room temperature for an hour. Thereafter, the solvent was removed under reduced pressure, and the obtained residue was diluted with chloroform. The mixture was added to a saturated aqueous solution of sodium hydrogen carbonate, and the resulting mixture was stirred. Thereafter, methanol was added thereto, and the resulting mixture was stirred at room temperature and extracted with chloroform. The obtained organic layer was dried over magnesium sulfate and concentrated under reduced pressure to obtain Compound (I-3-8) (9.8 mg, 19.3%).
Compound (I-3-8);
Method A
  LC/MS retention time=1.42 min.
  MS (ESI) m/z=528.1 (M+H)⁺.
Compounds shown below were synthesized in the same manner. The measurement results of NMR or LC/MS of each compound were shown.

TABLE 1

| No. | Structure | NMR(δ) | retention time | Mass | method |
|---|---|---|---|---|---|
| I-1-2 | 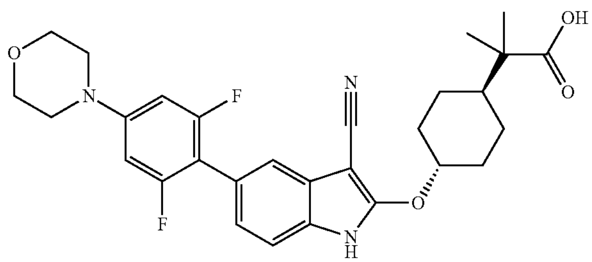 [SMILES: CC(C)(C(=O)O)[C@H]1CC[C@H](Oc2[nH]c3ccc(-c4c(F)cc(N5CCOCC5)cc4F)cc3c2C#N)CC1] | 1H-NMR (DMSO-D6) δ: 1.06 (6H, s), 1.14-1.29 (2H, m), 1.44-1.66 (3H, m), 1.73 (2H, d, J = 12.3 Hz), 2.25 (2H, d, J = 9.0 Hz), 3.21 (4H, t, J = 4.8 Hz). 3.73 (4H, t, J = 4.9 Hz), 4.62-4.72 (1H, m), 6.75 (2H, d, J = 11.5 Hz), 7.11 (1H, d, J = 8.3 Hz), 7.30-7.35 (2H, m), 12.19 (1H, brs). | 2.25 | 524.25 (M + H) | B |
| I-1-3 | 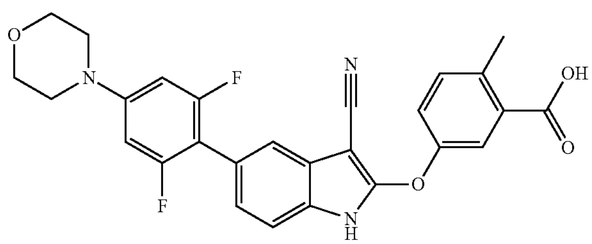 [SMILES: Cc1ccc(Oc2[nH]c3ccc(-c4c(F)cc(N5CCOCC5)cc4F)cc3c2C#N)cc1C(=O)O] | 1H-NMR (DMSO-D6) δ: 2.55 (3H, s), 3.22 (4H, t, J = 4.9 Hz), 3.73 (4H, t, J = 4.8 Hz), 6.77 (2H, d, J = 11.5 Hz), 7.20-7.25 (1H, m), 7.40-7.48 (4H, m), 7.68 (1H, d, J = 2.3 Hz). | 2.09 | 490.05 (M + H) | B |
| I-1-4 | 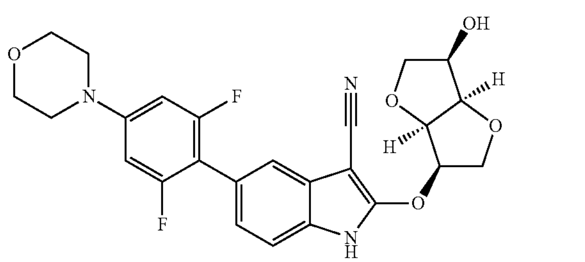 [SMILES: N#Cc1c(O[C@@H]2CO[C@H]3[C@@H]2OC[C@H]3O)[nH]c2ccc(-c3c(F)cc(N4CCOCC4)cc3F)cc12] | 1H-NMR (MeOD) δ: 3.21 (4H, t, J = 4.8 Hz), 3.62 (1H, t, J = 8.8 Hz), 3.83 (4H, t, J = 4.9 Hz), 3.91 (1H, dd, J = 8.3, 7.0 Hz), 4.09 (1H, dd, J = 10.5, 5.0 Hz), 4.18-4.30 (2H, m), 4.45 (1H, t, J = 5.1 Hz), 4.99 (1H, t, J = 5.4 Hz), 5.39 (1H, td, J = 5.3, 3.5 Hz), 6.63 (2H, dt, J = 19.9, 4.1 Hz), 7.17 (1H, dd, J = 8.4, 1.4 Hz), 7.30 (1H, d, J = 8.5 Hz), 7.38 (1H, s). | 1.76 | 484.00 (M + H) | B |
| I-1-5 | 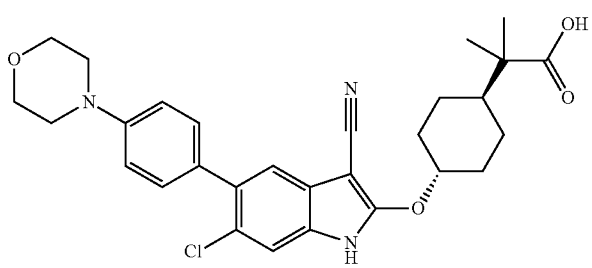 [SMILES: CC(C)(C(=O)O)[C@H]1CC[C@H](Oc2[nH]c3cc(Cl)c(-c4ccc(N5CCOCC5)cc4)cc3c2C#N)CC1] | 1H-NMR (DMSO-D6) δ: 1.06 (6H, s), 1.14-1.28 (2H, m), 1.42-1.66 (3H, m), 1.73 (2H, d, J = 12.3 Hz), 2.25 (2H, d, J = 9.3 Hz), 3.17 (4H, t, J = 4.8 Hz), 3.76 (4H, t, J = 4.8 Hz), 4.61-4.73 (1H, m), 7.01 (2H, d, J = 8.8 Hz), 7.25 (1H, s), 7.31 (2H, d, J = 8.8 Hz), 7.38 (1H, s), 12.16 (1H, br s), 12.27 (1H, s). | 2.31 | 522.05 (M + H) | B |

TABLE 1-continued

| No. | Structure | NMR(δ) | retention time | Mass | method |
|-----|-----------|--------|----------------|------|--------|
| I-1-6 | 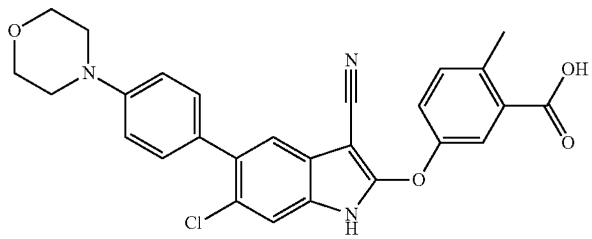 [SMILES: Cc1ccc(Oc2[nH]c3cc(Cl)c(-c4ccc(N5CCOCC5)cc4)cc3c2C#N)cc1C(=O)O] | 1H-NMR (DMSO-D6) δ: 2.55 (3H, s), 3.17 (4H, t, J = 4.8 Hz), 3.76 (4H, t, J = 4.8 Hz), 7.01 (2H, d, J = 8.8 Hz), 7.34 (3H, t, J = 8.7 Hz), 7.43-7.50 (3H, m), 7.68 (1H, d, J = 2.5 Hz), 12.72 (1H, s), 13.16 (1H, br s). | 2.13 | 487.90 (M + H) | B |

TABLE 2

| No. | Structure | NMR(δ) | retention time | Mass | method |
|-----|-----------|--------|----------------|------|--------|
| I-1-7 | 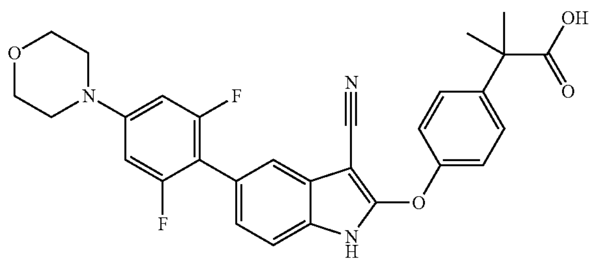 [SMILES: CC(C)(C(=O)O)c1ccc(Oc2[nH]c3ccc(-c4c(F)cc(N5CCOCC5)cc4F)cc3c2C#N)cc1] | 1H-NMR (DMSO-D6) δ: 1.50 (6H, s), 3.22 (4H, t, J = 4.8 Hz), 3.73 (4H, t, J = 4.8 Hz), 6.77 (2H, d, J = 11.5 Hz), 7.20-7.28 (3H, m), 7.42-7.48 (4H, m), 12.43 (1H, br s), 12.65 (1H, br s). | 2.18 | 518.00 (M + H) | B |
| I-1-8 | 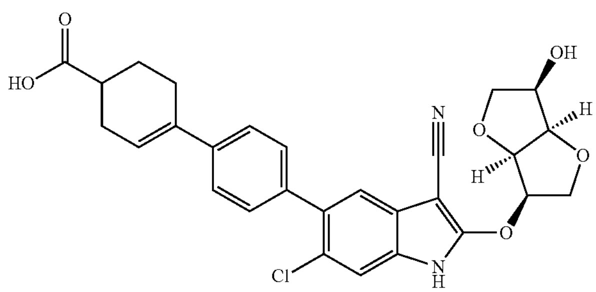 [SMILES: N#Cc1c(O[C@@H]2CO[C@H]3[C@@H]2OC[C@H]3O)[nH]c2cc(Cl)c(-c3ccc(C4=CCC(C(=O)O)CC4)cc3)cc12] | 1H-NMR (MeOD) δ: 1.80-1.91 (1H, m), 2.17-2.25 (1H, m), 2.39-2.68 (5H, m), 3.60 (1H, t, J = 8.7 Hz), 3.90 (1H, t, J = 7.5 Hz), 4.08 (1H, dd, J = 10.7, 4.9 Hz), 4.18-4.30 (2H, m), 4.44 (1H, t, J = 5.1 Hz), 4.99 (1H, t, J = 5.3 Hz), 5.39 (1H, td, J = 5.1, 3.3 Hz), 6.20 (1H, s), 7.31 (1H, s), 7.36-7.38 (3H, m), 7.46 (2H, d, J = 8.3 Hz). | 1.78 | 518.90 (M − H) | B |
| I-1-9 | 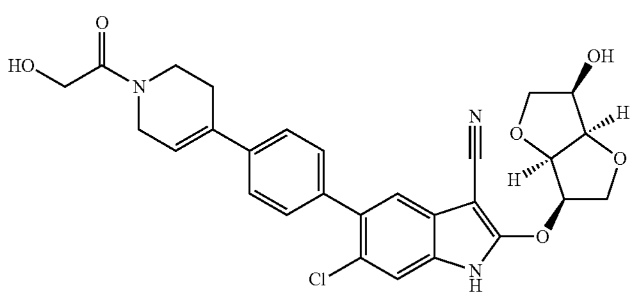 [SMILES: N#Cc1c(O[C@@H]2CO[C@H]3[C@@H]2OC[C@H]3O)[nH]c2cc(Cl)c(-c3ccc(C4=CCN(C(=O)CO)CC4)cc3)cc12] | 1H-NMR (MeOD) δ: 2.60-2.71 (2H, m), 3.57-3.69 (2H, m), 3.84-3.93 (2H, m), 4.05-4.15 (2H, m), 4.19-4.35 (5H, m), 4.44 (1H, t, J = 5.1 Hz), 4.99 (1H, t, J = 5.4 Hz), 5.39 (1H, td, J = 5.2, 3.2 Hz), 6.16-6.25 (1H, m), 7.32 (1H, s), 7.38-7.43 (3H, m), 7.50 (2H, d, J = 8.3 Hz). | 1.55 | 535.90 (M + H) | B |
| I-1-10 | 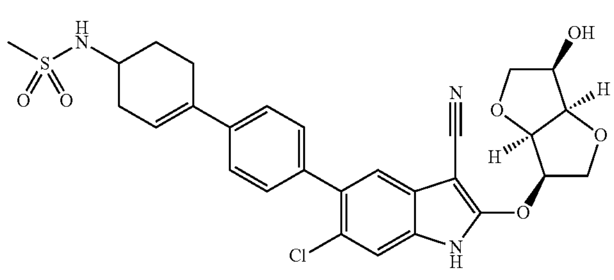 [SMILES: CS(=O)(=O)NC1CC=C(c2ccc(-c3cc4c(C#N)c(O[C@@H]5CO[C@H]6[C@@H]5OC[C@H]6O)[nH]c4cc3Cl)cc2)CC1] | 1H-NMR (MeOD) δ: 1.75-1.87 (1H, m), 2.10-2.30 (2H, m), 2.59-2.69 (2H, m), 3.00 (3H, s), 3.57-3.66 (2H, m), 3.90 (1H, t, J = 7.5 Hz), 4.08 (1H, dd, J = 10.5, 5.0 Hz), 4.19-4.29 (2H, m), 4.44 (1H, t, J = 5.1 Hz), 4.99 (1H, t J = 5.4 Hz), 5.39 (1H, td, J = 5.3, 3.2 Hz), 6.12 (1H, s), 7.31 (1H, s), 7.35-7.40 (3H, m), 7.47 (2H, d, J = 8.3 Hz). | 1.77 | 568.40 (M − H) | B |

TABLE 3

| No. | Structure | NMR(δ) | retention time | Mass | method |
|---|---|---|---|---|---|
| I-2-9 | 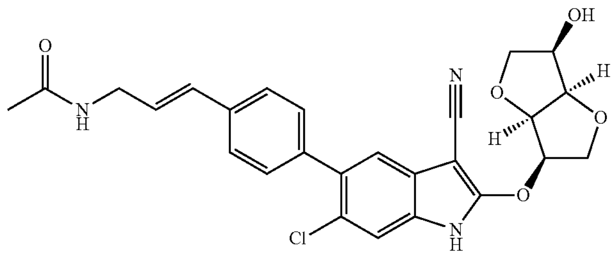 [SMILES: CC(=O)NC/C=C/c1ccc(-c2cc3c(C#N)c(O[C@@H]4CO[C@H]5[C@@H]4OC[C@H]5O)[nH]c3cc2Cl)cc1] | 1H-NMR (MeOD) δ: 2.00 (3H, s), 3.60 (1H, t J = 8.8 Hz), 3.90 (1H, t, J = 7.5 Hz), 3.98 (2H, d, J = 5.5 Hz), 4.08 (1H, dd, J = 10.8, 5.0 Hz), 4.18-4.29 (2H, m), 4.44 (1H, t, J = 5.1 Hz), 4.99 (1H, t, J = 5.5 Hz), 5.36-5.42 (1H, m), 6.25-6.34 (1H, m), 6.61 (1H, d, J = 15.8 Hz), 7.30-7.48 (6H, m). | | | |
| I-2-10 | 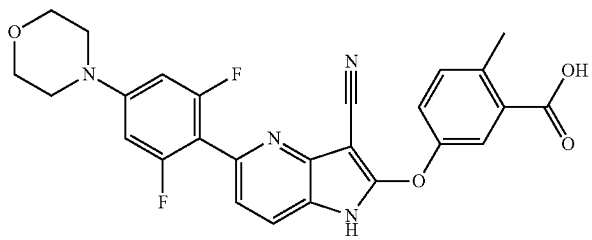 [SMILES: Cc1ccc(Oc2[nH]c3ccc(-c4c(F)cc(N5CCOCC5)cc4F)nc3c2C#N)cc1C(=O)O] | 1H-NMR (MeOD) δ: 2.64 (3H, s), 3.26-3.30 (0H, m), 3.80-3.85 (4H, m), 6.65-6.72 (2H, m), 7.38-7.48 (3H, m), 7.88-7.96 (2H, m). | | | |
| I-2-11 | 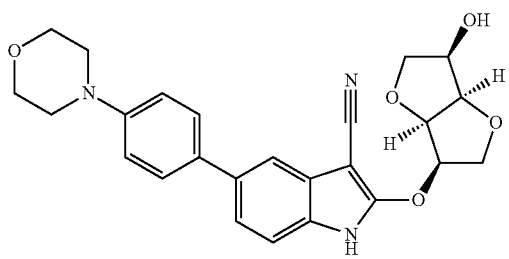 [SMILES: N#Cc1c(O[C@@H]2CO[C@H]3[C@@H]2OC[C@H]3O)[nH]c2ccc(-c3ccc(N4CCOCC4)cc3)cc12] | 1H-NMR (MeOD) δ: 3.16-3.20 (4H, m), 3.59-3.65 (1H, m), 3.83-3.88 (4H, m), 3.91 (1H, dd, J = 8.2, 6.9 Hz), 4.09 (1H, dd, J = 10.5, 5.0 Hz), 4.17-4.30 (2H, m), 4.45 (1H, t, J = 5.3 Hz), 4.99 (1H, t, J = 5.3 Hz), 5.36-5.41 (1H, m), 7.05 (2H, d, J = 8.8 Hz), 7.29 (1H, d, J = 8.3 Hz), 7.37 (1H, dd, J = 8.3, 1.8 Hz), 7.52-7.57 (3H, m). | | | |
| I-2-12 | 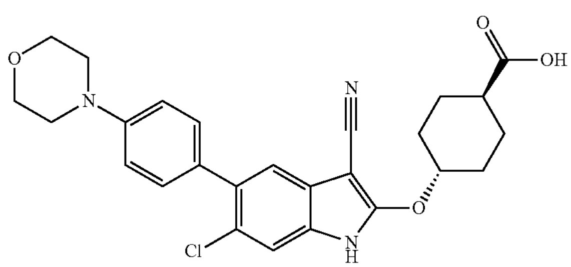 [SMILES: N#Cc1c(O[C@H]2CC[C@H](C(=O)O)CC2)[nH]c2cc(Cl)c(-c3ccc(N4CCOCC4)cc3)cc12] | | 2.06 | 480.05 (M + H) | B |
| I-2-13 | 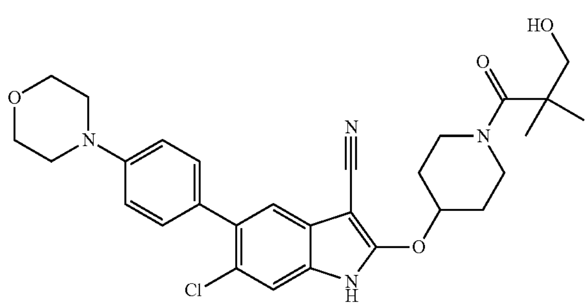 [SMILES: CC(C)(CO)C(=O)N1CCC(Oc2[nH]c3cc(Cl)c(-c4ccc(N5CCOCC5)cc4)cc3c2C#N)CC1] | | 2.04 | 537.15 (M + H) | B |

TABLE 4

| | | | |
|---|---|---|---|
| I-2-14 | [structure] | 1.81 | 397.95 B (M + H) |
| I-2-15 | [structure] | 2.04 | 424.2 B (M + H) |
| I-2-16 | [structure] | 2.13 | 503.1 B (M + H) |
| I-2-17 | [structure] | 1H-NMR (MeOD) δ: 3.22-3.27 (0H, m), 3.58-3.65 (1H, m), 3.85-3.93 (5H, m), 4.05-4.13 (1H, m), 4.21-4.31 (2H, m), 4.43-4.48 (1H, m), 4.99-5.04 (1H, m), 5.41-5.48 (1H, m), 7.09 (2H, d, J = 7.5 Hz), 7.43-7.51 (3H, m), 7.66-7.68 (1H, m). | |
| I-2-18 | [structure] | 1H-NMR (MeOD) δ: 1.67 (s, 6H), 1.97 (s, 3H), 3.24 (t, J = 4.0 Hz, 4H), 3.89 (t, J = 4.0 Hz, 4H), 7.05-7.52 (m, 10H). | |

TABLE 5

| No. | Structure | NMR |
|---|---|---|
| I-2-19 | 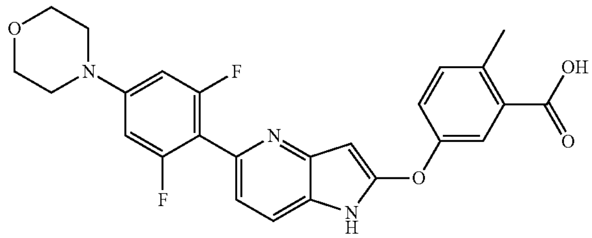 [SMILES: Cc1ccc(Oc2cc3nc(-c4c(F)cc(N5CCOCC5)cc4F)ccc3[nH]2)cc1C(=O)O] | 1H-NMR (MeOD) δ: 2.57 (3H, s), 3.26 (4H, t, J = 4.9 Hz), 3.84 (4H, t, J = 4.8 Hz), 5.75 (1H, s), 6.68 (2H, d, J = 11.5 Hz), 7.24 (1H, d, J = 8.3 Hz), 7.30 (1H, dd, J = 8.4, 2.6 Hz), 7.36 (1H, d, J = 8.3 Hz), 7.64 (1H, d, J = 2.8 Hz), 7.85 (1H, d, J = 8.0 Hz). |
| I-2-20 | 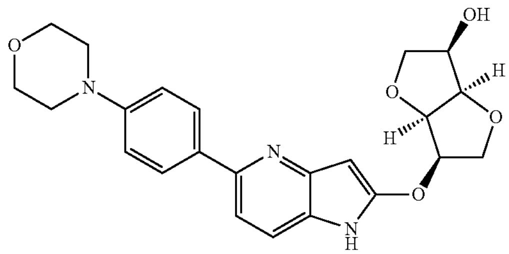 [SMILES: O[C@@H]1CO[C@H]2[C@@H]1OC[C@H]2Oc1cc2nc(-c3ccc(N4CCOCC4)cc3)ccc2[nH]1] | 1H-NMR (MeOD) δ: 3.22 (4H, t, J = 4.8 Hz), 3.64 (1H, t, J = 8.5 Hz), 3.87 (4H, t, J = 4.8 Hz), 3.95 (1H, dd, J = 8.3, 6.8 Hz), 4.02 (1H, dd, J = 9.5, 6.0 Hz), 4.22 (1H, dd, J = 9.4, 6.1 Hz), 4.28-4.35 (1H, m), 5.03-5.10 (1H, m), 5.87 (1H, s), 7.07 (2H, d, J = 8.8 Hz), 7.35 (1H, d, J = 8.3 Hz), 7.57 (1H, d, J = 8.3 Hz), 7.79 (2H, d, J = 8.8 Hz). |

TABLE 6

| No. | Structure | NMR(δ) | retention time | Mass | method |
|---|---|---|---|---|---|
| I-3-9 | 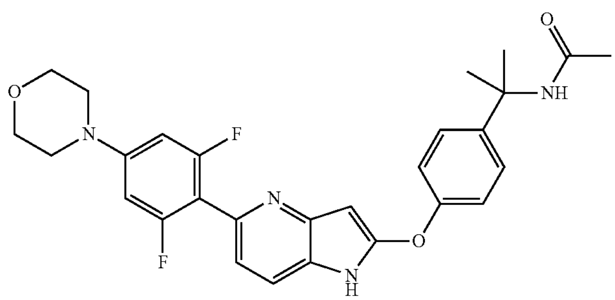 [SMILES: CC(=O)NC(C)(C)c1ccc(Oc2cc3nc(-c4c(F)cc(N5CCOCC5)cc4F)ccc3[nH]2)cc1] | (DMSO-d6) δ: 1.55 (s, 6H), 1.83 (s, 3H), 3.21 (t, J = 4.0 Hz, 4H), 3.73 (t, J = 4.0 Hz, 4H), 5.72 (s, 1H), 6.72 (d, J = 12.0 Hz, 2H), 7.08 (d, J = 8.0 Hz, 1H), 7.17 (d, J = 8.0 Hz, 2H), 7.37 (d, J = 8.0 Hz, 2H), 7.64 (d, J = 8.0 Hz, 1H), 8.09 (s, 1H), 8.47 (s, 1H). | 1.52 | 507.2 (M + H) | A |
| I-3-10 | 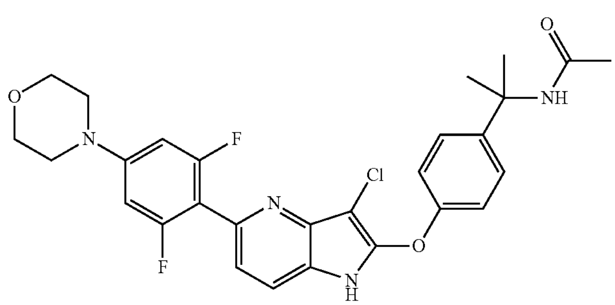 [SMILES: CC(=O)NC(C)(C)c1ccc(Oc2[nH]c3ccc(-c4c(F)cc(N5CCOCC5)cc4F)nc3c2Cl)cc1] | (DMSO-d6) δ: 1.53 (s, 6H), 1.81 (s, 3H), 3.23 (t, J = 4.0 Hz, 4H), 3.75 (t, J = 4.0 Hz, 4H), 6.75 (d, J = 8.0 Hz, 2H), 6.99 (d, J = 8.0 Hz, 2H), 7.16 (d, J = 8.0 Hz, 1H), 7.32 (d, J = 8.0 Hz, 2H), 7.71 (d, J = 8.0 Hz, 1H), 8.05 (s, 1H), 8.46 (s, 1H). | 1.8 | 541.2 (M + H) | A |
| I-3-11 | 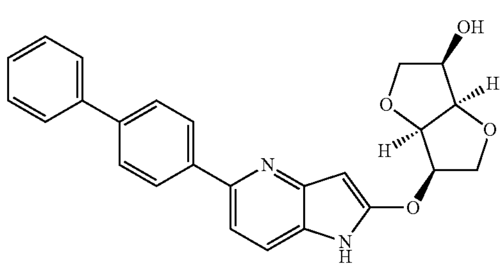 [SMILES: O[C@@H]1CO[C@H]2[C@@H]1OC[C@H]2Oc1cc2nc(-c3ccc(-c4ccccc4)cc3)ccc2[nH]1] | (DMSO-d6) δ: 3.45 (t, J = 8.0 Hz, 1H), 3.81 (m, 2H), 4.16 (m, 2H), 4.40 (t, J = 4.0 Hz, 1H), 4.84 (t, J = 4.0 Hz, 1H), 5.04 (dd, J = 12.0, 4.0 Hz, 1 H), 5.94 (s, 1H), 7.38 (m, 1H), 7.51 (m, 4H), 7.73 (m, 4H), 8.14 (m, 2H). | 1.46 | 415.2 (M + H) | A |

TABLE 6-continued

| No. | Structure | NMR(δ) | retention time | Mass | method |
|---|---|---|---|---|---|
| I-3-12 | 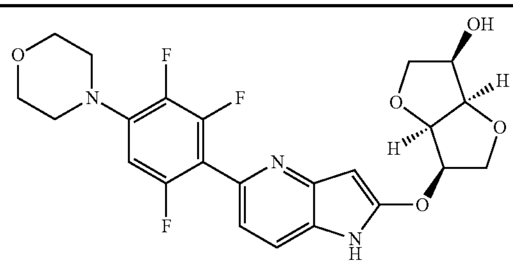 | (DMSO-d6) δ: 3.12 (t, J = 4.0 Hz, 4H), 3.79 (m, 6H), 4.15 (m, 2H), 4.38 (t, J = 4.0 Hz, 1H), 4.83 (t J = 4.0 Hz, 1H), 5.03 (dd, J = 12.0, 4.0 Hz, 1H), 5.92 (s, 1H), 6.83 (m, 1H), 7.04 (d, J = 8.0 Hz, 1H), 7.53 (d, J = 8.0 Hz, 1H). | 1.17 | 478.2 (M + H) | A |
| I-3-13 | 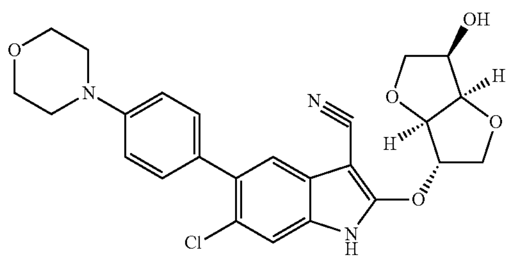 [SMILES: N#Cc1c(O[C@H]2CO[C@H]3[C@@H]2OC[C@H]3O)[nH]c2cc(Cl)c(-c3ccc(N4CCOCC4)cc3)cc12] | | 1.79 | 482.05 (M + H) | B |

TABLE 7

| No. | Structure | NMR(δ) | retention time | Mass | method |
|---|---|---|---|---|---|
| I-3-14 | 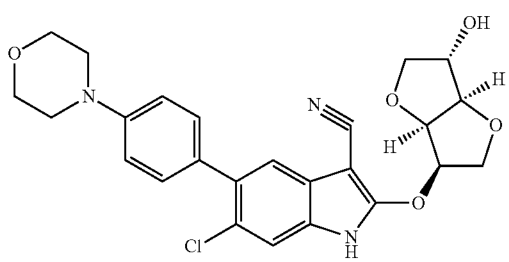 [SMILES: N#Cc1c(O[C@@H]2CO[C@H]3[C@@H]2OC[C@@H]3O)[nH]c2cc(Cl)c(-c3ccc(N4CCOCC4)cc3)cc12] | | 1.77 | 482.25 (M + H) | B |
| I-3-15 | 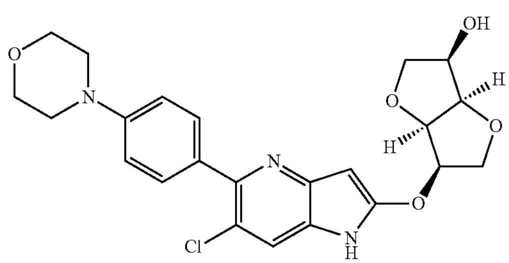 [SMILES: O[C@@H]1CO[C@H]2[C@@H]1OC[C@H]2Oc1cc2nc(-c3ccc(N4CCOCC4)cc3)c(Cl)cc2[nH]1] | | 1.03 | 458.05 (M + H) | B |
| I-3-16 | 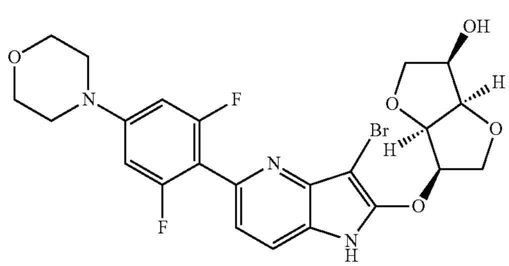 [SMILES: O[C@@H]1CO[C@H]2[C@@H]1OC[C@H]2Oc1[nH]c2ccc(-c3c(F)cc(N4CCOCC4)cc3F)nc2c1Br] | (DMSO-d6) δ: 3.25 (t, J = 4.0 Hz, 4H), 3.76-3.83 (m, 5H), 3.99-4.07 (m, 1H), 4.15 (brs, 1H), 4.37 (t, J = 4.0 Hz, 1H), 4.83 (t, J = 4.0 Hz, 1H), 5.09 (brs, 1H), 5.25 (d, J = 4.0 Hz, 1H), 6.75 (d, J = 12.0 Hz, 2H), 7.12 (d, J = 8.0 Hz, 1H), 7.69 (d, J = 8.0 Hz, 1H). | 1.24 | 538 (M + H) | A |

TABLE 7-continued

| | | | | |
|---|---|---|---|---|
| I-3-17 | | 1.8 | 454 (M + H) | B |
| I-3-18 | | 1.54 | 449 (M + H) | B |

TABLE 8

| | | | | |
|---|---|---|---|---|
| I-3-19 | | 1.35 | 488.2 (M + H) | A |
| I-3-20 | | 1.33 | 500.2 (M + H) | A |
| I-3-21 | | 1.2 | 497.15 (M + H) | B |

TABLE 8-continued

| I-3-22 | [structure] | 1.46 | 498.15 (M + H) | B |
| I-3-23 | [structure] | 0.98 | 512.3 (M + H) | B |

TABLE 9

| I-3-24 | [structure] | 1.17 | 478.05 (M + H) | B |
| I-3-25 | [structure] | 1.07 | 496.1 (M + H) | B |
| I-3-26 | [structure] | 1.07 | 418.05 (M + H) | B |

TABLE 9-continued

| ID | Structure | | | |
|---|---|---|---|---|
| I-3-27 | (structure) | 1.2 | 472 (M + H) | B |
| I-3-28 | (structure) | 1.29 | 513.15 (M + H) | B |

TABLE 10

| ID | Structure | NMR | | | |
|---|---|---|---|---|---|
| I-3-29 | (structure) | | 1.2 | 499.1 (M + H) | B |
| I-3-30 | (structure) | | 1.07 | 465.1 (M + H) | B |
| I-3-31 | (structure) | (DMSO-d6) δ: 1.09 (s, 6H), 2.56 (s, 2H), 3.15 (d, J = 4.0 Hz, 1H), 3.37-3.45 (m, 1H), 4.13 (t, J = 8.0 Hz, 1H), 4.33-4.44 (m, 1H), 4.66 (s, 1H), 4.83 (brs, 1H), 5.00 (d, J = 8.0 Hz, 1H), 5.17 (d, J = 8.0 Hz, 1H), 5.92 (s, 1H), 7.51-7.57 (m, 3H), 7.81 (d, J = 8.0 Hz, 2H), 8.09 (d, J = 8.0 Hz, 2H), 8.21 (s, 1H). | 1.1 | 477.2 (M + H) | A |

TABLE 10-continued

| | | | | |
|---|---|---|---|---|
| I-3-32 | [structure] | | 1.19 457.2 (M + H) | A |
| I-3-33 | [structure] | | 0.96 514.2 (M + H) | A |

TABLE 11

| | | | | |
|---|---|---|---|---|
| I-3-34 | [structure] | (DMSO-d6) δ: 1.92 (brs, 1H), 2.03-2.06 (m, 1H), 3.10 (d, J = 12.0 Hz, 1H), 3.33-3.46 (m, 2H), 3.79-3.81 (m, 2H), 4.15-4.19 (m, 2H), 4.39-4.40 (m, 2H), 4.82-4.84 (m, 1H), 4.96-5.03 (m, 3H), 5.89 (s, 1H), 6.23 (d, J = 12.0 Hz, 2H), 6.93 (d, J = 8.0 Hz, 1H), 7.46 (d, J = 8.0 Hz, 1H). | 1.05 460.2 (M + H) | A |
| I-3-35 | [structure] | (DMSO-d6) δ: 3.43-3.51 (m, 1H), 3.80-3.82 (m, 2H), 4.17-4.21 (m, 2H), 4.40 (brs, 1H), 4.85 (brs, 1H), 4.97-4.99 (m, 1H), 5.02-5.05 (m, 1H), 5.97 (s, 1H), 6.58 (s, 1H), 7.52 (d, J = 8.0 Hz, 1H), 7.58 (d, J = 8.0 Hz, 1H), 7.78-7.97 (m, 7H), 8.16 (d, J = 8.0 Hz, 2H), 8.58 (s, 1H), 11.41 (brs, 1H). | 1.54 481.2 (M + H) | A |
| I-3-36 | [structure] | (DMSO-d6) δ: 1.12 (s, 6H), 2.58 (s, 2H), 3.43-3.51 (m, 1H), 3.82 (brs, 2H), 4.17-4.21 (m, 2H), 4.38-4.41 (m, 1H), 4.85 (brs, 1H), 4.98-5.05 (m, 2H), 5.98 (s, 1H), 7.51-7.60 (m, 3H), 7.79-7.92 (m, 6H), 8.16 (d, J = 8.0 Hz, 2H), 8.31 (s, 1H), 11.41 (brs, 1H). | 1.45 553.2 (M + H) | A |

TABLE 11-continued

| | | | | | |
|---|---|---|---|---|---|
| I-3-37 | (structure) | | 1.18 | 442.15 (M + H) | B |
| I-3-38 | (structure) | | 1.39 | 553.3 (M + H) | B |

TABLE 12

| | | | | | |
|---|---|---|---|---|---|
| I-3-39 | (structure) | | 1.48 | 553 (M + H) | A |
| I-3-40 | (structure) | | 1.19 | 400.05 (M + H) | B |
| I-3-41 | (structure) | (DMSO-d6) δ: 3.33-3.47 (m, 1H), 3.64-3.66 (m, 4H), 3.80-3.84 (m, 2H), 4.17-4.20 (m, 2H), 4.39-4.41 (m, 1H), 4.83-4.86 (m, 1H), 4.98 (brs, 1H), 5.04 (dd, J = 12.0, 4.0 Hz, 1H), 5.95 (s, 1H), 7.50-7.57 (m, 2H), 7.66 (s, 1H), 7.86 (d, J = 8.0 Hz, 2H), 8.16 (d, J = 8.0 Hz, 2H), 8.43 (s, 1H). | 1.18 | 477.2 (M + H) | A |

TABLE 12-continued

| | | | | |
|---|---|---|---|---|
| I-3-42 | (structure) | | 1.17 | 534.1 (M + H) B |
| I-3-43 | (structure) | | 1.26 | 525.15 (M + H) B |

TABLE 13

| | | | | |
|---|---|---|---|---|
| I-3-44 | (structure) | (DMSO-d6) δ: 2.63 (s, 2H), 3.80-3.82 (m, 2H), 4.16-4.18 (m, 2H), 4.40 (brs, 1H), 4.85 (brs, 1H), 5.03-5.04 (m, 1H), 5.96 (s, 1H), 7.50-7.56 (m, 2H), 7.62 (s, 1H), 7.85 (d, J = 8.0 Hz, 2H), 8.14 (d, J = 8.0 Hz, 2H), 8.33 (s, 1H). | 0.95 | 463.2 (M + H) A |
| I-3-45 | (structure) | (DMSO-d6) δ: 3.41-3.45 (m, 2H), 3.77 (t, J = 8.0 Hz, 1H), 3.84 (t, J = 4.0 Hz, 2H), 3.99-4.03 (m, 1H), 4.09 (brs, 2H), 4.26 (brs, 2H), 4.32-4.34 (m, 1H), 4.91 (brs, 1H), 5.07 (d, J = 8.0 Hz, 1H), 5.40 (brs, 1H), 6.53 (s, 1H), 7.26 (d, J = 8.0 Hz, 1H), 7.32 (d, J = 8.0 Hz, 2H), 7.75 (d, J = 8.0 Hz, 1H). | 1.59 | 482.1 (M + H) A |
| I-3-46 | (structure) | | 1.13 | 510.2 (M + H) B |

TABLE 13-continued

| ID | Structure | NMR | RT | MS | Class |
|---|---|---|---|---|---|
| I-3-47 | 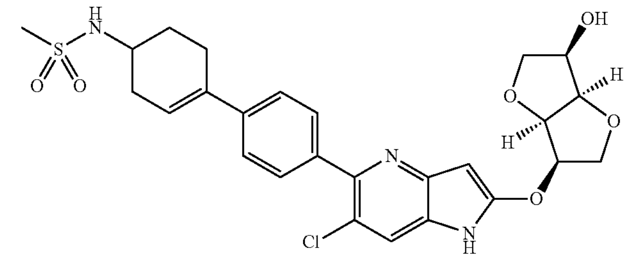 [SMILES: CS(=O)(=O)NC1CC=C(c2ccc(-c3nc4cc(O[C@@H]5CO[C@H]6[C@@H]5OC[C@H]6O)[nH]c4cc3Cl)cc2)CC1] | | 1.19 | 546.15 (M + H) | B |
| I-3-48 | 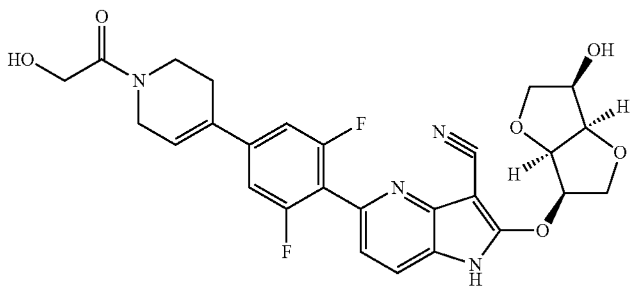 [SMILES: N#Cc1c(O[C@@H]2CO[C@H]3[C@@H]2OC[C@H]3O)[nH]c2ccc(-c3c(F)cc(C4=CCN(C(=O)CO)CC4)cc3F)nc12] | (DMSO-d6) δ: 2.58 (brs, 1H), 3.40-3.43 (m, 1H), 3.58 (brs, 1H), 3.72 (brs, 1H), 3.77 (t, J = 8.0 Hz, 1H), 4.02 (brs, 1H), 4.11-4.18 (m, 5H), 4.33 (brs, 1H), 4.60-4.67 (m, 1H), 4.91 (brs, 1H), 5.07 (d, J = 4.0 Hz, 1H), 5.40 (brs, 1H), 6.43-6.46 (m, 1H), 7.27-7.33 (m, 3H), 7.74-7.76 (m, 1H). | 1.22 | 539.2 (M + H) | A |

TABLE 14

| ID | Structure | NMR | RT | MS | Class |
|---|---|---|---|---|---|
| I-3-49 | 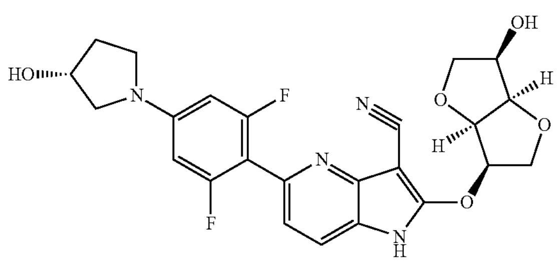 [SMILES: N#Cc1c(O[C@@H]2CO[C@H]3[C@@H]2OC[C@H]3O)[nH]c2ccc(-c3c(F)cc(N4CC[C@@H](O)C4)cc3F)nc12] | (DMSO-d6) δ: 1.91 (brs, 1H), 2.05-2.07 (m, 1H), 3.13 (d, J = 12.0 Hz, 1H), 3.43 (t, J = 8.0 Hz, 2H), 3.77 (t, J = 8.0 Hz, 1H), 4.02 (brs, 1H), 4.08-4.11(m, 2H), 4.33-4.34 (m, 1H), 4.42 (brs, 1H), 4.89 (brs, 1H), 5.05-5.07 (m, 2H), 5.39 (brs, 1H), 6.28 (d, J = 8.0 Hz, 2H), 7.13 (d, J = 8.0 Hz, 2H), 7.66 (d, J = 8.0 Hz, 1H). | 1.16 | 485 (M + H) | A |
| I-3-50 | 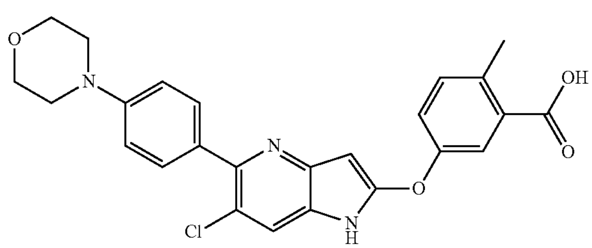 [SMILES: Cc1ccc(Oc2cc3nc(-c4ccc(N5CCOCC5)cc4)c(Cl)cc3[nH]2)cc1C(=O)O] | | 1.42 | 464.10 (M + H) | B |
| I-3-51 | 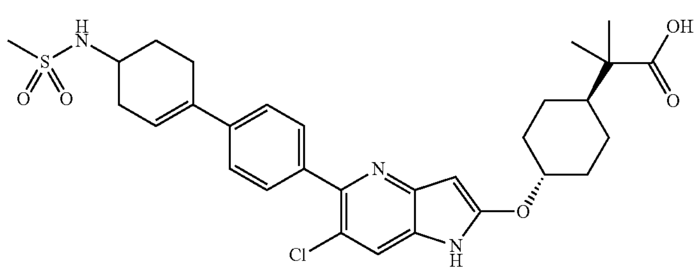 [SMILES: CC(C)(C(=O)O)[C@H]1CC[C@H](Oc2cc3nc(-c4ccc(C5=CCC(NS(C)(=O)=O)CC5)cc4)c(Cl)cc3[nH]2)CC1] | | 1.59 | 586.15 (M + H) | B |

TABLE 14-continued
| | | | | |
|---|---|---|---|---|
| I-3-52 | | 1.43 | 553.3 (M + H) | B |
| I-3-53 | | 1.07 | 430.15 (M + H) | B |
| I-3-54 | | 1.27 | 494.2 (M + H) | B |
As a compound of the present invention, a compound shown below can be also synthesized in accordance with the above Example.
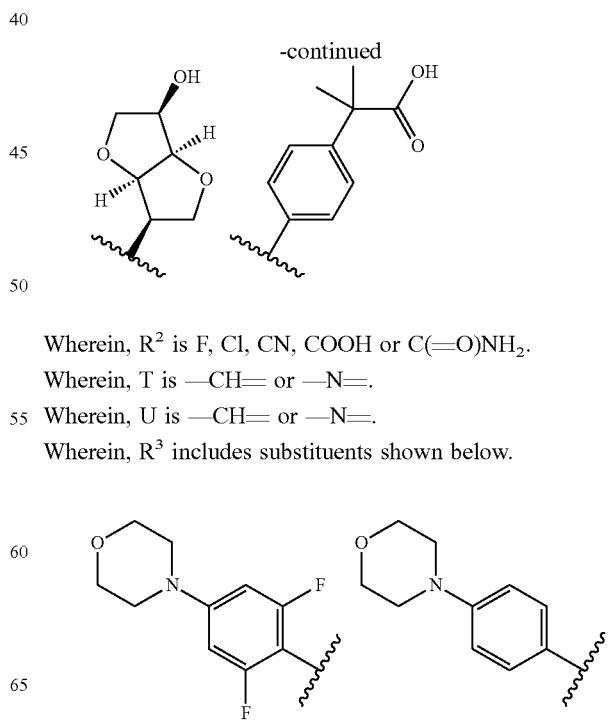
Wherein, Y includes substituents shown below.
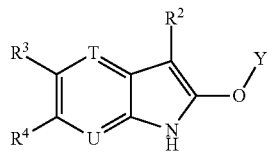
Wherein, $R^2$ is F, Cl, CN, COOH or C(=O)NH$_2$.
Wherein, T is —CH= or —N=.
Wherein, U is —CH= or —N=.
Wherein, $R^3$ includes substituents shown below.

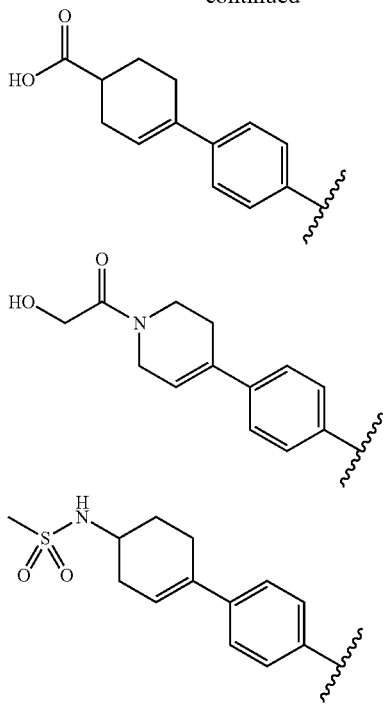

Wherein, $R^4$ is H, F or Cl.

Evaluation Method of an Activator for AMP-Activated Protein Kinase (AMPK)

Test Example 1

To a buffer solution consisting of a 50 mM HEPES-NaOH buffer solution (pH 7.0), 100 mM NaCl, 10 mM magnesium chloride, 0.1% bovine serum albumin, 0.2 mM sodium orthovanadate(V), 1 mM ethylene glycol-bis(2-aminoethyl ether)-N,N,N',N'-tetraacetic acid (EGTA), 5 mM disodium β-glycerophosphate and 2 mM dithiothreitol, a human AMPK α1β1γ1 enzyme (manufactured by Carna Biosciences, Inc.) was added in an amount to give a conversion rate of approximately 10% by reaction for 2 hours, and a compound dissolved in DMSO was added thereto so as to have a 1% DMSO concentration. The obtained liquid was left to stand for 10 minutes.

To the liquid, a substrate solution consisting of a 50 mM HEPES-NaOH buffer solution (pH 7.0), 100 mM NaCl, 10 mM magnesium chloride, 0.1% bovine serum albumin, 0.2 mM sodium orthovanadate(V), 1 mM ethylene glycol-bis(2-aminoethyl ether)-N,N,N',N'-tetraacetic acid (EGTA), 5 mM disodium β-glycerophosphate, 2 mM dithiothreitol, 0.4 mM ATP and 3 μM FL-Peptide 7 (manufactured by Caliper Life Sciences, Inc.) was added in equal amount (10 μl in total). The obtained liquid was allowed to react at 25° C. for 2 hours, and 10 μl of 20 mM EDTA was then added thereto to stop the reaction.

To detect phosphorylated fluorescent substrates, the reaction liquid was applied to a measuring device, LabChip EZ Reader II manufactured by Caliper Life Science, Inc., for detecting fluorescence by using differences in mobility due to differences in charge. The setting conditions for the device were pressure, −1.5 PSI; upstream voltage, −2250 V; downstream voltage, −400 V; post sample buffer sip time, 40 seconds; final delay, 120 seconds; and peak order, Product First.

A conversion rate was calculated from the peak heights of the resulting substrate and product. The conversion rate when not containing a compound was used as a control, and a concentration dependent curve was made by plotting the rate of increase in activity to the control at each concentration of a compound. The compound concentration showing 150% relative to the control (100%) was used as the EC 150 value, and the maximum rate of increase in activity within the measurement range was used as Emax.

Preparation Method of Human Ampk α2β2γ1

The full length cDNAs of human AMPK β2 (NM_005399.3) and human AMPK α2 (NM_006252.3) were inserted into the MCS1 and MCS2 of the pETDuet-1 vector to prepare a human AMPK β2 and human AMPK α2 (6× His tag at the 5' terminus) expressing plasmid. The plasmid was contransfected with an expression plasmid, in which the full length cDNA of human AMPK γ1 (NM_002733.3) had been inserted into pET28b(+), into BL21 CodonPlus (DE3)-RIL to obtain an expression strain. The expression strain was cultured in TB medium, followed by induction with 0.5 mM IPTG, and cultured at 25° C. for 3 hours and then harvested. After ultrasonication, supernatant was collected and applied to Histrap FF column (GE) and RESOUECE Q column (GE) to prepare 12.5 mg of purified sample containing three types of subunit from 1.8 L of broth.

Preparation Method of Human CaMKK2 Used to Impart Activity to AMPK

An expression vector, in which the full length cDNA of human CAMKK β (NM_172226.1) had been inserted into pGEX-6P-3, was transfected into BL21 Star (DE3). The expression strain was cultured in TB medium, followed by induction with 0.5 mM IPTG, and cultured at 25° C. for 3 hours and then harvested. After ultrasonication, supernatant was collected and applied to GSTrap FF column (GE) to prepare 14 mg of GST-fused CAMKK 13 from 720 ml of broth.

Evaluation Method of an Activator for AMP-Activated Protein Kinase (AMPK)

Test Example 2

Human AMPK α2β2γ1 prepared in *Escherichia coli* was not phosphorylated and did not exhibit activity. Thus, phosphorylation treatment was carried out as pretreatment.

Human AMPK α2β2γ1 in an amount to give a conversion rate of approximately 10% by reaction for 2 hours, and CaMKK2 in an amount capable of sufficiently imparting activity to AMPK for one hour were mixed in a buffer solution consisting of a 50 mM HEPES-NaOH buffer solution (pH 7.0), 100 mM NaCl, 5 mM magnesium chloride, 0.1% bovine serum albumin, 0.2 mM sodium orthovanadate (V), 1 mM ethylene glycol-bis(2-aminoethyl ether)-N,N,N', N'-tetraacetic acid (EGTA), 5 mM disodium β-glycerophosphate, 1 mM dithiothreitol and 0.2 mM ATP, and the obtained liquid was left to stand at 25° C. for 1 to 1.5 hours to sufficiently phosphorylate AMPK.

After that, to the enzyme liquid, which had been subjected to phosphorylation treatment, a compound dissolved in DMSO was added so as to have a 1% DMSO concentration. The obtained liquid was left to stand for 10 minutes.

To the liquid, a substrate solution consisting of a 50 mM HEPES-NaOH buffer solution (pH 7.0), 100 mM NaCl, 10 mM magnesium chloride, 0.1% bovine serum albumin, 0.2 mM sodium orthovanadate(V), 1 mM ethylene glycol-bis (2-aminoethyl ether)-N,N,N',N'-tetraacetic acid (EGTA), 5 mM disodium β-glycerophosphate, 2 mM dithiothreitol, 0.4 mM ATP and 3 μM FL-Peptide 7 (manufactured by Caliper Life Sciences, Inc.) was added in equal amount (10 μl in total). The obtained liquid was allowed to react at 25° C. for 2 hours, and 10 μl of 20 mM EDTA was then added thereto to stop the reaction.

To detect phosphorylated fluorescent substrates, the reaction liquid was applied to a measuring device, LabChip EZ Reader II manufactured by Caliper Life Science, Inc., for detecting fluorescence by using differences in mobility due to differences in charge. The setting conditions for the device were pressure, −1.5 PSI; upstream voltage, −2250 V; downstream voltage, −400 V; post sample buffer sip time, 40 seconds; final delay, 120 seconds; and peak order, Product First.

A conversion rate was calculated from the peak heights of the resulting substrate and product. The conversion rate when not containing a compound was used as a control, and a concentration dependent curve was made by plotting the rate of increase in activity to the control at each concentration of a compound. The compound concentration showing 150% relative to the control (100%) was used as the EC 150 value, and the maximum rate of increase in activity within the measurement range was used as Emax.

The results of Test Example 2 are shown below.
Compound (I-1-1): EC150=68 nM, Emax=596%
Compound (I-1-6): EC150=76 nM, Emax=618%
Compound (I-1-8): EC150=39 nM, Emax=580%
Compound (I-1-9): EC150=20 nM, Emax=559%
Compound (I-2-1): EC150=87 nM, Emax=559%
Compound (I-2-3): EC150=67 nM, Emax=502%
Compound (I-2-9): EC150=34 nM, Emax=503%
Compound (I-2-17): EC150=98 nM, Emax=587%
Compound (I-3-9): EC150=39 nM, Emax=446%
Compound (I-3-15): EC150=1.9 nM, Emax=559%
Compound (I-3-18): EC150=4.1 nM, Emax=489%
Compound (I-3-21): EC150=0.21 nM, Emax=787%
Compound (I-3-22): EC150=120 nM, Emax=264%
Compound (I-3-24): EC150=8.8 nM, Emax=729%
Compound (I-3-28): EC150=54 nM, Emax=510%
Compound (I-3-32): EC150=2.6 nM, Emax=661%
Compound (I-3-38): EC150=3.9 nM, Emax=560%
Compound (I-3-45): EC150=26 nM, Emax=694%
Compound (I-3-46): EC150=0.48 nM, Emax=750%
Compound (I-3-47): EC150=0.76 nM, Emax=727%
Compound (I-3-49): EC150=18 nM, Emax=848%

The compounds of the present invention have an excellent activating effect on an AMPK al trimer and/or an AMPK α2 trimer.

Comparative Example 1

Compound A-1 described in Patent Document 7 was synthesized by the method described in Patent Document 7.

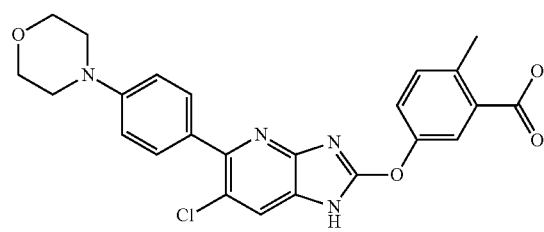

A-1

According to the method described in Test Example 2, the AMPK activating effect of Compound A-1 was measured. The result is shown below.
Compound (A-1): EC150=130 nM, Emax=394%

On the other hand, the effect of Compound (I-3-50) of the present invention on Test Example 2 is shown below.

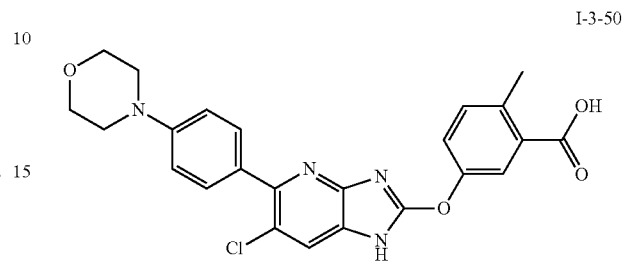

I-3-50

Compound (I-3-50): EC150=63 nM, Emax=435%

Therefore Compound (I-3-50) of the present invention has a superior AMPK activating effect to Compound (A-1) described in Patent Document 7.

Comparative Example 2

The following Compound (B-1) which fall within the scope of the claims of Patent Document 8, was synthesized by the method described in Patent Document 8.

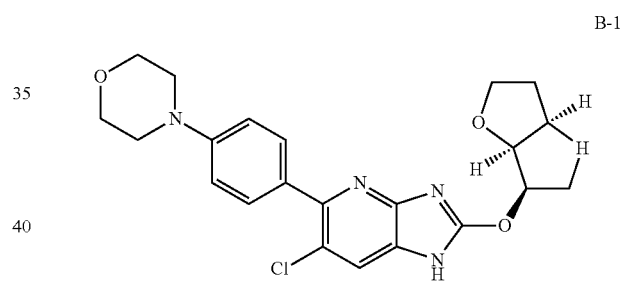

B-1

The phototoxicity test of Compound (B-1) was confirmed. Compound (B-1) was positive.

On the other hand, Compound (I-3-37) of the present invention was negative.

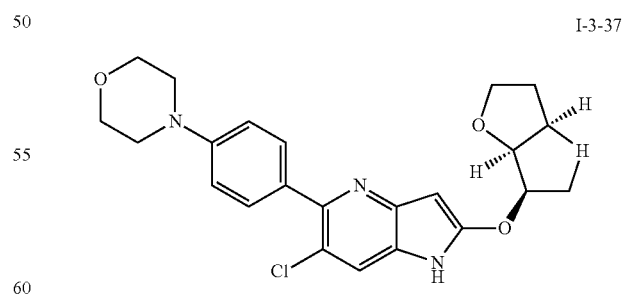

I-3-37

Usefulness as a medicament can be examined by the following tests etc. CYP3A4 fluorescent MBI test The CYP3A4 fluorescent MBI test is a test of investigating enhancement of CYP3A4 inhibition of a compound by a metabolism reaction, and the test was performed using, as CYP3A4 enzyme expressed in *Escherichia coli* and employing, as an index, a reaction in which 7-benzyloxytrifluorom-ethylchmarin (7-BFC) is debenzylated by the CYP3A4 enzyme to produce a metabolite, 7-hydroxytrifluoromethyl-chmarin (HFC) emitting fluorescent light.

The reaction conditions were as follows: substrate, 5.6 µmol/L 7-BFC; pre-reaction time, 0 or 30 minutes; reaction time, 15 minutes; reaction temperature, 25° C. (room temperature); CYP3A4 content (enzyme expressed in *Escherichia* call), at pre-reaction 62.5 pmol/mL, at reaction 6.25 pmol/mL (at 10-fold dilution); test drug concentration, 0.625, 1.25, 2.5, 5, 10, 20 µmol/L (six points).

An enzyme in a K-Pi buffer (pH 7.4) and a test drug solution as a pre-reaction solution were added to a 96-well plate at the composition of the pre-reaction, a part of it was transferred to another 96-well plate so that it was 1/10 diluted with a substrate and a K-Pi buffer, NADPH as a co-factor was added to initiate a reaction as an index (without preincubation) and, after a predetermined time of a reaction, acetonitrile/0.5 mol/L Tris (trishydroxyamin-omethane)=4/1 was added to stop the reaction. In addition, NADPH was added to a remaining preincubation solution to initiate a preincubation (with preincubation) and, after a predetermined time of a preincubation, a part was transferred to another plate so that it was 1/10 diluted with a substrate and a K-Pi buffer to initiate a reaction as an index. After a predetermined time of a reaction, acetonitrile/0.5 mol/L Tris (trishydroxyaminomethane)=4/1 was added to stop the reaction. For the plate on which each index reaction had been performed, a fluorescent value of 7-HFC which is a metabolite was measured with a fluorescent plate reader. (Ex=420 nm, Em=535 nm).

Addition of only DMSO which is a solvent dissolving a drug to a reaction system was adopted as a control (100%), remaining activity (%) was calculated at each concentration of a test drug added as the solution, and $IC_{50}$ was calculated by reverse-presumption by a logistic model using a concentration and an inhibition rate. When a difference between $IC_{50}$ values is 5 µM or more, this was defined as (+) and, when the difference is 3 µM or less, this was defined as (+).

CYP Inhibition Test

Using commercially available pooled human hepatic microsome, and employing, as markers, 7-ethoxyresorufin O-deethylation (CYP1A2), tolbutamide methyl-hydroxy-lation (CYP2C9), mephenytoin 4'-hydroxylation (CYP2C19), dextromethorphan O-demethylation (CYP2D6), and terfenedine hydroxylation (CYP3A4) as typical substrate metabolism reactions of human main five CYP enzyme forms (CYP1A2, 2C9, 2C19, 2D6, 3A4), an inhibitory degree of each metabolite production amount by a test compound was assessed.

The reaction conditions were as follows: substrate, 0.5 µmol/L ethoxyresorufin (CYP1A2), 100 µmol/L tolbutamide (CYP2C9), 50 µmol/L S-mephenitoin (CYP2C19), 5 µmol/L dextromethorphan (CYP2D6), 1 µmol/L terfenedine (CYP3A4); reaction time, 15 minutes; reaction temperature, 37° C.; enzyme, pooled human hepatic microsome 0.2 mg protein/mL; test drug concentration, 1, 5, 10, 20 µmol/L (four points).

Each five kinds of substrates, human hepatic microsome, or a test drug in 50 mM Hepes buffer as a reaction solution was added to a 96-well plate at the composition as described above, NADPH, as a cofactor was added to initiate metabolism reactions as markers, and after the incubation at 37° C. for 15 minutes, a methanol/acetonitrile=1/1 (v/v) solution was added to stop the reaction. After the centrifugation at 3000 rpm for 15 minutes, resorufin (CYP1A2 metabolite) in the supernatant was quantified by a fluorescent multilabel counter and tributamide hydroxide (CYP2C9 metabolite), mephenytoin 4' hydroxide (CYP2C19 metabolite), dextromethorphan (CYP2D6 metabolite), and terfenadine alcohol (CYP3A4 metabolite) were quantified by LC/MS/MS.

Addition of only DMSO being a solvent dissolving a drug to a reaction system was adopted as a control (100%), remaining activity (%) was calculated at each concentration of a test drug added as the solution and $IC_{50}$ was calculated by reverse presumption by a logistic model using a concentration and an inhibition rate.

FAT Test

Each 20 µL of freeze-stored *Salmonella typhimurium* (TA98 and TA100 strain) was inoculated in 10 mL of liquid nutrient medium (2.5% Oxoid nutrient broth No. 2), and the cultures were incubated at 37° C. under shaking for 10 hours. 9 mL of TA98 culture was centrifuged (2000×g, 10 minutes) to remove medium, and the bacteria was suspended in 9 mL of Micro F buffer ($K_2HPO_4$: 3.5 g/L, $KH_2PO_4$: 1 g/L, $(NH_4)_2SO_4$: 1 g/L, trisodium citrate dihydrate: 0.25 g/L, $MgSO_4.7H_2O$: 0.1 g/L), and the suspension was added to 110 mL of Exposure medium (Micro F buffer containing Biotin: 8 µg/mL, histidine 0.2 µg/mL, glucose: 8 mg/mL). 3.16 mL of TA100 culture was added to 120 mL of Exposure medium to prepare the test bacterial solution. 588 µL of the test bacterial solution (or mixed solution of 498 µl of the test bacterial solution and 90 µL of the S9 mix in the case with metabolic activation system) was mixed with each 12 µL of the following solution: DMSO solution of the test substance (eight dose levels from maximum dose 50 mg/mL at 2-fold ratio); DMSO as negative control; 50 µg/mL of 4-nitroqui-noline-1-oxide DMSO solution as positive control for TA98 without metabolic activation system; 0.25 µg/mL of 2-(2-furyl)-3-(5-nitro-2-furyl)acrylamide DMSO solution as positive control for TA100 without metabolic activation system; 40 µg/mL of 2-aminoanthracene DMSO solution as positive control for TA98 with metabolic activation system; or 20 µg/mL of 2-aminoanthracene DMSO solution as positive control for TA100 with metabolic activation system. 12 µL of the solution and 588 µL of the test bacterial solution (a mixed solution of 498 µl of the test bacterial solution and 90 µL of S9 mix with metabolic activation condition) were mixed and incubated at 37° C. under shaking for 90 minutes. 460 µL of the bacterial solution exposed to the test substance was mixed with 2300 µL of Indicator medium (Micro F buffer containing biotin: 8 µg/mL, histidine: 0.2 µg/mL, glucose: 8 mg/mL, Bromo Cresol Purple: 37.5 µg/mL), each 504 was dispensed into 48 wells per dose in the microwell plates, and was subjected to stationary cultivation at 37° C. for 3 days. A well containing the bacteria, which has obtained the ability of proliferation by mutation in the gene coding amino acid (histidine) synthetase, turns the color from purple to yellow due to pH change. The number of the yellow wells among the 48 total wells per dose was counted, and evaluated the mutagenicity by comparing with the negative control group.

Solubility Test

The solubility of a compound was determined under a condition in which 1% DMSO was added. 10 mM compound solution was prepared using DMSO, and then 6 µL of the compound solution was added to 594 µL of artificial intestinal juice in pH 6.8 (to 250 mL of 0.2 mol/L potassium dihydrogen phosphate reagent solution was added 118 mL of 0.2 mol/L NaOH reagent solution and water to provide a final volume of 1000 mL). After standing at 25 degrees Celsius for 16 hours, the mixed solution was filtrated with suction. The filtrate was diluted twice with methanol/water (1/1), and then a concentration in the filtration was measured with HPLC or LC/MS/MS by the absolute calibration method.

Metabolic Stability Test

Using commercially available pooled human hepatic microsomes, a test compound was reacted for a constant time, a remaining rate was calculated by comparing a reacted sample and an unreacted sample, thereby, a degree of metabolism in liver was assessed.

A reaction was performed (oxidative reaction) at 37° C. for 0 minute or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human liver microsomes. After the reaction, 50 µL of the reaction solution was added to 100 µL of a methanol/acetonitrile=1/1 (v/v), mixed and centrifuged at 3000 rpm for 15 minutes. The test compound in the supernatant was quantified by LC/MS/MS, and a remaining amount of the test compound after the reaction was calculated, letting a compound amount at 0 minute reaction time to be 100%. Hydrolysis reaction was performed in the absence of NADPH and glucuronidation reaction was performed in the presence of 5 mM UDP-glucuronic acid in place of NADPH, followed by similar operations.

hERG Test

For the purpose of assessing risk of an electrocardiogram QT interval prolongation, effects on delayed rectifier K$^+$ current ($I_{Kr}$), which plays an important role in the ventricular repolarization process, was studied using HEK293 cells expressing human ether-a-go-go related gene (hERG) channel.

After a cell was retained at a membrane potential of −80 mV by whole cell patch clamp method using an automated patch clamp system (PatchXpress 7000A, Axon Instruments Inc.), $I_{Kr}$ induced by depolarization pulse stimulation at +40 mV for 2 seconds and, further, repolarization pulse stimulation at −50 mV for 2 seconds was recorded. After the generated current was stabilized, extracellular solution (NaCl: 135 mmol/L, KCl: 5.4 mmol/L, NaH$_2$PO$_4$: 0.3 mmol/L, CaCl$_2$.2H$_2$O: 1.8 mmol/L, MgCl$_2$.6H$_2$O: 1 mmol/L, glucose: 10 mmol/L, HEPES (4-(2-hydroxyethyl)-1-piperazine ethanesulfonic acid): 10 mmol/L, pH=7.4) in which the test compound had been dissolved at an objective concentration was applied to the cell under the room temperature condition for 10 minutes. From the recording $I_{Kr}$, an absolute value of the tail peak current was measured based on the current value at the resting membrane potential using an analysis software (DataXpress ver.1, Molecular Devices Corporation). Further, the % inhibition relative to the tail peak current before application of the test substance was calculated, and compared with the vehicle-applied group (0.1% dimethyl sulfoxide solution) to assess influence of the test substance on $I_{Kr}$.

Powder Solubility Test

Appropriate amounts of the test substances were put into appropriate containers. To the respective containers were added 2004 of JP-1 fluid (sodium chloride 2.0 g, hydrochloric acid 7.0 mL and water to reach 1000 mL), 200 µL of JP-2 fluid (phosphate buffer (pH 6.8) 500 mL and water 500 mL), and 200 µl of 20 mmol/L TCA (sodium taurocholate)/JP-2 fluid (TCA 1.08 g and water to reach 100 mL). In the case that the test compound was dissolved after the addition of the test fluid, the bulk powder was added as appropriate. The containers were sealed, and shaken for 1 hour at 37° C. The mixtures were filtered, and 100 µL of methanol was added to each of the filtrate (100 µL) so that the filtrates were two-fold diluted. The dilution ratio was changed if necessary. After confirmation of no bubbles and precipitates, the containers were sealed and shaken. Quantification was performed by HPLC with an absolute calibration method.

BA Test

Materials and methods for studies on oral absorption (1) Animals: mice or rats (2) Animal husbandry:

Mice and rats had free access to solid food and sterilized bottled tap water.

(3) Setting of Dose and group compositions:

orally or intravenously administered at a predetermined dose; Group compositions were as shown below (Dose depends on the compound)

Oral: 1 to 30 mg/kg (n=2 to 3)

Intravenous: 0.5 to 10 mg/kg (n=2 to 3)

(4) Preparation for dosing formulation:

for oral administration, in a solution or a suspension state; for intravenous administration, in a solubilized state (5) Dosing procedure:

In oral administration study, the test suspension was dosed to the stomach of rats by using a gavage tube In intravenous administration study, the test solution was dosed to rats via tail vein using a syringe with a needle.

(6) Evaluation items:

Blood was collected at each time point, and plasma concentration of the test substance was determined by a LC/MS/MS system.

(7) Data analysis:

Regarding the transition of the plasma concentration, area under the plasma concentration-time curve (AUC) was calculated by means of WinNonlin® program, respectively. Bioavailability (BA) was calculated by using AUC values in oral administration study and in intravenous administration study.

Formulation Examples are shown below.

Formulation Example 1: Tablets

The compounds of the present invention, lactose and calcium stearate are mixed. The mixture is crushed, granulated and dried to give a suitable size of granules. Next, calcium stearate is added to the granules, and the mixture is compressed and molded to give tablets.

Formulation Example 2: Capsules

The compounds of the present invention, lactose and calcium stearate are mixed uniformly to obtain powder medicines in the form of powders or fine granules. The powder medicines are filled into capsule containers to give capsules.

Formulation Example 3: Granules

The compounds of the present invention, lactose and calcium stearate are mixed uniformly and the mixture is compressed and molded. Then, it is crushed, granulated and sieved to give suitable sizes of granules.

Formulation Example 4: Orally Disintegrated Tablets

The compounds of the present invention and crystalline cellulose are mixed, granulated and tablets are made to give orally disintegrated tablets.

Formulation Example 5: Dry Syrups

The compounds of the present invention and lactose are mixed, crushed, granulated and sieved to give suitable sizes of dry syrups.

Formulation Example 6: Injections

The compounds of the present invention and phosphate buffer are mixed to give injection.

Formulation Example 7: Infusions

The compounds of the present invention and phosphate buffer are mixed to give injection.

Formulation Example 8: Inhalations

The compound of the present invention and lactose are mixed and crushed finely to give inhalations.

Formulation Example 9: Ointments

The compounds of the present invention and petrolatum are mixed to give ointments.

Formulation Example 10: Patches

The compounds of the present invention and base such as adhesive plaster or the like are mixed to give patches.

INDUSTRIAL APPLICABILITY

As is apparent from the above test examples, the compounds of the present invention show an AMPK activating effect. Therefore, the compounds of the present invention are very useful as a therapeutic agent for type II diabetes, hyperglycemia, metabolic syndrome, obesity, hypercholesterolemia and hypertension.

The invention claimed is:
1. A compound represented by formula (I):

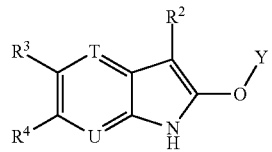

or its pharmaceutically acceptable salt,
wherein
Y is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;
T —N=;
U is —$CR^8$= or —N=;
$R^2$ is hydrogen, halogen, cyano, nitro, carboxy, substituted or unsubstituted alkyl, substituted or unsubstituted alkenyl, substituted or unsubstituted acyl, substituted or unsubstituted carbamoyl, substituted or unsubstituted alkylthio, substituted or unsubstituted alkylsulfinyl, substituted or unsubstituted alkylsulfonyl, or substituted or unsubstituted alkyloxycarbonyl;
$R^3$ is halogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;
$R^4$ is hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino; and
$R^8$ is hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino.

2. The compound according to claim 1 or its pharmaceutically acceptable salt, wherein Y is substituted or unsubstituted aryl, substituted or unsubstituted heteroaryl, substituted or unsubstituted cycloalkyl, substituted or unsubstituted cycloalkenyl, or substituted or unsubstituted heterocyclyl.

3. The compound according to claim 1 or its pharmaceutically acceptable salt, wherein Y is substituted or unsubstituted aryl, substituted or unsubstituted cycloalkyl, or substituted or unsubstituted heterocyclyl.

4. The compound according to claim 1 or its pharmaceutically acceptable salt, wherein Y is substituted or unsubstituted heterocyclyl.

5. The compound according to claim 4 or its pharmaceutically acceptable salt, wherein Y is substituted or unsubstituted heterocyclyl and the substituted or unsubstituted heterocyclyl is

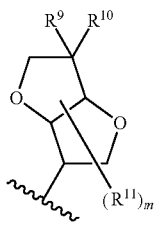

wherein $R^9$ and $R^{10}$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino;

$R^{11}$ is each independently halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino;

m is an integer from 0 to 7.

6. The compound according to claim 1 or its pharmaceutically acceptable salt, wherein $R^3$ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino.

7. The compound according to claim 1 or its pharmaceutically acceptable salt, wherein $R^3$ is substituted or unsubstituted aryl, substituted or unsubstituted heteroaryl, or substituted or unsubstituted alkyloxy.

8. The compound according to claim 1 or its pharmaceutically acceptable salt, wherein $R^3$ is substituted or unsubstituted aryl.

9. The compound according to claim 1 or its pharmaceutically acceptable salt, wherein $R^2$ is hydrogen, halogen, cyano, carboxy, or substituted or unsubstituted carbamoyl.

10. The compound according to claim 9 or its pharmaceutically acceptable salt, wherein $R^2$ is hydrogen, halogen, or cyano.

11. The compound according to claim 1 or its pharmaceutically acceptable salt, wherein $R^4$ is hydrogen or halogen.

12. The compound according to claim 1 or its pharmaceutically acceptable salt, wherein U is $-CR^8=$.

13. A pharmaceutical composition, comprising:
the compound according to claim 1 or its pharmaceutically acceptable salt; and
a pharmaceutically acceptable excipient.

14. The pharmaceutical composition according to claim 13, which has an activating effect on adenosine monophosphate-activated protein kinase.

15. A method for treating diabetes, hyperglycemia, metabolic syndrome, obesity, hypercholesterolemia or hypertension, comprising:
administering the compound according to claim 1 or its pharmaceutically acceptable salt.

16. The compound according to claim 1 or its pharmaceutically acceptable salt, wherein U is $-N=$.

17. A pharmaceutical composition, comprising:
the compound according to claim 2 or its pharmaceutically acceptable salt; and
a pharmaceutically acceptable excipient.

18. A pharmaceutical composition, comprising:
the compound according to claim 3 or its pharmaceutically acceptable salt; and
a pharmaceutically acceptable excipient.

19. A pharmaceutical composition, comprising:
the compound according to claim 4 or its pharmaceutically acceptable salt; and
a pharmaceutically acceptable excipient.

20. A pharmaceutical composition, comprising:
the compound according to claim 5 or its pharmaceutically acceptable salt; and
a pharmaceutically acceptable excipient.

* * * * *